(12) United States Patent
Shastry et al.

(10) Patent No.: US 10,660,619 B2
(45) Date of Patent: May 26, 2020

(54) CARTRIDGES FOR ORAL FLUID ANALYSIS AND METHODS OF USE

(71) Applicant: EVANOSTICS LLC, Los Gatos, CA (US)

(72) Inventors: Ashutosh Shastry, Santa Clara, CA (US); Pranav Chopra, Los Gatos, CA (US); Leah Yablok, Los Gatos, CA (US); Ameya Kantak, Los Gatos, CA (US); Sukhleen Saini, Los Gatos, CA (US)

(73) Assignee: Evanostics LLC, Los Gatos, CA (US)

( * ) Notice: Subject to any disclaimer, the term of this patent is extended or adjusted under 35 U.S.C. 154(b) by 0 days.

(21) Appl. No.: 16/040,506

(22) Filed: Jul. 19, 2018

(65) Prior Publication Data

US 2019/0021704 A1    Jan. 24, 2019

Related U.S. Application Data

(60) Provisional application No. 62/534,394, filed on Jul. 19, 2017.

(51) Int. Cl.
*A61B 10/00*    (2006.01)
*G01N 1/10*    (2006.01)
(Continued)

(52) U.S. Cl.
CPC .......... *A61B 10/0051* (2013.01); *G01N 1/10* (2013.01); *G01N 21/6428* (2013.01); *G01N 33/948* (2013.01); *A61B 5/1455* (2013.01); *A61B 2010/0006* (2013.01); *A61B 2010/0009* (2013.01); *A61F 13/38* (2013.01); *G01N 1/38* (2013.01); *G01N 21/6408* (2013.01); *G01N 21/81* (2013.01); *G01N 2001/028* (2013.01); *G01N 2021/6439* (2013.01)

(58) Field of Classification Search
None
See application file for complete search history.

(56) References Cited

U.S. PATENT DOCUMENTS 3,792,699 A * 2/1974 Tobin ................. A61B 10/0096
600/572
5,520,787 A * 5/1996 Hanagan ............... B01L 3/5027
204/403.14

(Continued)

FOREIGN PATENT DOCUMENTS

EP    1178316 B1    1/2005
EP    2616797 B1    1/2017

(Continued)

OTHER PUBLICATIONS

Shastry et al.; U.S. Appl. No. 16/223,096 entitled "Optical reader for analyte testing," filed Dec. 17, 2018.

*Primary Examiner* — Matthew Kremer
(74) *Attorney, Agent, or Firm* — Shay Glenn LLP

(57) ABSTRACT

A disposable cartridge can be used for biofluid sample collection, preparation, and mixing with reagents. After sample collection, the cartridge can be inserted into a reader for sample analysis. This system can be used for detecting and measuring analytes, such as drugs, in saliva for example. This is useful for point of test detection of drugs in applications such as workplace drug testing and driving under the influence of drugs testing.

23 Claims, 29 Drawing Sheets

(51) Int. Cl.
    *G01N 21/64*     (2006.01)
    *G01N 33/94*     (2006.01)
    *G01N 1/38*     (2006.01)
    *A61B 5/1455*     (2006.01)
    *G01N 1/02*     (2006.01)
    *G01N 21/81*     (2006.01)
    *A61F 13/38*     (2006.01)

(56) References Cited

U.S. PATENT DOCUMENTS

| | | | |
|---|---|---|---|
| 5,827,675 A * | 10/1998 | Skiffington | B01L 3/502 |
| | | | 435/8 |
| 6,416,642 B1 * | 7/2002 | Alajoki | B01J 19/0093 |
| | | | 204/451 |
| 6,635,226 B1 * | 10/2003 | Tso | B01L 3/5027 |
| | | | 422/129 |
| 6,716,392 B1 | 4/2004 | Putcha et al. | |
| 6,942,771 B1 * | 9/2005 | Kayyem | B01L 3/5027 |
| | | | 204/409 |
| 7,029,627 B2 | 4/2006 | Alley | |
| 7,294,502 B2 | 11/2007 | Eckermann et al. | |
| 7,374,723 B2 | 5/2008 | Wuske et al. | |
| 7,618,591 B2 | 11/2009 | Slowey et al. | |
| 7,708,945 B1 | 5/2010 | Abel et al. | |
| 7,713,703 B1 | 5/2010 | Buechler et al. | |
| 7,741,103 B2 * | 6/2010 | Guirguis | A61B 10/0051 |
| | | | 422/504 |
| 7,781,226 B2 | 8/2010 | McDevitt et al. | |
| 7,790,400 B2 | 9/2010 | Jehanli et al. | |
| 7,837,939 B2 | 11/2010 | Tung et al. | |
| 7,888,040 B2 | 2/2011 | Jehanli | |
| 7,888,130 B2 | 2/2011 | Wuske et al. | |
| 7,927,548 B2 | 4/2011 | Slowey et al. | |
| 7,955,558 B2 | 6/2011 | Weekamp et al. | |
| 8,025,849 B2 | 9/2011 | Baldwin et al. | |
| 8,025,851 B2 | 9/2011 | Slowey et al. | |
| 8,101,431 B2 | 1/2012 | McDevitt et al. | |
| 8,105,849 B2 | 1/2012 | McDevitt et al. | |
| 8,174,700 B2 | 5/2012 | Chinowsky et al. | |
| 8,222,024 B2 | 7/2012 | Davis et al. | |
| 8,273,305 B2 | 9/2012 | Slowey et al. | |
| 8,288,157 B2 | 10/2012 | Duer | |
| 8,300,993 B2 | 10/2012 | Moll et al. | |
| 8,331,751 B2 | 12/2012 | Delaney et al. | |
| 8,506,898 B2 | 8/2013 | Perez | |
| RE44,539 E | 10/2013 | Thompson et al. | |
| 8,586,347 B2 | 11/2013 | Lochhead et al. | |
| 8,675,199 B2 | 3/2014 | Duer | |
| 8,881,580 B2 | 11/2014 | Lundgreen et al. | |
| 8,906,303 B2 | 12/2014 | Ermantraut et al. | |
| 9,012,163 B2 | 4/2015 | Burd et al. | |
| 9,034,634 B2 | 5/2015 | Miller | |
| 9,040,288 B2 | 5/2015 | Handique et al. | |
| 9,072,425 B1 | 7/2015 | Bogema | |
| 9,176,126 B2 | 11/2015 | Holmes et al. | |
| 9,179,895 B2 | 11/2015 | Jowett et al. | |
| 9,194,859 B2 | 11/2015 | Emeric et al. | |
| 9,198,641 B2 | 12/2015 | Slowey et al. | |
| 9,204,865 B2 | 12/2015 | Polzius et al. | |
| 9,212,995 B2 | 12/2015 | Moll et al. | |
| 9,267,939 B2 | 2/2016 | Campbell et al. | |
| 9,417,210 B2 | 8/2016 | Arlen et al. | |
| 9,423,397 B2 | 8/2016 | Duer | |
| 9,528,939 B2 | 12/2016 | Duer | |
| RE46,351 E | 3/2017 | Apel et al. | |
| 9,658,222 B2 | 5/2017 | Moll et al. | |
| 9,709,580 B2 | 7/2017 | McDevitt et al. | |
| 9,841,396 B2 | 12/2017 | Miller et al. | |
| 9,846,126 B2 | 12/2017 | Gunn et al. | |
| 2003/0175947 A1 * | 9/2003 | Liu | B01F 11/0071 |
| | | | 435/288.5 |
| 2006/0216196 A1 * | 9/2006 | Satoh | B01L 3/5029 |
| | | | 422/400 |
| 2006/0257854 A1 | 11/2006 | McDevitt et al. | |
| 2006/0257941 A1 | 11/2006 | McDevitt et al. | |
| 2006/0257991 A1 | 11/2006 | McDevitt et al. | |
| 2006/0292034 A1 | 12/2006 | Gould et al. | |
| 2006/0292040 A1 | 12/2006 | Wickstead et al. | |
| 2007/0263049 A1 | 11/2007 | Preckel et al. | |
| 2008/0118397 A1 * | 5/2008 | Slowey | A61B 10/0051 |
| | | | 422/400 |
| 2011/0028346 A1 | 2/2011 | Chakravarty et al. | |
| 2012/0282154 A1 * | 11/2012 | Slowey | G01N 21/8483 |
| | | | 422/401 |
| 2013/0102003 A1 | 4/2013 | Gibbs | |
| 2013/0309778 A1 | 11/2013 | Lowe et al. | |
| 2015/0010903 A1 | 1/2015 | Schawaller et al. | |
| 2015/0111778 A1 | 4/2015 | McDevitt et al. | |
| 2015/0346097 A1 | 12/2015 | Battrell et al. | |
| 2015/0352549 A1 | 12/2015 | Kolb et al. | |
| 2016/0033412 A1 | 2/2016 | Tan et al. | |
| 2016/0157836 A1 | 6/2016 | Borg et al. | |
| 2016/0187239 A1 | 6/2016 | Givens et al. | |
| 2016/0331356 A1 | 11/2016 | Binner et al. | |
| 2017/0014822 A1 | 1/2017 | Ker | |
| 2017/0016827 A1 | 1/2017 | Gervais et al. | |
| 2017/0023477 A1 | 1/2017 | Duer et al. | |
| 2017/0045507 A1 | 2/2017 | Khattak et al. | |
| 2017/0120238 A1 | 5/2017 | Bodner | |
| 2017/0370836 A1 | 12/2017 | Gerion et al. | |

FOREIGN PATENT DOCUMENTS

| | | |
|---|---|---|
| EP | 2627987 B1 | 9/2017 |
| WO | WO2005/072398 A2 | 8/2005 |
| WO | WO2005/083423 A2 | 9/2005 |
| WO | WO2009/012307 A2 | 1/2009 |
| WO | WO2012/032294 A1 | 3/2012 |
| WO | WO2016/138427 A1 | 9/2016 |
| WO | WO2017/059425 A1 | 4/2017 |
| WO | WO2018/015931 A1 | 1/2018 |

\* cited by examiner

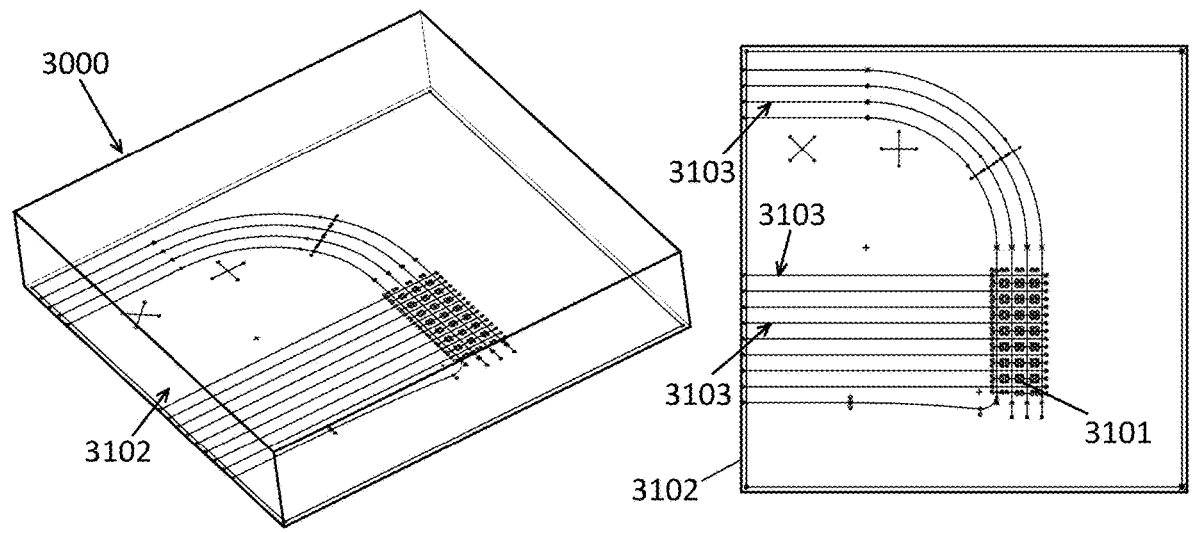
FIG. 8A  FIG. 8B
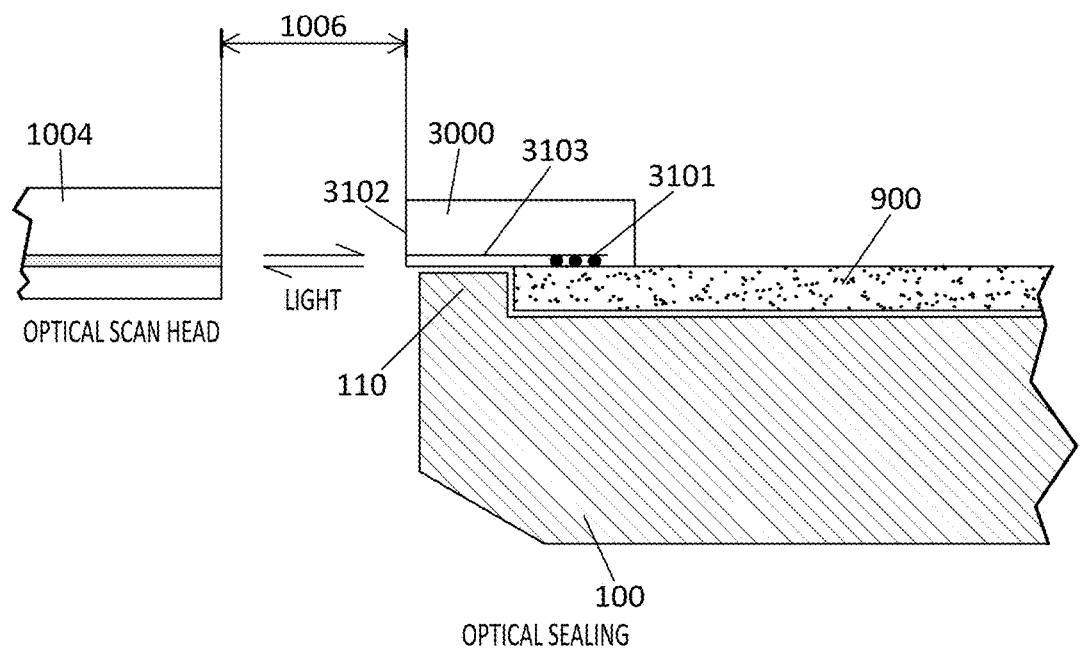
FIG. 9A

| ASSAY | SIGNAL CUT-OFF | RESOLUTION | FALSE POSITIVE AT 0.6X | FALSE NEGATIVE AT 1.4X | FALSE POSITIVE AT 0.25X | FALSE NEGATIVE AT 1.75X |
|---|---|---|---|---|---|---|
| BZO | 0.52 | 0.32 | 2% | 2% | 0.005% | 0.642% |
| THC | 0.71 | 0.18 | 6% | 4% | 0.033% | 0.001% |
| COC | -0.19 | 0.24 | 4% | 6% | 0.000% | 0.000% |

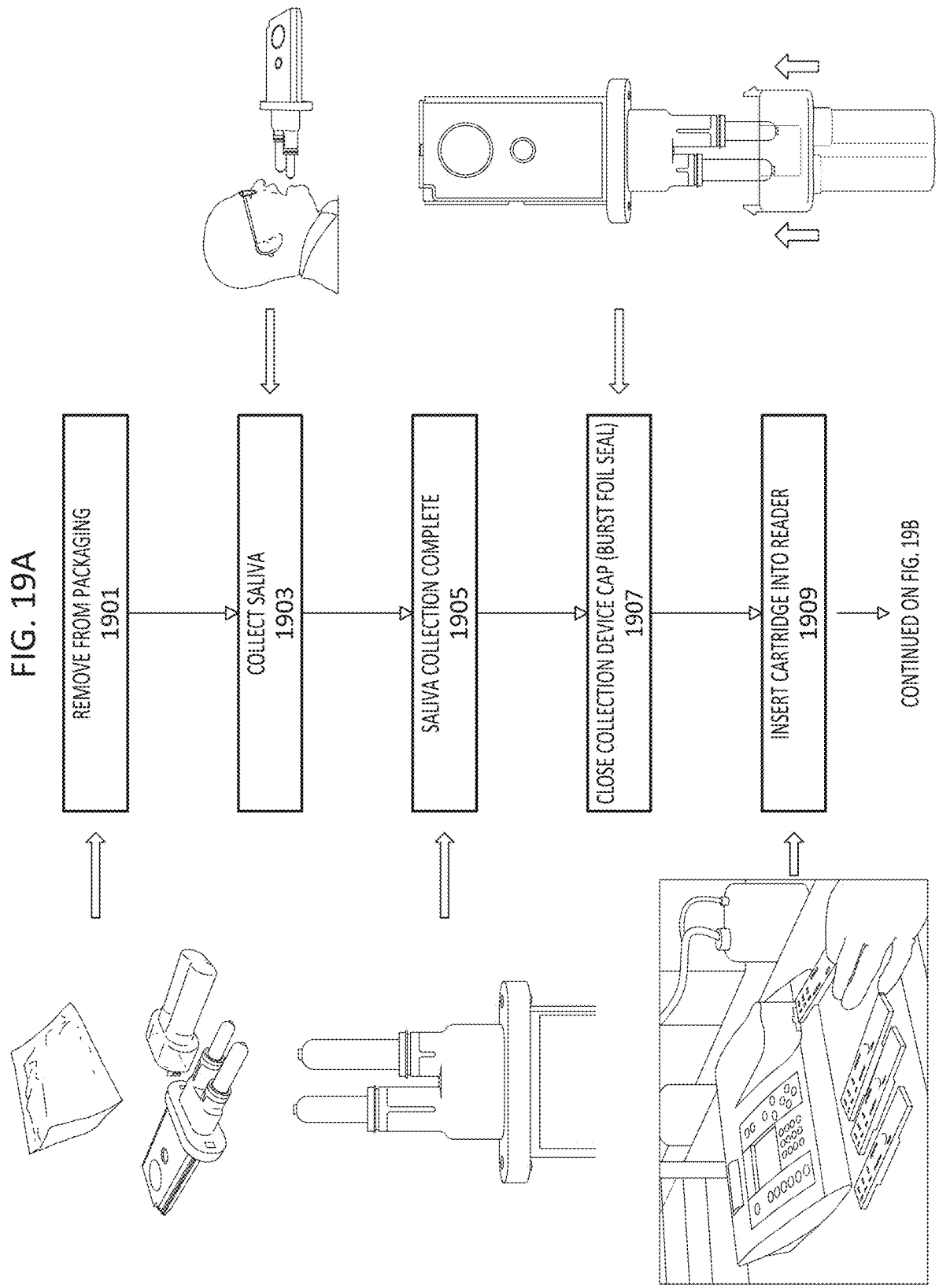

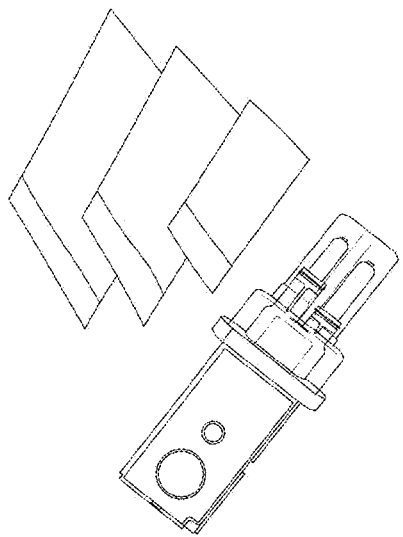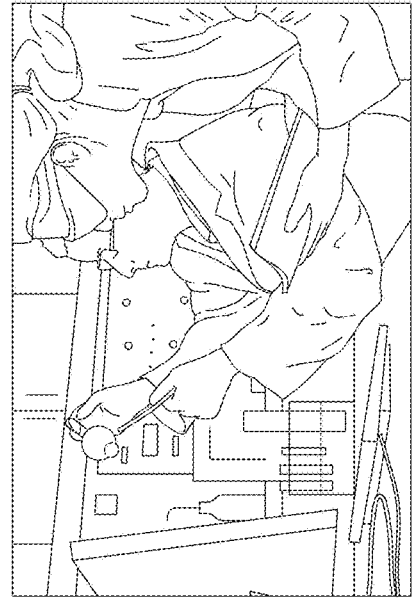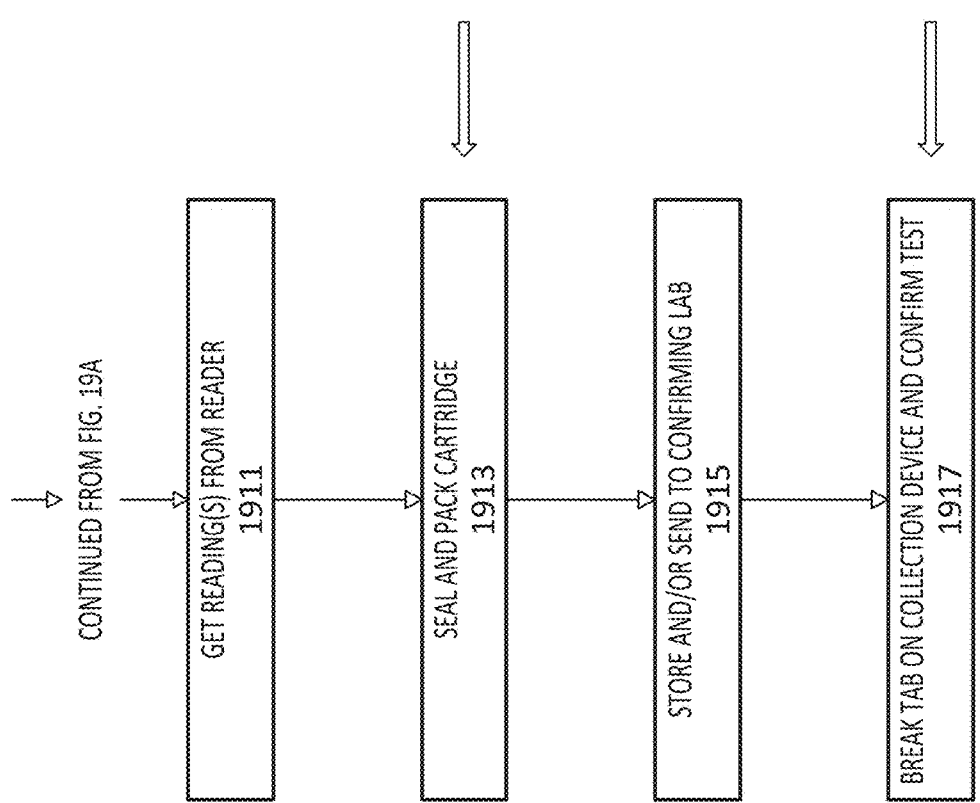
FIG. 19B

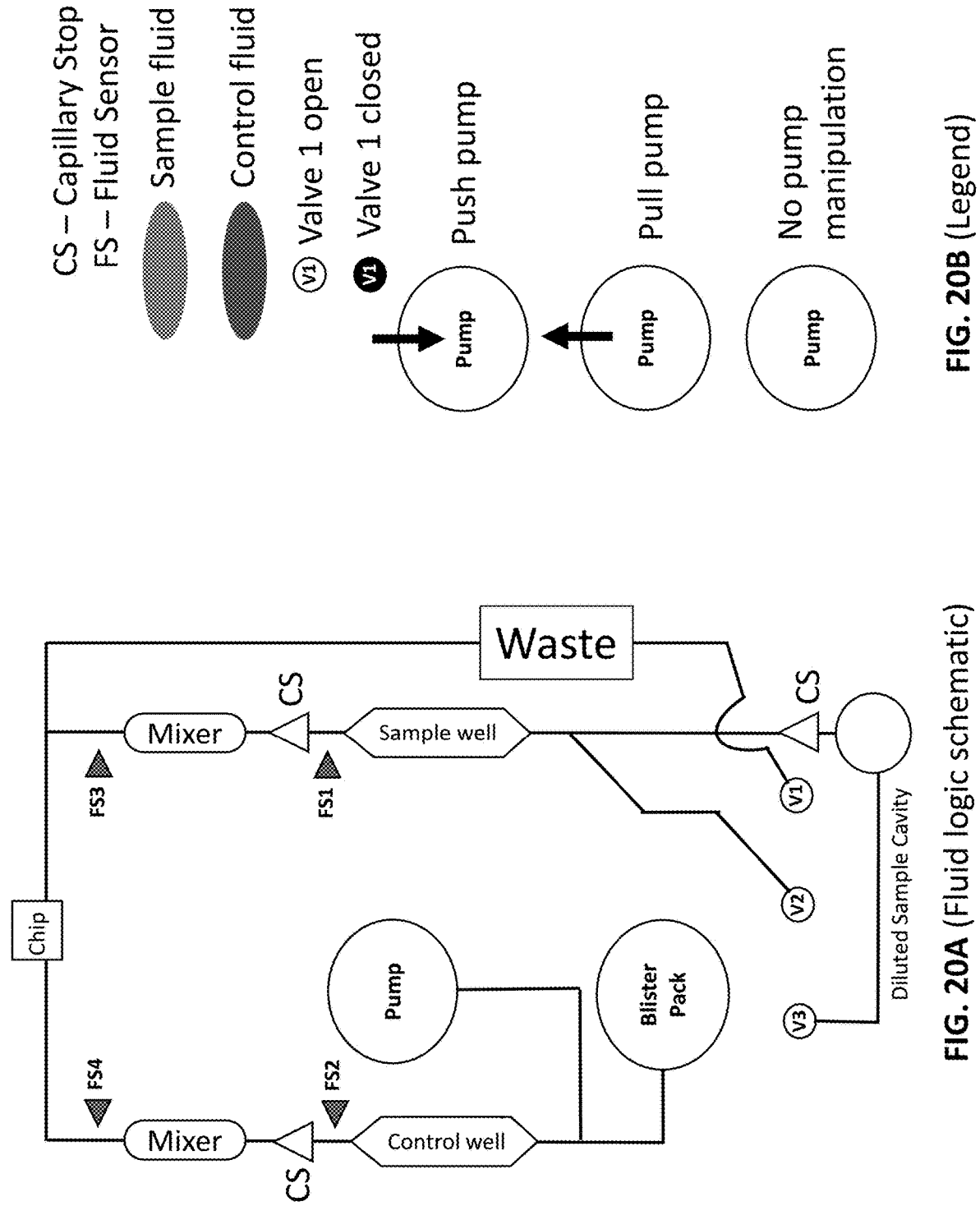
FIG. 20B (Legend)
FIG. 20A (Fluid logic schematic)

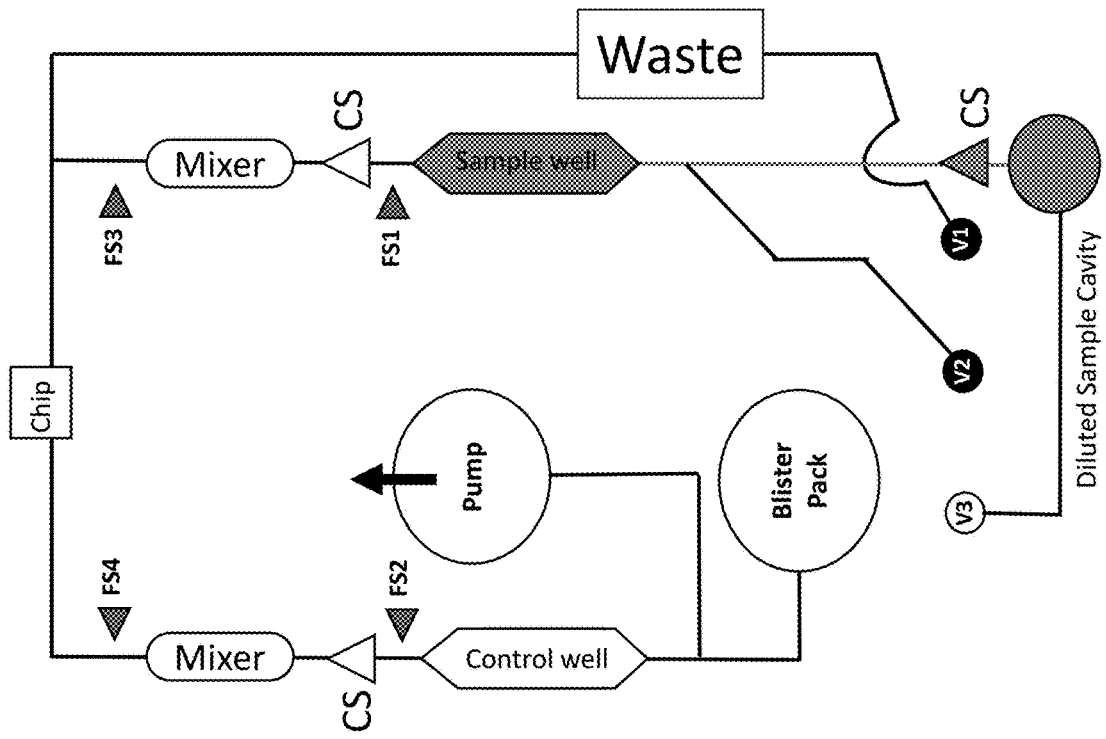
FIG. 20D (Sample Metering)
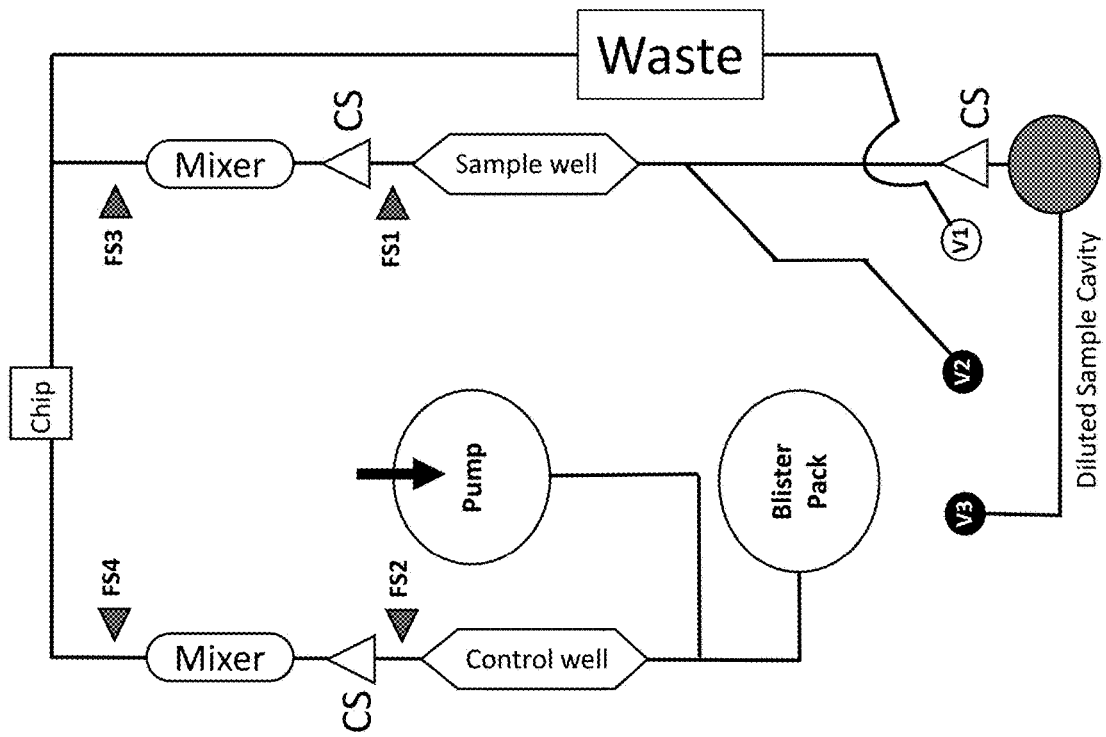
FIG. 20C (Prime pump)

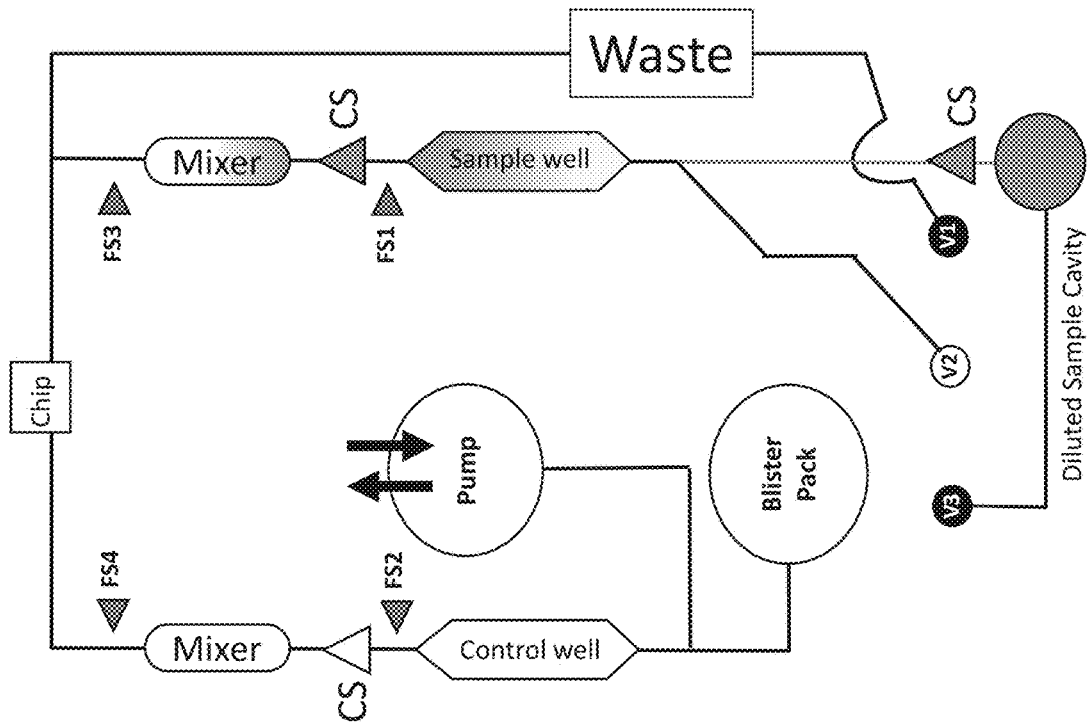
FIG. 20F (Mix)
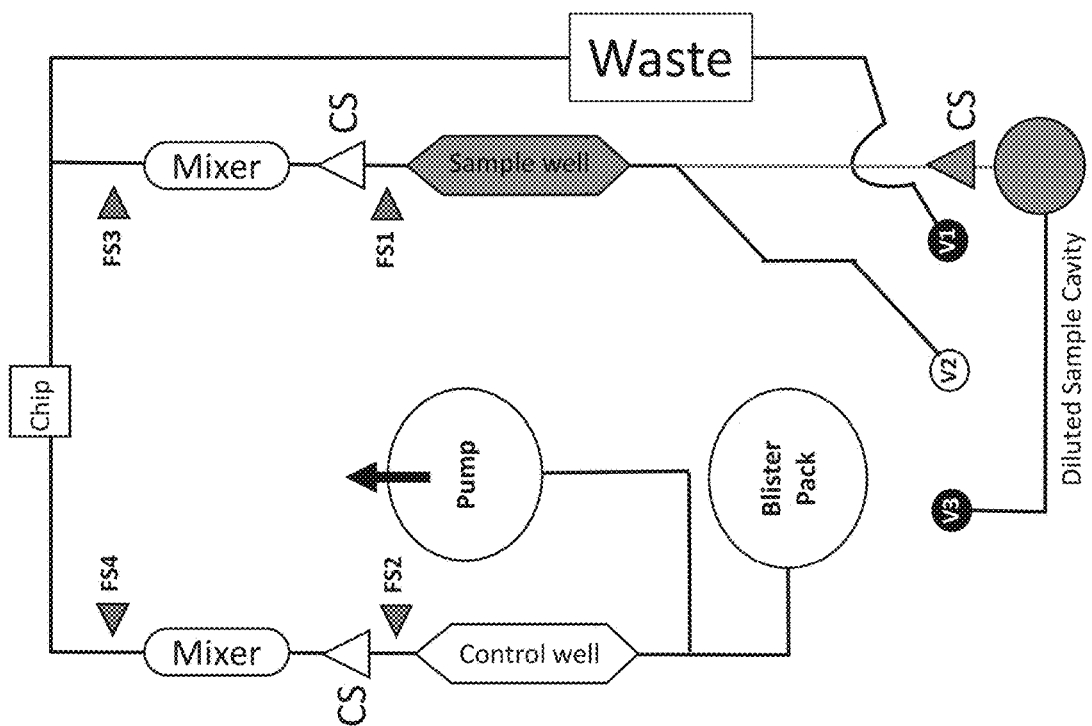
FIG. 20E (Cleave)

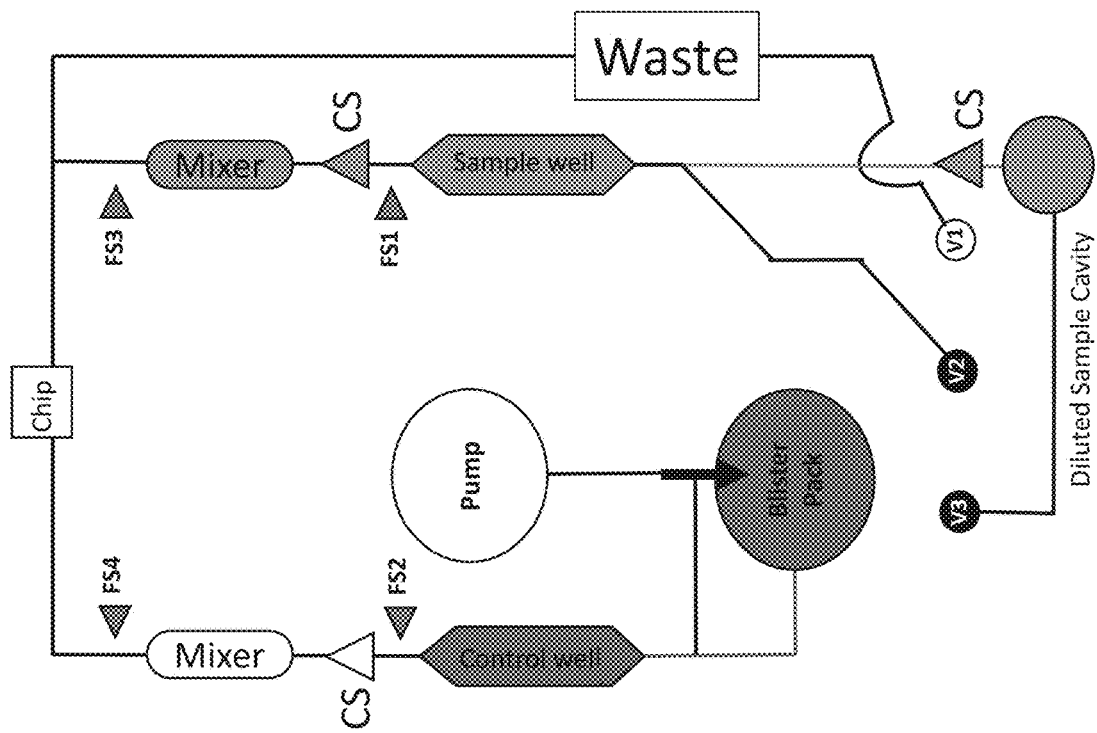
FIG. 20H (meter control)
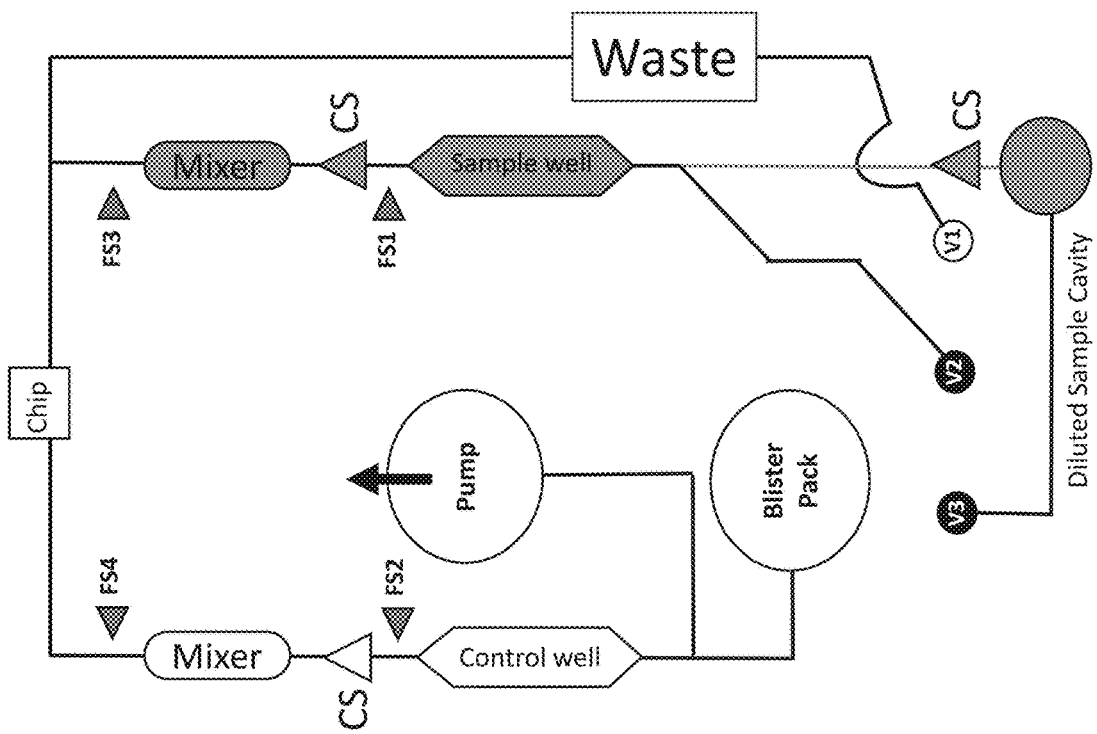
FIG. 20G (release pump)

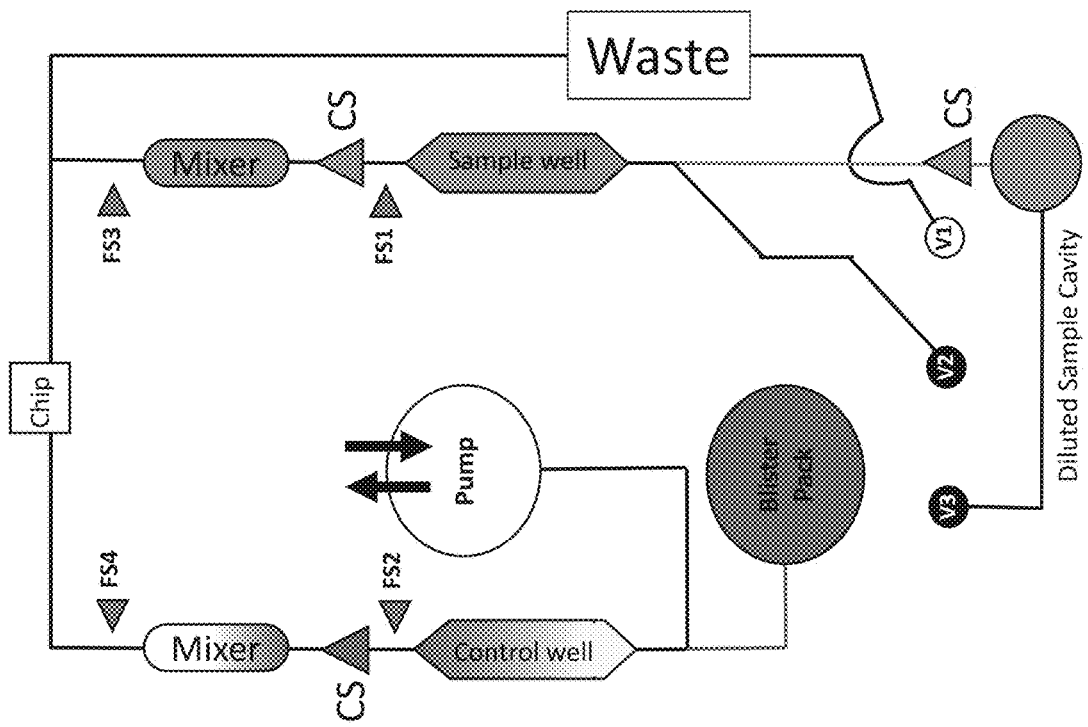
FIG. 20J (mix control)
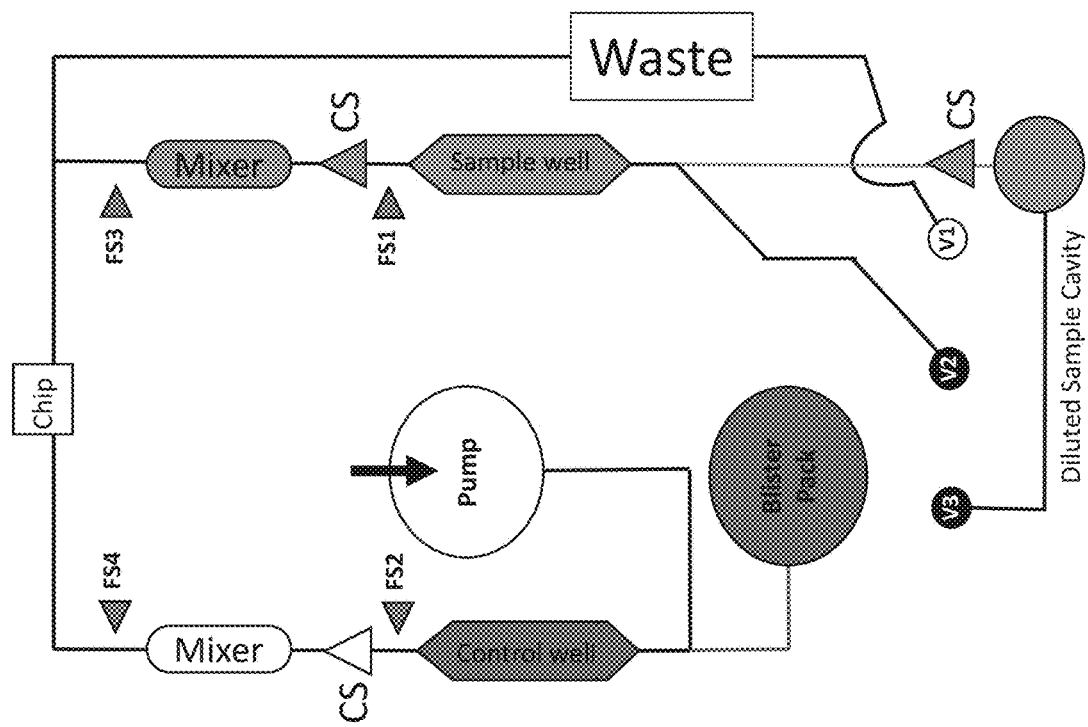
FIG. 20I (cleave control)

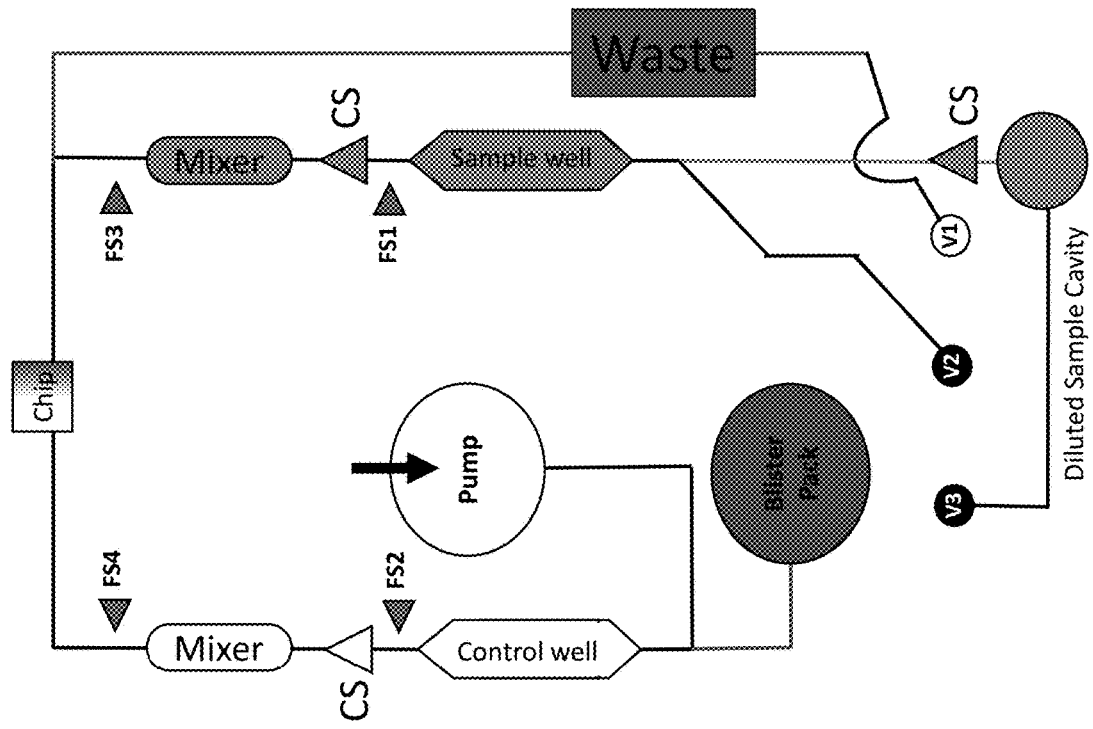
FIG. 20L (Empty control)
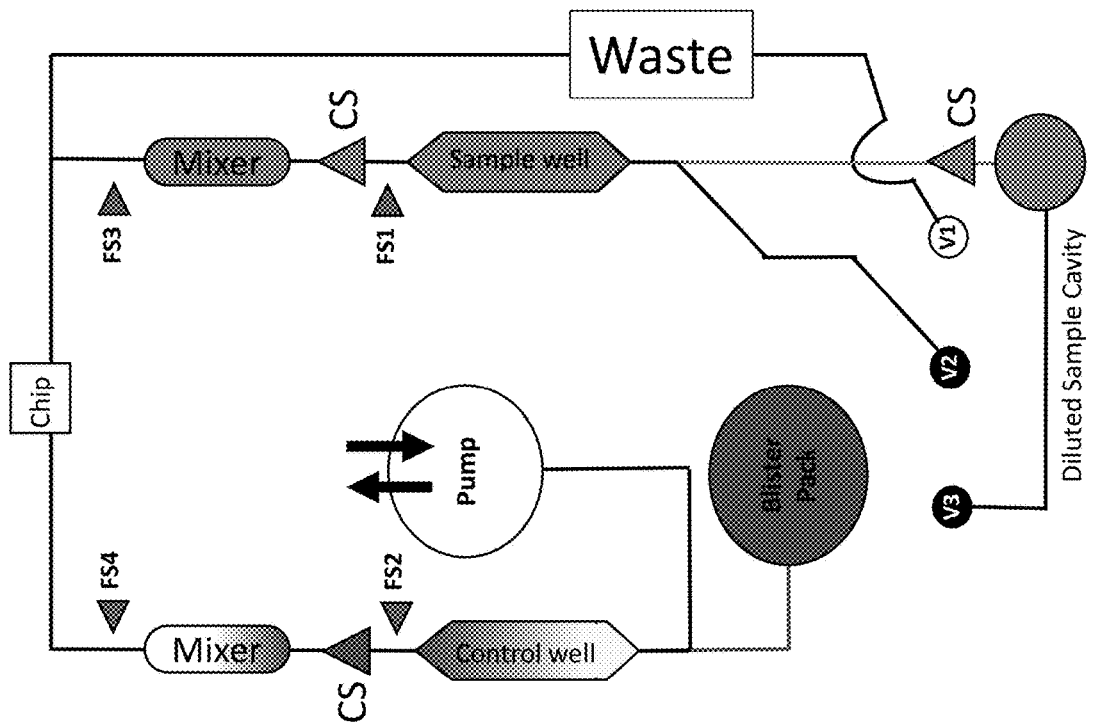
FIG. 20K (test control)

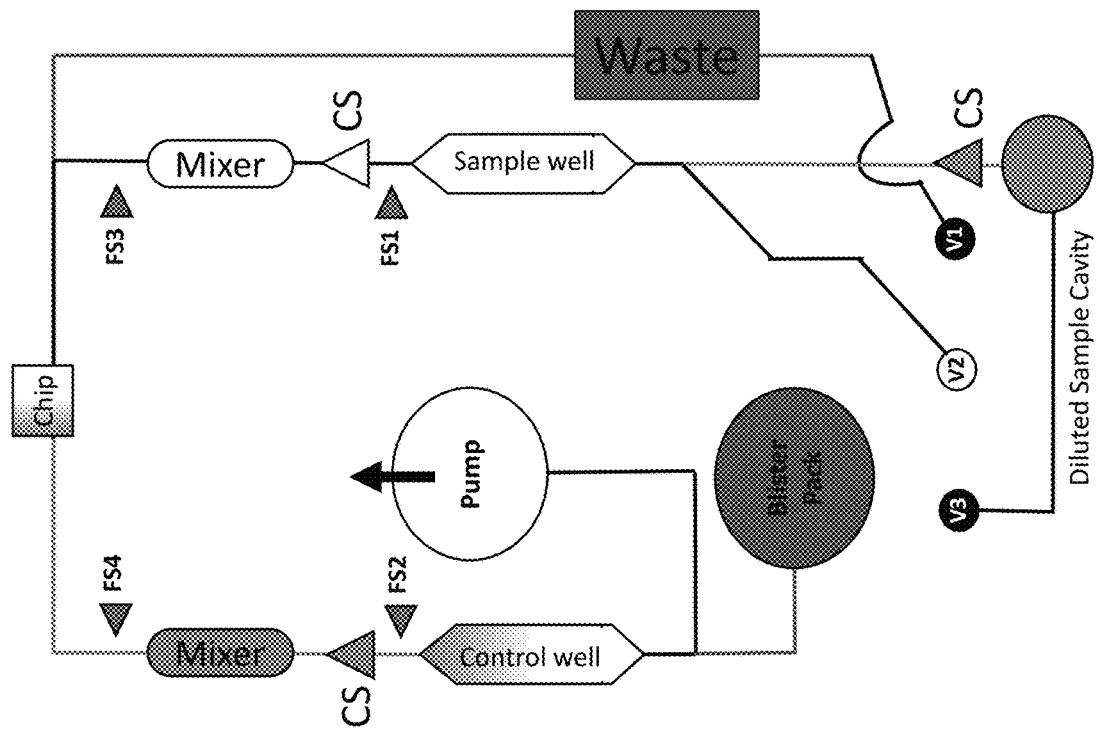
FIG. 20N (Empty sample)
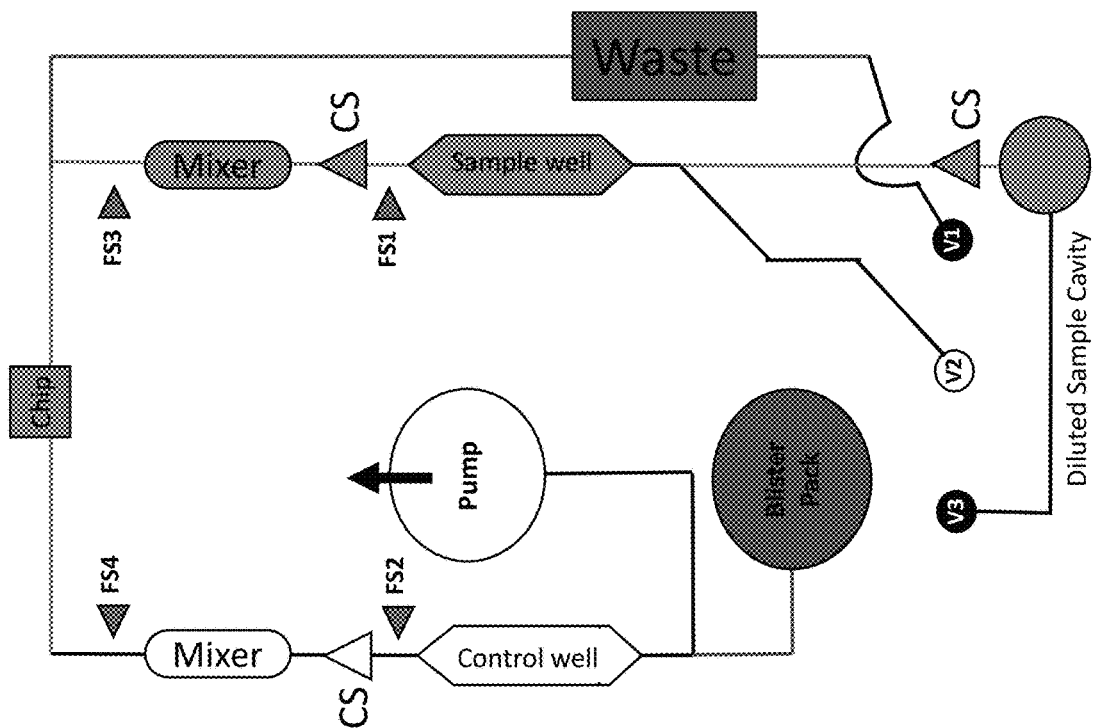
FIG. 20M (test sample)

CARTRIDGES FOR ORAL FLUID ANALYSIS AND METHODS OF USE

CROSS REFERENCE TO RELATED APPLICATIONS

This patent application claims priority to U.S. Provisional Patent Application No. 62/534,394, titled "ORAL FLUID ANALYZING SYSTEMS AND METHODS" and filed Jul. 19, 2017, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Embodiments of the invention relate generally to analyte collection and testing systems and methods, and more particularly to disposable oral fluid collection and testing systems and methods.

BACKGROUND

Detection of analytes, particularly for drugs of abuse, is important in various workplace drug testing settings, such as for pilots, professional athletes, and law enforcement, and to detect driving under the influence of drugs (DUID). Detection of these analytes in oral fluid, i.e., saliva, provides a more convenient method of sample collection than collection of blood or urine.

Conventionally, the collected samples are sent to a certified testing laboratory for analysis. However, sending the samples to the lab and then waiting for the lab to process and testing the sample and then report the results can take a significant amount of time, typically at least days. In many situations, it would be desirable to have testing results at the point of testing instead of waiting days for results from the lab. This would allow, for example, the airline to prevent pilots under the influence of drugs to fly a plane, thereby improving safety.

Therefore, it would be desirable to provide a system and method for providing point of test testing using oral fluids that provides testing results on site shortly after the sample has been collected.

SUMMARY OF THE DISCLOSURE

Described herein are biological sample collection and testing apparatuses (including devices and systems, such a saliva collection systems or subsystems, cartridges, and/or readers), and methods for using them. For example, described herein are disposable apparatuses (e.g., cartridges) for use with a reader that can handle a fluid sample without the need of manual sample preparation, and an opto-fluidic device that can run tests on a high viscosity and very low protein diffusivity fluid sample in an automated setup. The fluid sample may be saliva, or alternatively any bodily fluid (blood, lymphy, urine, interocular fluid, etc.).

The device is intended to be used for detection of analytes, such as drugs of abuse, in fluid (e.g., saliva) samples from test subjects. One of the primary purposes is for point of test detection for example, DUID or workplace drug testing.

In some variations, the apparatus may be an integrated cartridge, that may serve multiple functions including but not limited to collection of sample, dilution of sample, mixing of sample with reagent(s), sensor calibration and detection. In operation, the disposable device may be inserted into a reader (which may be hand held or desktop) which provides fluidic, electrical, and optical connection to the disposable device. The reader also may automatically control the measurement sequence without the need of operator intervention. Also described herein are sample (e.g., saliva) collection systems. These systems may include a body portion and a cap portion that may be separate initially but may be operated together. In some variations the fluid collection system may be part of a cartridge that may also include microfluidic processing components, as described herein. Although many of the examples described herein show these components operating together, it should be understood that they may be separate or separable. For example, a fluid (e.g., saliva) collection system may be separate from the cartridge containing the microfluidics, and may find use for just reliably and accurately collecting bodily fluids. Similarly the portion containing the microfluidics (e.g., photonic/optical chip, mixing channels, pump/diaphragm, etc.) may be separate from the fluid collection system or may be integrated with it.

Thus, in some variations the device (which may be disposable) has two parts, a collection system (fluid/saliva collection system) and a cartridge. As mentioned, the two parts may be used independently or the device may be integrated in form. For simplicity in this description, the term "cartridge" may refer to an integrated cartridge, including the fluid collection system.

The collection system may be a saliva collection system that collects saliva samples from the test subject. Two samples may be collected simultaneously. A cap may be placed over the collection body of the collection system which may isolate the two samples. One sample may be stored in a preservative solution for confirmatory test by forensic lab while the other sample may be mixed with a dilution buffer and used for the rapid testing on site. Critically, the apparatus is configured so that a precise dilution and accurate mixing may be automatically performed by the saliva collection system, and the second (confirmation) sample, may be securely stored in a tamper-evident and/or resistant manner.

In one embodiment the collection device is integrated into the cartridge body itself. The collection device dilutes the rapid test sample and transfers it into the cartridge.

The cartridge may include a fluidic section made of microchannels, fluid wells and vents, and a photonic chip for detection of analytes such as drugs in the diluted saliva. The photonic chip may include a plurality of waveguides that may be configured for evanescent detection of one or more analytes (e.g., drugs) from the fluid sample. Examples of photonic chips are described, for example, in U.S. Pat. Nos. 8,288,157; 8,675,199; 9,423,397; and 9,528,939; U.S. Patent Publication Nos. 2016/0033412 and 2017/0023477; and International Patent Publication No. WO2016/138427 and WO2017/059425, each of which is incorporated by reference in its entirety. The chip may be a detection component. The fluidic path typically brings the diluted sample (e.g., saliva) over the chip which allows for detection of the analytes such as drugs in the sample in an accurate manner.

The cartridge may include push/pull pumping system to drive fluid in the cartridge in both forward and/or reverse directions. This pumping subsystem may be an elastomeric membrane that may be actuated in a single (push) direction, and may automatically expand back to the neutral position, allowing easy and accurate actuation by a reader, which may include a single piston that may simply push against the diaphragm (e.g., elastomeric diaphragm) to drive pushing/pulling of fluid, which allows controlled movement of the fluids within the fluidic channels of the cartridge. The cartridge may also have a blister pack filled with a control fluid which may be burst when required. Other fluid releasing mechanisms may be used (e.g., metered/valved wells, wax-sealed wells, etc.). Upon bursting the blister pack may releases the control fluid into another part of the fluidic circuit. The control fluid may be used for performing assays, as will be described in greater detail herein, including single well normalization (e.g., see, e.g., WO2017/059425).

A diluted saliva sample may be stored in the diluted sample cavity. A metered volume of diluted saliva may be moved into the sample metering well. The sample may be metered accurately to ensure test result accuracy.

The sample metering may have one or more preloaded agents, including, e.g., a lyophilised material (e.g., bead, pellet, etc.) which dissolves in the diluted saliva and/or control fluid. In some variations, the agent ("detection agent") is configured to bind to an analyte to be tested, and may be directly conjugated to an indicator, or indirectly conjugated. For example, the agent may include antibodies tagged with fluorophores; the antibodies may bind one or more drug molecules (e.g., exemplary analytes) and allow for detection of the analyte in the fluid sample.

In general, the components, including the preloaded agents, may need to be well mixed and incubated with the sample and/or control fluids. For example, the dissolved detection agent (e.g., proteins such as antibodies) may be mixed thoroughly to ensure uniform concentration within the metered volume of sample. This may be achieved by moving the sample through a fluidic mixer in the fluidic circuit. Surprisingly, the methods and apparatuses described herein have identified rapid and effective fluid mixing by pushing and pulling the fluid through a serpentine mixer path, as will be described in greater detail herein.

The dissolving and mixing of the detection agent(s) in the diluted sample may complete the sample preparation and may provide the final analyte for testing. The analyte may then be moved within the channels and brought over the sensing area of the chip and the reader measures the drugs in the analyte based on the reaction characteristics.

Sample testing may begin with collecting saliva from a test subject by inserting the swab piston(s) of the collection device into the subject's mouth and, in some variations, under the tongue to stimulate saliva generation. Once sufficient saliva has been collected, a cap may be placed over the swabs to isolate the confirmatory and rapid test samples. In addition, the cap may contain a dilution solution and a preservative solution, separately, that may be automatically and precisely mixed with the collected samples upon securing the cap to the collection body of the collection system; the force of attaching the cap may be transferred to dilute, mix, and dispense the sample.

For example, a saliva sample for a rapid test may be diluted and transferred into the cartridge from the saliva collection subsystem. This can be accomplished by insertion of the swab pistons into the cap, which contains the solutions (e.g., dilution fluid and preservation solution) to force the dilution fluid into the swab. The cartridge with sample may be inserted into a reader which may manipulate the cartridge to automatically meter, dispense and test. For example, a predefined amount of diluted sample can then be metered into a sample metering well, which may contain the testing reagents (e.g., a lyophilized material). In some variations, the lyophilized material can dissolve in the metered diluted saliva sample. The metered diluted saliva sample may be mixed so that the dissolved proteins in the sample and/or from the dissolved bead achieve a uniform concentration and distribution throughout the entire sample. After mixing, the sample may be held stationary for a set or predetermined duration, which serves as the incubation period.

Next, the control solution may be dispensed and metered into the cartridge. For example, a blister pack in the cartridge may be pierced (e.g., by the reader) to release control fluid into the fluid channels, and a known amount of control fluid is metered into the control metering well, which may also contain a lyophilized bead with testing reagents. The lyophilized bead can dissolve in the metered control fluid. The control fluid may be mixed so that the dissolved proteins in the control fluid and/or from the dissolved bead achieve uniform concentration and distribution through the control sample. After mixing, the control fluid may be held stationary for a set or predetermined duration, which serves as the incubation period.

The control fluid may be moved over the chip and measurements are taken by the reader. The control fluid may then be moved into a waste reservoir to free the chip so that the diluted saliva sample can be moved over the chip and measurements can be taken. The diluted saliva sample can then be moved into another waste reservoir. This completes on site point of test testing. The collected confirmatory sample can then be sent to a certified lab for confirmatory testing.

For example, described herein are bodily fluid (e.g., saliva) collection systems that may include: a collection body; a first swab piston extending distally from the collection body, the first swab piston comprising a first internal channel configured to wick fluid (e.g., saliva) from an open distal end of the first swab piston; a second swab piston extending distally from the collection body, the second swab piston comprising a second internal channel configured to wick fluid (e.g., saliva) from an open distal end of the second swab piston; a diluted sample cavity in fluid connection with a proximal end of the first internal channel; and a cap having a first tube configured to receive the first swab piston and a second tube configured to receive the second channel piston; a dilution buffer within the first tube and covered by a first frangible cover that is configured to be pierced by the first swab piston when the cap is attached to the collection body; a preservation solution within the second tube and covered by a second frangible cover that is configured to be pierced by the second swab piston when the cap is attached to the collection body; and a fastener configured to secure the cap to the collection body.

For example, a saliva collection system may include: a collection body; a first swab piston extending distally from the collection body, the first swab piston comprising a first internal channel configured to wick saliva from an open distal end of the first swab piston; a second swab piston extending distally from the collection body, the second swab piston comprising a second internal channel configured to wick saliva from an open distal end of the second swab piston; a diluted sample cavity in fluid connection with a proximal end of the first internal channel; and a cap having a first tube configured to receive the first swab piston and a second tube configured to receive the second channel piston;

a dilution buffer within the first tube and covered by a first frangible cover that is configured to be pierced by the first swab piston when the cap is attached to the collection body; a preservation solution within the second tube and covered by a second frangible cover that is configured to be pierced by the second swab piston when the cap is attached to the collection body; and a fastener configured to secure the cap to the collection body when a predetermined amount of force is applied, wherein the first swab piston and first tube are configured so that securing the cap to the collection body drives the dilution buffer through the first internal channel to mix and dilute any saliva within the first internal channel and to push the mixed and diluted saliva into the diluted sample cavity.

In general, the force applied by the user to close the cap onto the rest of the apparatus may be used to drive mixing and dispensing of the dilution fluid in the cap in the apparatus. For example, the fastener may be configured to secure the cap to the collection body when a predetermined amount of force is applied, wherein the first swab piston and first tube are configured so that securing the cap to the collection body drives the dilution buffer through the first internal channel to mix and dilute any saliva within the first internal channel and to push the mixed and diluted saliva into the diluted sample cavity.

The first internal channel and the second internal channel may each comprise a plurality of capillaries. In some variations, the first internal channel and the second internal channel each comprise a porous swab.

The cap may generally be a separable cap that may be attached, and once attached, may be locked or secured onto the collection body. The cap may include one or more tamper indicators (e.g., dyes, etc.) showing if the cap has been separated from the body, once secured. The fastener may be configured to lock the cap to the collection body. The fastener may be configured as a snap, that provides tactile and/or audible feedback when securing, and may also be configured to have a sudden release once a threshold of force is applied, to both engage with the collection body and to drive the cap onto the collection body to mix and/or dispense.

In general, the system of claim 1, wherein the dilution buffer is different from the preservation solution and the preservation solution is configured for long-term storage of a saliva sample. For example, the preservation solution may include Acetonitrile, DimethySulphoxide (DMSO), a detergent (e.g., Triton x-100) and a pH buffer (e.g., Citrate Buffer pH 4.0).

The frangible covers may be foil covers. In some variations, the frangible covers are different parts of the same material (e.g., different regions of the foil cover). The frangible cover may be a wax coating, a plastic material, etc.

Any of these apparatuses may include seal around each of the first and second swab pistons configured to prevent the passage of fluid out of the first and second tubes of the cap when the first and second swab pistons are engaged with the first and second tubes.

Any of these apparatuses may include a colorimetric indicator on the first or second swab pistons (or both) configured to indicate a level of saliva within the first or second swab pistons, e.g., when sufficient saliva has been collected (e.g., when "full").

As mentioned above, any of these apparatuses (e.g., fluid/saliva collection systems) may be part of a cartridge that may be read by a reader. For example, the apparatus may include a reader cartridge body extending from the collection body opposite from the first and second swab pistons, wherein the cartridge body is configured for insertion into a reader. For example, the cartridge body may comprises a photonic chip comprising a plurality of waveguides having an exposed edge on one end of the cartridge body, further comprising the drug bound to a surface in optical communication one or more of the plurality of waveguides. The diluted sample cavity may be within the cartridge body. The cartridge body may comprise a metering well, a serpentine mixing channel, and a pumping diaphragm all in fluid communication with the diluted sample cavity.

Also described herein are methods of collecting saliva from a subject. The method may include: placing a first swab piston, and a second swab piston of a saliva collection system in the subject's mouth, wherein the first and second swab pistons extend distally from a collection body; wicking saliva from the subject's mouth into a first internal channel within the first swab piston and into a second internal channel within the second swab piston; removing the first and second swab pistons from the subject's mouth; inserting a cap over the first and second swab pistons, so that the first swab piston is inserted into a first tube in the cap to pierce a first cover that covers a dilution buffer and so that the second swab piston is inserted into a second tube in the cap to pierce a second cover that covers a preservation solution; and fastening the cap to the collection body, wherein a force of fastening the cap to the collection body drives the dilution buffer through the first internal channel to mix and dilute saliva within the first internal channel and to push the mixed and diluted saliva into a diluted sample cavity; testing the diluted saliva from the diluted sample cavity in a reader device; and storing the saliva collection system with saliva from the second swab piston for later processing.

Placing the first and second swab pistons may comprise placing the first and second swab pistons under the subject's tongue. Removing the first and second swab pistons may comprise removing the first and second swab pistons after a colorimetric indicator on the first or second swab pistons changes color to indicate a level of saliva collected. Fastening the cap may comprise snapping the cap onto the collection body.

Inserting the cap may comprise engaging a seal around the first swab piston with the first tube to prevent leakage of the dilution buffer and engaging the seal around the second swab piston with second tubes to prevent leakage of the preservation solution. Fastening the cap to the collection body may comprise locking the cap to the collection body so that the cap may not be removed without damaging the saliva collection system.

Testing the diluted saliva from the diluted sample cavity may comprise inserting a cartridge body extending proximally from the collection body into a reader device. In some variations, inserting the cartridge body into the reader device may comprise inserting the cartridge body so that: an outer edge of a photonic chip in the cartridge body is aligned with an optical sensor in the reader device, a piston in the reader device aligns with a diaphragm on the cartridge, and a plurality of openings (e.g., vents in fluid communication with the fluidic circuit) in the cartridge body each align with individual valves in the reader device configured to open or close the openings in the cartridge body.

Also described herein are cartridges, as mentioned above. For example, a cartridge may be configured as a cartridge for testing a subject's saliva for a drug using a reader device, and may include: a cartridge body; a photonic chip comprising a plurality of waveguides having an exposed edge on one end of the cartridge body, further comprising the drug bound to the waveguide surface; a diluted sample cavity configured to hold a diluted saliva sample; a metering channel within the cartridge body in fluid communication with the diluted sample cavity; a serpentine mixing channel in fluid communication with the metering channel at a first end and in fluid communication with the photonic chip at a second end; a plurality of openings through the cartridge body in fluid communication with the diluted sample cavity and metering channel, wherein the plurality of openings are configured to be shut by a valve on a reader device; a diaphragm in the cartridge body, the diaphragm having a neutral position, a first displaced position extending a first distance from the neutral position and a second displaced position extending a second distance from the neutral position that is greater than the first distance; and wherein displacement of the diaphragm by an external push rod on the reader device to the second distance pushes fluid through the serpentine mixing channel in a first direction and further wherein releasing the diaphragm to the neutral position pulls fluid through the serpentine mixing channel in a second direction.

In some variations, the cartridge further comprises a lyophilized and fluorescently-marked antibody in fluid communication with the metering channel. For example, the cartridge may further comprising a waste channel fluidly connected to a waste chamber and in fluid communication with the photonic chip. In some variations, the cartridge further comprises a second serpentine mixing channel in fluid communication with the photonic chip in fluid connection with a second metering channel coupled to a source of control fluid. The cartridge may further include a blister pack containing a control (e.g., buffer) solution.

In any of these variations, the cartridge may include a saliva collection system/subsystem, including a saliva collection body extending distally from the cartridge body, and configured to collect and dilute a saliva sample from the subject. The saliva collection body may comprises a first swab piston extending distally from the collection body, the first swab piston comprising a first internal channel configured to wick saliva from an open distal end of the first swab piston; and a second swab piston extending distally from the collection body, the second swab piston comprising a second internal channel configured to wick saliva from an open distal end of the second swab piston. The cartridge may also include a cap having a first tube configured to receive the first swab piston and a second tube configured to receive the second channel piston; a dilution buffer within the first tube and covered by a first frangible cover that is configured to be pierced by the first swab piston when the cap is attached to the collection body; and a preservation solution, having a different composition than the dilution buffer, within the second tube and covered by a second frangible cover that is configured to be pierced by the second swab piston when the cap is attached to the collection body. In some variations, the cartridge includes a fastener configured to secure the cap to the collection body when a predetermined amount of force is applied, wherein the first swab piston and first tube are configured so that securing the cap to the collection body drives the dilution buffer through the first internal channel to mix and dilute any saliva within the first internal channel and to push the mixed and diluted saliva into the diluted sample cavity.

The drug preloaded on the apparatus may comprise one or more drugs of addiction. For example, the drug may one or more of: cocaine, THC, an opiate (e.g., fentanyl, etc.), and benzodiazepine. The drug may be directly detected or a component or metabolite thereof may be detected.

In some variations cartridge may be configured to detect something other than the drug, such as a protein or other analyte, and therefore some amount of this protein or other analyte may be preloaded into the cartridge in place of the drug for performing the assays described herein.

For example, a cartridge for testing a subject's bodily fluid (e.g., saliva) for a drug using a reader device may include: a cartridge body; a photonic chip comprising a plurality of waveguides having an exposed edge on one end of the cartridge body, further comprising the drug bound to a surface of the photonic chip above the plurality of waveguides; a diluted sample cavity configured to hold a diluted saliva sample; a metering channel within the cartridge body in fluid communication with the diluted sample cavity; a lyophilized and fluorescently-marked antibody in fluid communication with the metering channel; a serpentine mixing channel in fluid communication with the metering channel at a first end and in fluid communication with the photonic chip at a second end; a waste channel fluidly connected to a waste chamber and in fluid communication with the photonic chip; a second serpentine mixing channel in fluid communication with the photonic chip in fluid connection with a second metering channel coupled to a source of control fluid; a plurality of openings through the cartridge body in fluid communication with the diluted sample cavity and metering channel, wherein the plurality of openings (e.g., vents in fluid communication with the fluidic circuit) are configured to be shut by a valve on a reader device; a diaphragm in the cartridge body, the diaphragm having a neutral position, a first displaced position extending a first distance from the neutral position and a second displaced position extending a second distance from the neutral position that is greater than the first distance; wherein displacement of the diaphragm by an external push rod on the reader device to the second distance pushes fluid through the serpentine mixing channel in a first direction and further wherein releasing the diaphragm to the neutral position pulls fluid through the serpentine mixing channel in a second direction.

Also described herein are method of testing a subject's saliva for a drug using any of these apparatuses. For example, the method may comprise: inserting a cartridge into a reader so that: an outer edge of a photonic chip in the cartridge is aligned with an optical sensor in the reader, a piston in the reader aligns with a diaphragm on the cartridge, and a plurality of openings in the cartridge each align with individual valves in the reader configured to open or close the openings in the cartridge; pushing, using the piston, on a diaphragm on the cartridge to displace the diaphragm from a neutral position to a first deflected position while a first opening in the cartridge is open; closing the first opening and opening a second opening in the cartridge; partially releasing the diaphragm by withdrawing the piston to pull fluid from a diluted sample cavity in the cartridge into a metering well wherein the second opening is in fluid communication with the diluted sample cavity distal to the metering well; closing the second opening and opening a third opening that is in fluid communication with a region between the metering well and the diluted sample cavity; releasing the diaphragm further by further withdrawing the piston to pull fluid into the metering well and to introduce air between the metering well and the diluted sample cavity; alternatively pushing and releasing the piston to push and pull fluid from the metering well within a serpentine mixing channel in fluid communication with the mixing well; releasing the piston to pull the fluid from the serpentine mixing channel onto a surface of the photonic chip; and reading an evanescent optical signal from a waveguide of the photonic chip.

Also described herein are systems that may include the bodily fluid (e.g., saliva) collection subsystem, the cartridge (which may be integral/integrated with and/or connectable to the bodily fluid collection subsystem) and a reader configured to read the drive and control testing in the cartridge and/or detect the output from the photonic chip (sensing chip). For example, a system for collecting and processing a biological fluid (e.g., oral fluid) may include: a bodily fluid (e.g., saliva) collection device comprising a first collection swab configured to collect oral fluid; a second collection swab configured to collect oral fluid; a cap with a first compartment sized and shaped to receive the first collection swab, and a second compartment sized and shaped to receive the second collection swab; a first dilution buffer disposed in the first compartment, wherein the first dilution buffer is configured to be mixed with the oral fluid collected by the first collection swab to form a diluted oral fluid; and a second dilution buffer disposed in the second compartment; and a cartridge for processing the diluted oral fluid sample, the cartridge comprising: a fluidic circuit comprising: a plurality of microchannels; a sample metering well in fluid communication with the plurality of microchannels, the sample metering well configured to meter out a predetermined or set volume of diluted oral fluid; and a passive mixer in fluid communication with the sample metering well, the passive mixer configured to mix the diluted oral fluid; a collection swab interface in fluid communication with the fluidic circuit and configured to receive the oral fluid collection device, wherein the first collection swab is in fluid communication with the fluidic circuit when the collection swab interface receives the first collection swab; and a reader interface in fluid communication with the fluidic circuit, the reader interface comprising: a sensing chip comprising a plurality of sensing sites in fluid communication with the fluidic circuit; and an alignment feature configured to align the sensing chip with an optical reader when the cartridge is inserted into the optical reader.

Any of the apparatuses described herein may include a reader that includes a holder for a cartridge; one or more cartridge alignment pins (e.g., for mating with and aligning to openings on the cartridge), an optical source (e.g., laser, LED, etc.) and optical detector (e.g. photodiode, CCD, etc.) that may be aligned in at least two dimensions with the edge of the photonic chip on an end of the cartridge when the cartridge is inserted into the reader. The reader may also include one or more pistons configured to controllably extend and retract to apply pushing force to the pump (e.g., a diaphragm and/or elastomeric membrane) to push and pull fluid within the cartridge; in some variations a separate piston may be configured to push on the control solution container (e.g., blister pack, etc.). The reader may also include one or more (e.g., three or more, four or more, etc.) separately addressable valves for controllably opening/closing openings on the cartridge. The valves may cover (occlude) the opening or expose it to air, to coordinate with the piston driving the pump (the pump piston of the reader). In any of the apparatuses described herein one or more fluid sensors may also be included in the reader for detecting fluid at various positions within the cartridge (e.g., before and/or after the mixing regions, e.g., the serpentine mixing regions). Thus the cartridge may have one or more windows to facilitate visualization of a meniscus from the fluid channels within the cartridge that may be aligned and detected by the fluid sensor(s). The fluid sensors may include an emitter (e.g., LED emitter) and detector for detecting the meniscus.

Any of the readers described herein may also include one or more processors (controllers) including a memory, and control circuitry, for controlling the pump piston, the valves, the fluid sensors, and the optical illumination source and optical detector for reading from the photonics chip, as well as hardware, software and/or firmware for processing signals from the photonics chip. The reader may also include one or more outputs (displays, memory, wireless or wired transmitters, printers, removable memory, etc.).

In some variations, a system for collecting and processing bodily fluids such as saliva may include: a fluid (e.g., an oral fluid such as saliva) collection device comprising: a first collection swab configured to collect bodily fluid; a cap with a first compartment sized and shaped to receive the first collection swab; a first dilution buffer disposed in the first compartment, wherein the first dilution buffer is configured to be mixed with the bodily fluid collected by the first collection swab to form a diluted bodily fluid; and a cartridge for processing the diluted bodily fluid sample, the cartridge comprising: a fluidic circuit comprising: a plurality of microchannels; a sample metering well in fluid communication with the plurality of microchannels, the sample metering well configured to meter out a predetermined or set volume of diluted bodily fluid; and a passive mixer in fluid communication with the sample metering well, the passive mixer configured to mix the diluted bodily fluid; a collection swab interface in fluid communication with the fluidic circuit and configured to receive the bodily fluid collection device, wherein the first collection swab is in fluid communication with the fluidic circuit when the collection swab interface receives the first collection swab; and a reader interface in fluid communication with the fluidic circuit, the reader interface comprising: a sensing chip (e.g., photonic chip) comprising a plurality of sensing sites in fluid communication with the fluidic circuit; and an alignment feature configured to align the sensing chip with an optical reader when the cartridge is inserted into the optical reader.

As mentioned above, the fluids (e.g., dilution fluid and/or preservation solution) within the cap may be sealed with a frangible (e.g., breakable, pierceable or removable) seal that may be ruptured or removed by the swap portions (e.g., the swab plungers, collection swabs, etc.). For example, the frangible, pierceable and/or removable seal may be made of foil. The swab portions typically include a material for wicking (drawing in) the bodily fluid into the apparatus passively. For example the swab portions may be made of a porous material, a plurality of capillary channels, a wicking material, etc. In some variations the swab portion comprises at least 5 capillary channels (e.g., at least 7 capillary channels, at least 10 capillary channels, etc.).

In general, the first and second swab pistons may include a swab material that may be held within a swab holder portion of the swab piston. The swap holder portions may be tubes or may include a tubular region, and may typically be shaped and sized to fit at least partially into the first or second compartments ("tubes") in the cap; the first or second compartments may be tubes or may include tubular regions having an inner diameter (ID) that is just slightly larger than the OD of the swab piston, and the same slide or smaller than the outer diameter OD of a seal (e.g., gasket, etc.) around the swab piston(s). For example, the seal may be an O-ring or elastomeric lip that is configured to form a seal with the first compartment (tube) and the second compartment (tube) when the first swab piston and the second swab piston are inserted As mentioned, any of the cartridges described herein may include a passive mixer comprising a serpentine channel to allow fluid to be mixed by pushing and pulling the fluid within the serpentine channel. The serpentine channel may have a sinuous shape (e.g., turning back and forth on itself, as a series of connected "s" shapes). The serpentine channel may, for example, include a microchannel having an inner diameter greater than 100 µm (e.g., between about 100 µm and about 2 mm, between about 100 µm and about 1 mm, between about 100 µm and about 900 µm, between about 100 µm and about 800 µm, between about 100 µm and about 700 µm, between about 100 µm and about 600 µm, between about 100 µm and about 500 µm, between about 100 µm and about 400 µm, between about 100 µm and about 300 µm, between about 100 µm and about 200 µm, between about 100 µm and about 150 um, etc.).

Any of the fluidic channels within the apparatuses (e.g., cartridges) described herein may include one or more capillary stops configured to prevent fluid from passing through the stop by capillary action (e.g., requiring pushing/pulling from the on-board pump, instead). For example, any of these apparatuses may include a capillary stop configured to as regions in which the inner diameter of the channel increases by 1.2×, or more (e.g., 1.5×, 2×, 2.5×, 3×, etc.). In some variations a capillary stop may be located on one or both sides of the sample well (e.g., the metering well), and/or between the metering well and the mixing region, and/or between the metering well and the diluted sample cavity.

Any of the cartridges described herein may include a waste channel and a waste well. As mentioned above, any of the cartridges described herein may include one or more vents in fluid communication with the fluidic circuit (which may be referred to herein as "openings" into the fluidic circuit. The openings may be surrounded by a gasket or rim for mating with a valve in the reader; alternatively or additionally, the reader may include a gasket or rim. For example, any of these apparatuses may include one or more vents, such as a vent downstream or upstream to the to the waste well, a vent downstream or upstream the sample metering well, and a vent downstream or upstream to the sample cavity.

The apparatuses described herein may be configured to limit or prevent optical leak and/or fluidic leak, including in particular around the photonic chip. Although the reader is generally completely fluidically isolated from the cartridge, in some variations the cartridge may be sealed or secured to prevent both light and/or fluid leak. For example, sensing chip maybe disposed against an opaque material (forming a lip, rim, ledge, etc.) configured to reduce optical leakage from the sensing chip.

Any of the cartridges described herein may also include one or more alignment features, e.g., a cut out feature, configured to receive an alignment pin in the optical reader.

A method for collecting and testing a bodily fluid (e.g., an oral fluid, such as saliva) from a subject may include the steps of (though note some of these steps may be optional and omitted): collecting a first oral fluid sample and a second oral fluid sample from the subject using an integrated sample collection device and testing cartridge, the testing cartridge comprising a microfluidic circuit, a sample metering well, and an optical sensing chip; inserting the testing cartridge into an optical reader; diluting the first oral fluid sample with a dilution buffer and transferring at least a part of the diluted first oral fluid sample from the sample collection device and into the microfluidic circuit of the cartridge; metering a set or predetermined amount of diluted first oral fluid sample into the sample metering well; dissolving reagents into the diluted oral fluid sample; mixing the diluted oral fluid sample with the reagents; incubating the mixed diluted oral fluid sample with the reagents for a set or predetermined amount of time; metering a set or predetermined amount of control fluid from a control fluid reservoir in the cartridge; dissolving reagents into the control fluid; mixing the control fluid with the reagents; moving the control fluid through the microfluidic circuit to the sensing chip; measuring the control fluid for an analyte by using the optical reader to scan the sensing chip; moving the control fluid away from the sensing chip; moving the diluted oral fluid sample to the sensing chip; and measuring the diluted oral fluid sample for the analyte by using the optical reader to scan the sensing chip.

For example, a method for collecting and testing an oral fluid from a subject may include the steps of (though note some of these steps may be optional and omitted): collecting a first oral fluid sample from the subject; placing the first oral fluid sample into the testing cartridge comprising a microfluidic circuit, a sample metering well, and an optical sensing chip; inserting the testing cartridge into an optical reader; diluting the first oral fluid sample with a dilution buffer and transferring at least a part of the diluted first oral fluid sample from the sample collection device and into the microfluidic circuit of the cartridge; metering a set or predetermined amount of diluted first oral fluid sample into the sample metering well; dissolving reagents into the diluted oral fluid sample; mixing the diluted oral fluid sample with the reagents; incubating the mixed diluted oral fluid sample with the reagents for a set or predetermined amount of time; metering a set or predetermined amount of control fluid from a control fluid reservoir in the cartridge; dissolving reagents into the control fluid; mixing the control fluid with the reagents; moving the control fluid through the microfluidic circuit to the sensing chip; measuring the control fluid for an analyte by using the optical reader to scan the sensing chip; moving the control fluid away from the sensing chip; moving the diluted oral fluid sample to the sensing chip; and measuring the diluted oral fluid sample for the analyte by using the optical reader to scan the sensing chip.

Any of these methods may also include one or more of the optional steps of: collecting a second oral fluid sample from the subject, moving the control fluid back and forth during the mixing the control fluid step, moving the diluted oral fluid sample back and forth during the mixing step the diluted oral fluid sample step, moving the control fluid to a waste well, sending the second oral fluid sample to a certified testing laboratory to test second oral fluid sample for the analyte, placing the integrated sample collection device and testing cartridge in a sealable container, and/or associating a first barcode with the first oral fluid sample and associating a second barcode with the second oral fluid sample.

For example, a method for analyzing a bodily fluid from a subject may include the steps of (though note some of these steps may be optional and omitted): obtaining or having obtained a bodily fluid sample from a subject, the sample suspected of containing at least one type of analyte of interest; mixing the bodily fluid sample with a detection reagent comprising a plurality of detectably labeled populations of different antibodies, each detectably labeled population of different antibodies configured to bind one type of a plurality of different analytes of interest to thereby generate a mixed bodily fluid sample; incubating the mixed bodily fluid sample under conditions configured to bind analytes of interest from the mixed bodily fluid sample to its respective detectably labeled antibody to generate a reacted sample, wherein a detectably labeled antibody that is not bound to an analyte of interest has an available epitope; providing a control sample comprising a plurality of detectably labeled populations of different antibodies, each population configured to bind a different type of antigen corresponding to one of the analytes of interest; providing a plurality of sensing sites having a plurality of different types of antigen attached thereto wherein each of the plurality of different types of antigen correspond to a respective different analyte of interest; passing the control sample over the plurality of sensing sites to thereby conjugate the plurality of detectably labeled populations of different antibodies to their different respective type of antigen to thereby activate a plurality of detectable control signals from the plurality of detectably labeled populations of different antibodies; measuring over time the plurality of detectable signals from the plurality of detectably labeled populations of different antibodies from the plurality of sensing sites to generate a set of control measurements for each of the plurality of detectably labeled populations of different antibodies conjugated to their different respective type of antigen; moving the control sample away from the plurality of sensing sites; flowing the reacted sample over the plurality of sensing sites and conjugating the detectably labeled populations of different antibodies from the reacted sample that have available epitope to their respective antigens in the plurality of sensing sites and thereby activating a plurality of detectable sample signals; measuring over time a plurality of separately detectable signals corresponding to the plurality of different detectably labeled populations of antibodies from the plurality of sensing sites to generate a second set of measurements; and comparing the second set of measurements to the first set of measurements for each type of different detectably labeled populations of antibodies, respectively, to thereby determine a level of each analyte of interest in the bodily fluid sample.

For example, a method for analyzing a bodily fluid from a subject comprising may include the steps of (though note some of these steps may be optional and omitted): obtaining or having obtained a bodily fluid sample from a subject, the sample suspected of containing at least one type of analyte of interest; mixing the bodily fluid sample with a detection reagent comprising a detectably labeled antibody population configured to bind the analyte of interest to thereby generate a mixed bodily fluid sample; incubating the mixed bodily fluid sample under conditions configured to bind the analyte of interest to the detectably labeled antibody to generate a reacted sample, wherein a detectably labeled antibody that is not bound to the analyte of interest has an available epitope; providing a control sample comprising a detectably labeled antibody population configured to bind an antigen corresponding to the analyte of interest; providing a plurality of sensing sites having the antigen attached thereto; passing the control sample over the plurality of sensing sites to thereby conjugate detectably labeled antibody from the control sample to the attached antigen to thereby activate a detectable control signal; measuring over time detectable signal from the plurality of sensing sites to generate a first set of measurements; moving the control sample away from the plurality of sensing sites; flowing the reacted sample from the subject over the plurality of sensing sites and conjugating detectably labeled antibody having the available epitope to the antigen in the plurality of sensing sites and thereby activating a detectable sample signal from the plurality of sensing sites; measuring over time detectable signal from the plurality of sensing sites to generate a second set of measurements; and comparing the second set of measurements to the first set of measurements to thereby determine a level of first analyte in the bodily fluid sample.

The bodily fluid may comprise, for example, an oral fluid such as saliva. Any amount of bodily fluid may be collected and/or used for the assay (following dilution); for example, the bodily fluid may comprise a volume less than 0.5 mls (e.g., between about 0.05 ml and about 1 ml, between about 0.2 ml and about 0.8 ml, between about 0.1 ml and about 0.6 ml, between about 0.1 ml and about 0.5 ml, between about 0.1 ml and about 0.4 ml, between about 0.1 ml and about 0.3 ml, less than about 0.4 ml, less than about 0.3 ml, less than about 0.2 ml, less than about 0.1 ml, etc.). In some variations, the bodily fluid may comprise a volume less than 0.05 mls.

In any of these variations, at least one of the different or detectably labeled antibody comprises a fluorescently labeled antibody. In any of these variations, the detectably labeled antibody or a first of a plurality of detectably labeled antibody populations may be configured to detect a component or metabolite of a drug (e.g., cocaine, marijuana, benzodiazepine or fentanyl, etc.). In any of these variations, an antigen attached to the plurality of sensing sites may be in a non-aqueous form prior to the passing step. The plurality of sensing sites may comprise a waveguide. The amount of the antigen or of a first of the plurality of antigens attached to the plurality of sensing sites may be at least about 5 times (e.g., at least about 6×, at least about 7×, at least about 8×, at least about 9×, at least about 10×, at least about 11×, at least about 12×, at least about 15×, at least about 20×, at least about 50×, etc.) the amount of its corresponding detectably labeled antibody in the control sample. For example, the amount of the antigen or of a first from the plurality of antigens attached to the plurality of sensing sites may be at least 100 times the amount of its corresponding detectably labeled antibody in the control sample.

In any of these variations, the plurality of sensing sites may not be washed between the passing and the flowing.

In some variations, the reader may analyze the output, which may include comparing a slope of a sample curve generated from the second set of measurements to the slope of a control curve generated from the first set of measurements specific to the analyte of interest or to a first analyte of interest from the plurality of analytes of interest to thereby determine a level of the or the first analyte in the bodily fluid based on the slope difference. For example, any of these methods may include determining that the level of the analyte or of a first analyte of interest from the plurality of analytes of interest is below a set or predetermined threshold level, and/or determining that the level of the analyte or of a first analyte of interest from the plurality of analytes of interest is above a set or predetermined threshold level. Any of these methods may include displaying to a user that the level of the analyte or of a first analyte of interest from the plurality of analytes of interest is either above or below a set or predetermined threshold level, and/or determining that the level of the analyte or of a first analyte of interest from the plurality of analytes of interest is essentially undetectable (e.g., determining that the analyte or of a first analyte of interest from the plurality of analytes of interest could not be determined).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8A and 8B illustrate an embodiment of an optical chip for analyte testing.

FIG. 9A illustrates a side cross-sectional view of a portion of the cartridge and optical chip in alignment with an optical scan head of a reader device.

FIG. 13A shows a control sample containing a detectably labeled binding agent (antibody). FIG. 13B shows a test sample reacted with a detectably labeled binding agent (antibody). FIG. 13C shows antigen attached to a sensing site as it appears prior to passing a control sample, such as the control sample shown in FIG. 13A, across it. FIG. 13D shows antigen on a sensing site and a detectably labeled binding agent (antibody) from a control samples, conjugated to an antigen. FIG. 13E show a sensing site, such as the site shown in FIG. 13D, after flowing a detectably labeled sample across the sensing site.

FIGS. 19A-19B illustrate a method of operating the cartridge (including an integrated saliva collection system) to test a subject's saliva, as described herein, including both local (e.g., immediate) testing with a reader similar to that shown in FIG. 21, and confirmation testing.

FIGS. 20A shows a partial schematic of an exemplary fluidic circuit for the cartridge (which may include a saliva collection system), similar that shown in FIG. 7. FIG. 20B is a legend illustrating component part of the partial schematic.

FIGS. 20C-20N illustrate one example of method of operating an exemplary cartridge for testing a subject's saliva for one or more drugs.

DETAILED DESCRIPTION

In general, the methods and apparatuses described herein may be used for the detection of an analyte (e.g., drug, biomarker, protein, etc.) from a bodily fluid. The examples provided below are directed primarily to detection of an analyte (or multiple analytes) from a saliva sample, and in particular to the detection of one or more drugs of abuse. However, it should be understood that these methods and apparatuses may apply as well to other bodily fluids and other analytes.

For example, described herein are apparatuses that include saliva collection. These apparatuses may be concurrently collect two samples (one for acute or immediate testing and one for later validation of the acute testing). Alternatively or additionally, these apparatuses may automatically and accurately process (e.g., dilute) the saliva sample for processing. The apparatus may include a cap that is pre-loaded with one or more solution (e.g., a dilution fluid and/or a preservation solution). The apparatus may be configured so that attaching the cap exposes the saliva sample(s) to the appropriate solution, keeping the different samples isolated from each other, and may precisely mix and dispense the saliva sample with the dilution sample in a predictable manner. The apparatus may be configured so that the act of snapping the cap onto the body of the apparatus provide the mechanical energy for dispensing the dilution fluid, mixing it with the saliva sample, and dispensing the diluted and mixed saliva dilution into a diluted sample reservoir ("diluted sample cavity") where it can be further processed.

Any of these apparatuses may also be configured as a cartridge including one or more fluidic circuits that are configured to processes, in conjunction with a reader, the diluted sample. The cartridge may include, in communication with the fluidic circuit or part of the fluidic circuit, a chip (an optical chip, also referred to as a photonic chip) that includes one or more waveguides along with detection chemistry that may allow detection via evanescent field detection of the presence and/or amount of an analyte. The cartridge may be self-contained, and may include a pump (e.g., a diaphragm, elastomeric membrane, etc.) that may be driven by a driver (e.g., piston, rod, etc.) to push and pull fluid within the microfluidic circuit. The cartridge may also include a plurality of vents (opening) to atmosphere that may be opened/closed by the reader to control fluidic movement (including metering, mixing, sampling, etc.) within the cartridge.

Figure 1:
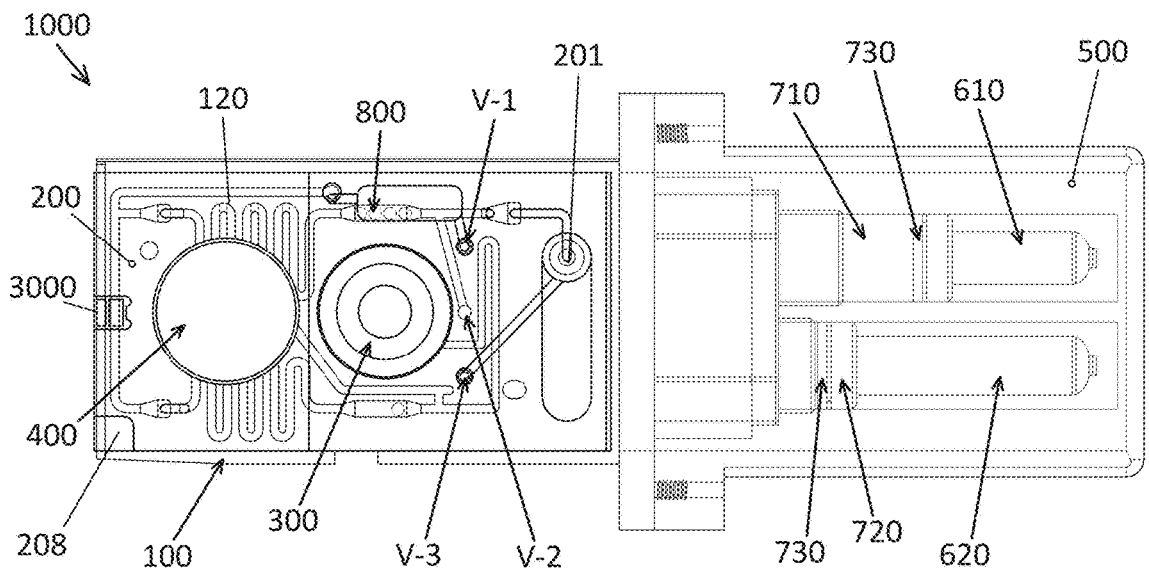
FIG. 1 is a top view of an embodiment of a disposable device that includes an integrated oral fluid collection device and cartridge for processing and testing the collected sample.
Figure 2:
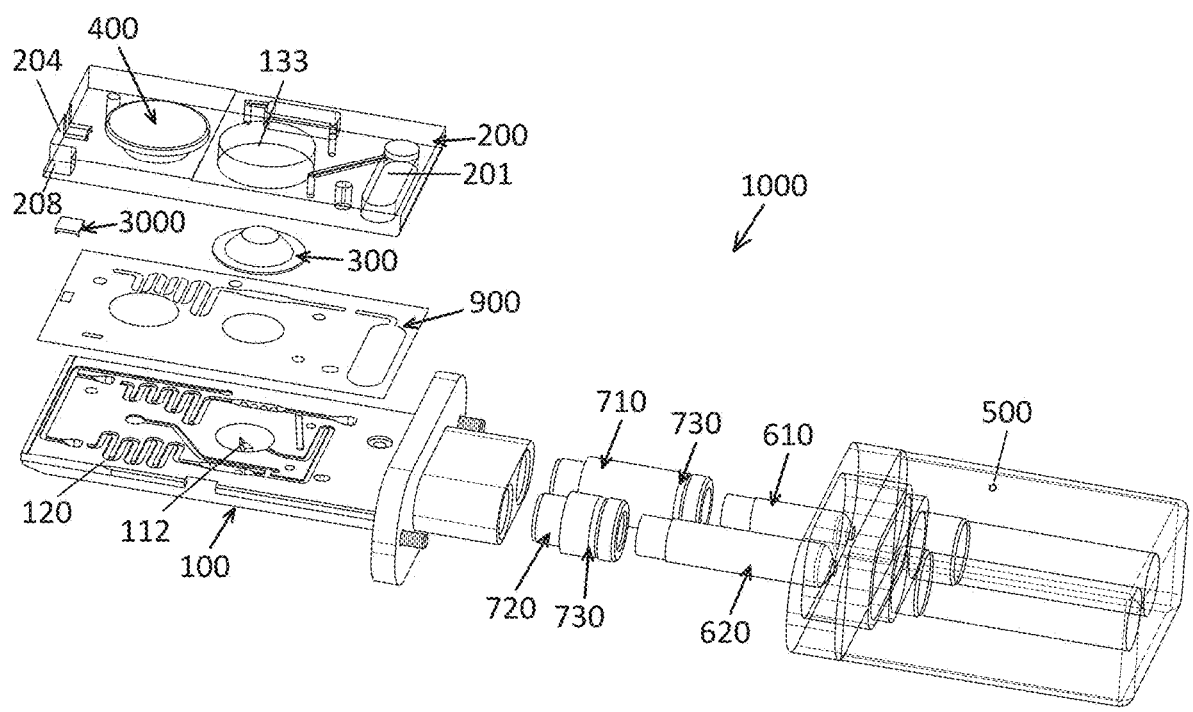
FIG. 2 is an exploded view of the components of the disposable device shown in FIG. 1.
Figure 3A:
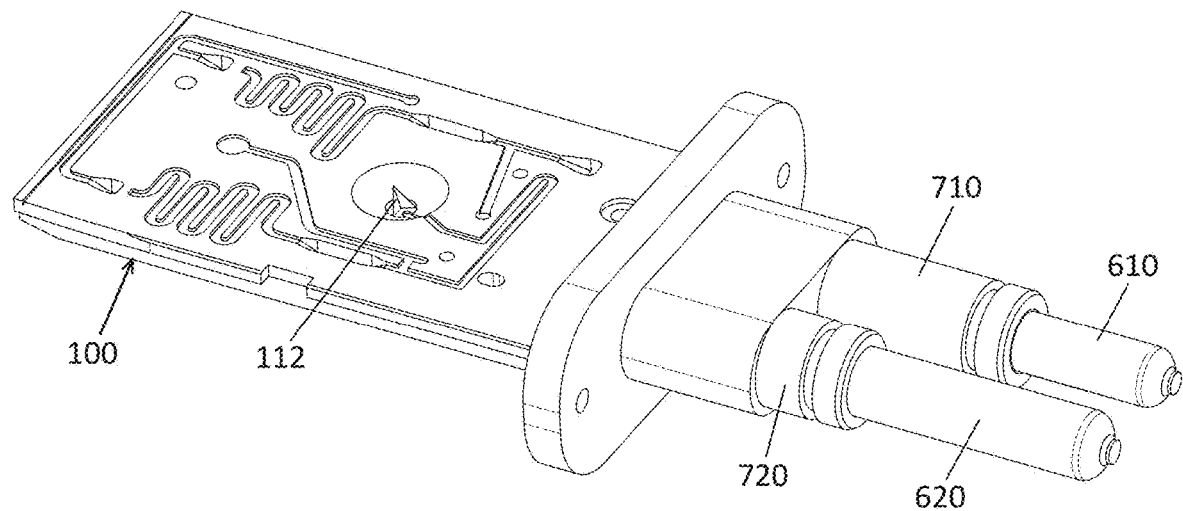
FIGS. 3A and 3B illustrate a top perspective view and bottom perspective view, respectively, of a bottom part of the cartridge attached to the saliva collection device.
Figure 3B:
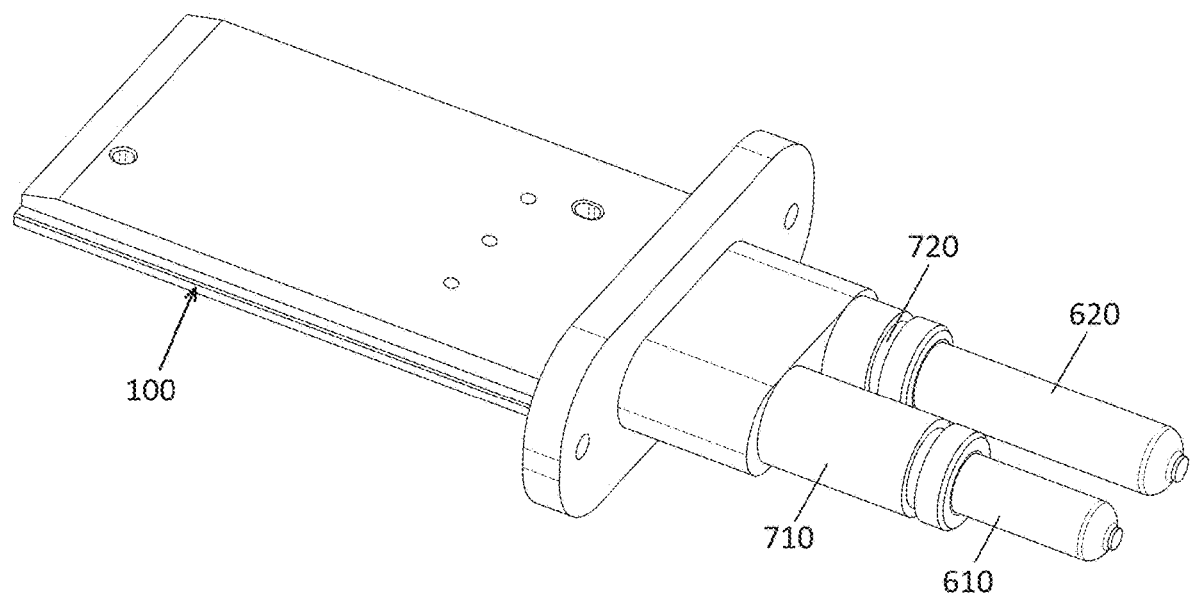

FIGS. 1 and 2 illustrate an embodiment of a disposable device 1000 for collecting, processing, and testing an oral fluid/saliva sample from a subject. After a sample has been collected, the disposable device 1000, which may be a cartridge, can be inserted into a reader for analyzing the sample. FIG. 1 illustrates the disposable device in an assembled state, while FIG. 2 illustrates an exploded view of the disposable device 1000. In one embodiment, the disposable device 1000 is constructed as an assembly of a bottom part (cartridge bottom) 100, a top part (cartridge top) 200 and a channel sealing layer 900. In one preferred embodiment, the sealing layer 900 is a double sided adhesive tape with appropriate cut-outs 902 for fluid conduits/channels that form a fluidic circuit 120. The three parts come together to form a sandwich structure with the sealing layer 900 in between bottom and top parts 100, 200. In one preferred embodiment, the top and bottom parts 100, 200 are held together by the double sided adhesive tape.

Alternatively, the sealing layer 900 can be made from a rubber or plastic sheet and held between the top and bottom part by screws, clips, rivets, bolts, or other fastening mechanisms that can be used to compress the bottom part 100 with the bottom part 200. The tightening force applied by the screws or other fastening mechanism squeezes the rubber or plastic sheet, which functions like a gasket, and provides sealing between fluid channels.

Alternatively, the sealing layer 900 can be made from a rubber sheet and held between the top and bottom part by means of heat staking or mechanical staking between the top and bottom parts. The stakes are designed to provide a mechanical force which squeezes the rubber sheet and provides sealing between fluid channels.

Alternatively, the bottom and top parts 100, 200 may be connected to each other by applying liquid adhesive in a pattern required by the fluid channels. The adhesive can also provide sealing between fluid channels.

In some embodiments, the sealing layer 900 can be a combination of the features described above, such as a rubber or plastic layer with adhesives.

In some embodiments, the cartridge top 200 and cartridge bottom 100 may be hard plastic parts that when assembled form the fluid conduits. The plastic parts may be manufactured by machining or injection moulding or vacuum forming or any other appropriate plastic manufacturing techniques.

The cartridge top 200 can have an elastomeric membrane 400 covering a cut-out in the hard plastic part. The elastomeric membrane 400 may be attached, such as by being glued, to the cartridge top 200. Alternatively, the elastomeric membrane 400 may be moulded over the hard plastic top 200 by means of over-moulding or two-shot injection moulding process. The elastomeric membrane 400 and the cavity formed by the cut-out can be in fluid communication with the fluidic channels and can function as a pump that drives fluid through the fluidic channels.

Figure 5A:
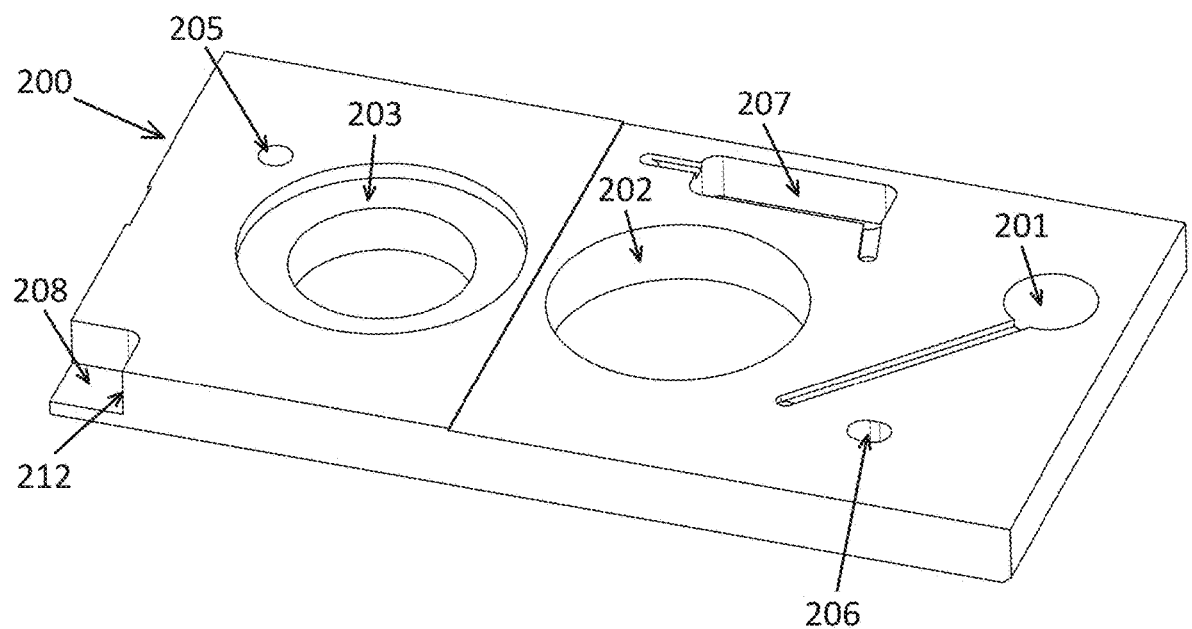
FIGS. 5A and 5B illustrate a top perspective view and a bottom perspective view, respectively, of a top part of the cartridge.
Figure 5B:
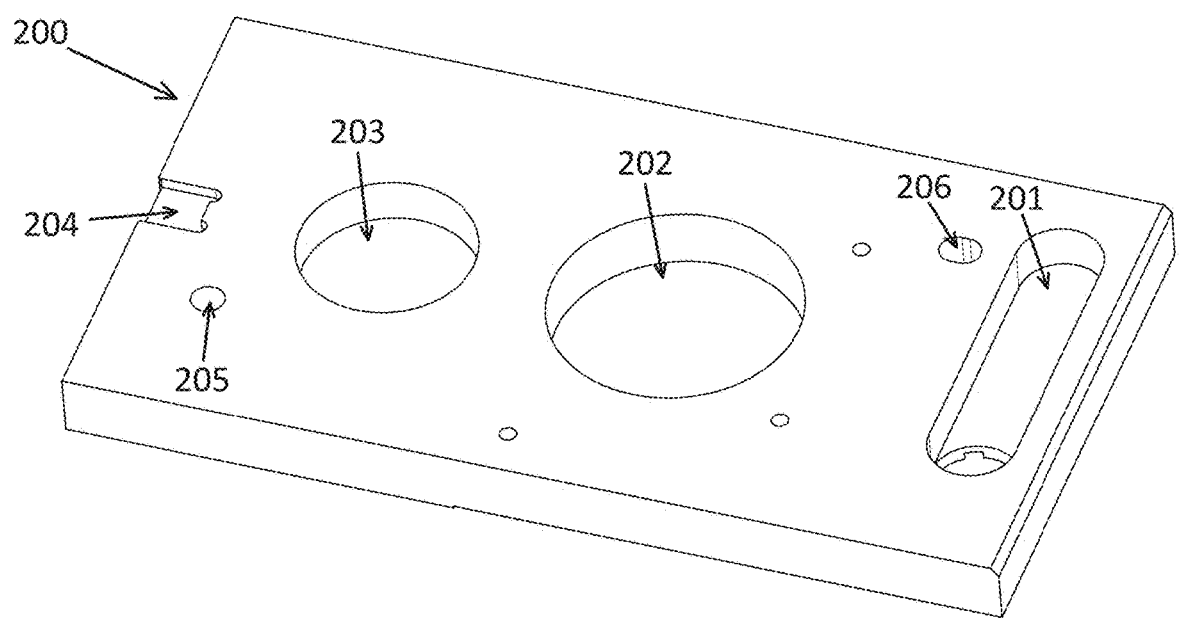
Figure 5C:
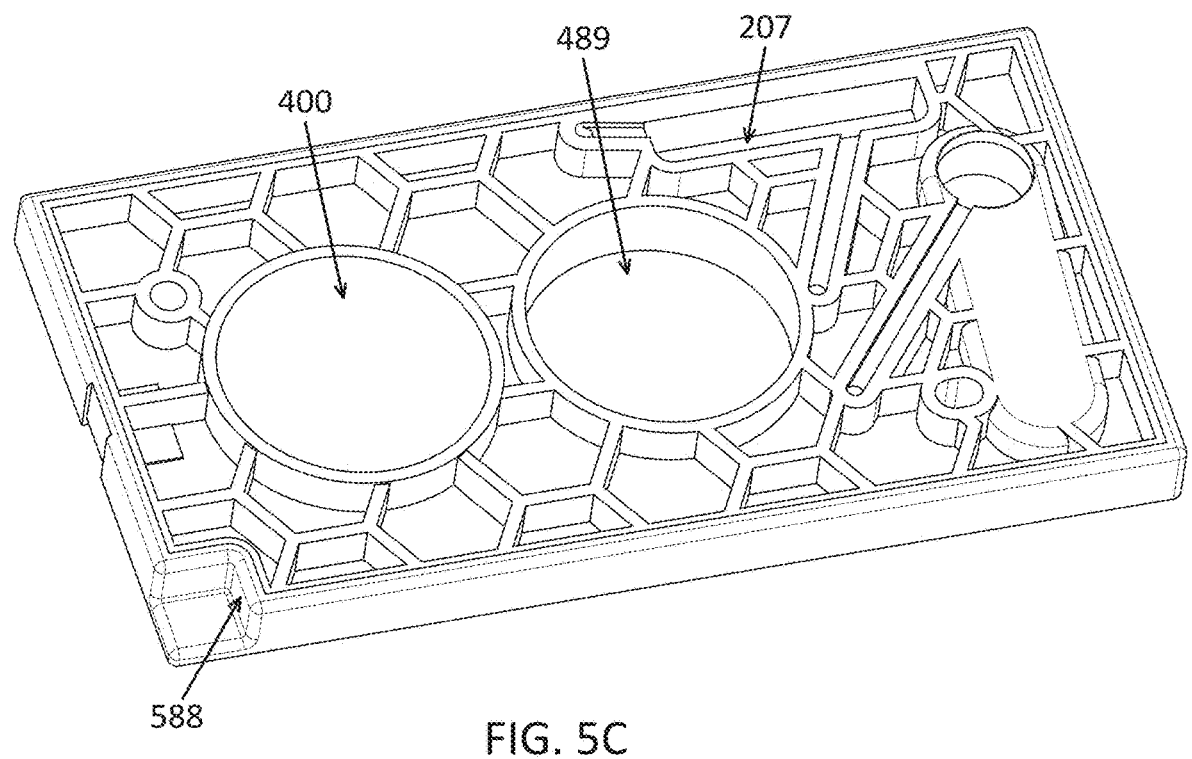
FIGS. 5C and 5D show a top and bottom, respectively, or an example of a cartridge body.
Figure 5D:
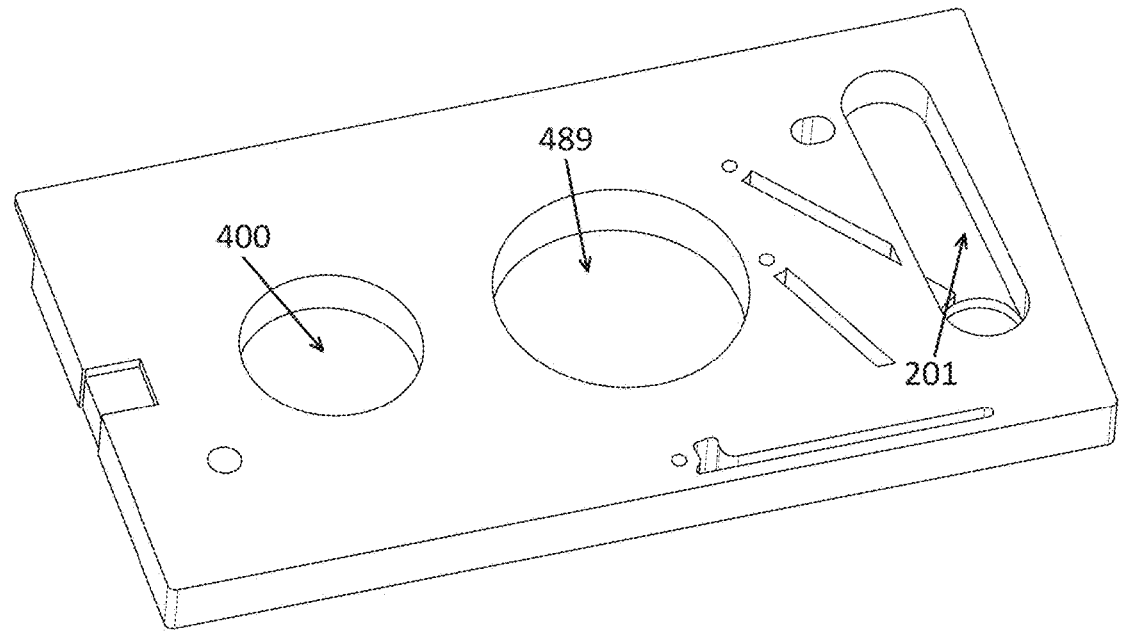

FIG. 5C shows another example of the cartridge top (shown from a bottom view, FIG. 5D shows a top view). In this example, the elastomeric diaphragm 400 (pump) is exposed on one side to allow access by the reader piston (not shown). The cartridge top may also include a waste region 207 (waste well) and may include calibration regions (e.g., z-location region 588). The cartridge top also includes an opening 489 for the blister pack. FIG. 5D also shown a sample inlet (e.g., which may be part of the diluted sample cavity/reservoir 201. The cartridge body may be made of any appropriate material, for example, a clear, transparent, medical grade polycarbonate (PC) and/or (e.g., overmolded with) a medical grade, thermoplastic elastomer (TPE), Shore 40A For example, as shown in FIGS. 1, 2, 5A, and 5B, an elastomeric membrane 400 can cover a cavity 203 in the cartridge top 200 to create a pumping well. The elastomeric membrane 400 may be pushed upon by an actuator in a reader for the disposable device 1000. As the membrane 400 is depressed into the cavity 203 it pushes the air out of the cavity 203 and into the fluid channel. The column of air pushed into the fluid channel in turn moves a slug of liquid in the fluid channel.

Reversing the direction of motion of the actuator releases the stretched membrane 400 which, owing to its elastic nature tries to return to its original shape and thus tracking the actuator as it moves. As the membrane 400 moves back to its original shape, it creates a suction in the pumping cavity 203. This suction allows movement of slug of liquid within the fluid channel in a direction opposite to the previous motion. Thus, the action of pushing on the membrane 400 and releasing it in a controlled manner allows bi-directional control over the movement of fluid within the fluid channel. As further described below particularly with respect to FIG. 7, a unique aspect of the disclosed device is the multi-channel management of fluid columns/slugs in the fluidic channels using a single on-board pumping mechanism in combination with vents placed at strategic locations.

Returning to FIGS. 1 and 2, a blister pack 300, can be assembled within the disposable device 1000. The blister pack 300 may contain buffer solution (e.g., control solution) and/or reagents used as part of the testing protocol. In one preferred embodiment, the blister pack 300 is stuck directly to a sealing layer 900 made of double sided adhesive tape. Alternatively, the blister pack 300 may be affixed to the cartridge bottom 100 or sealing layer 900 by means of an additional double sided adhesive tape placed on the blister pack 300. Alternatively, the blister pack may be glued to the cartridge bottom 100 or sealing layer 900 by means of a liquid adhesive.

Figure 4A:
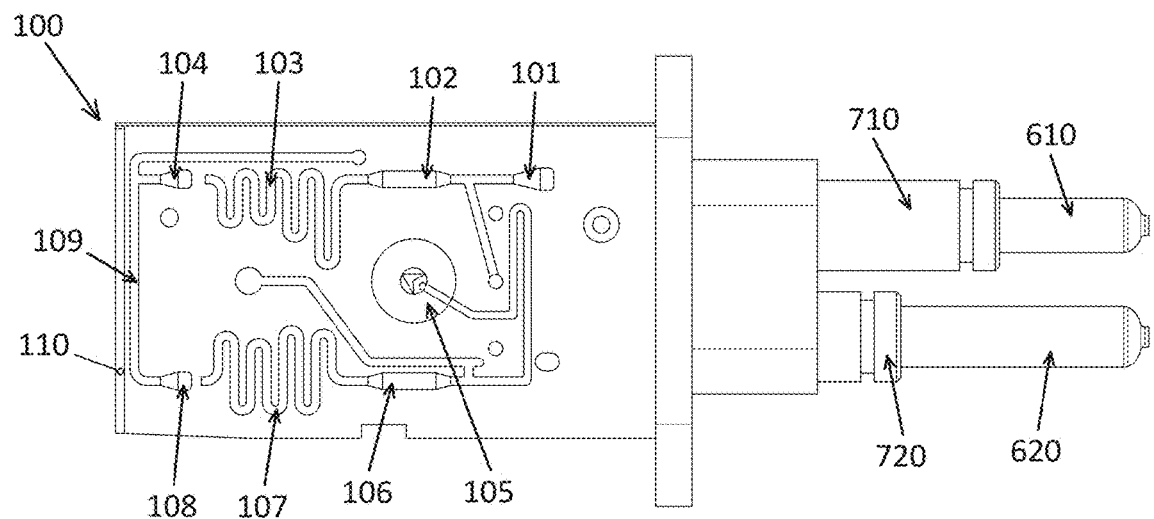
FIG. 4A illustrates a top view of the bottom part of the cartridge attached to the saliva collection device.
Figure 4B:
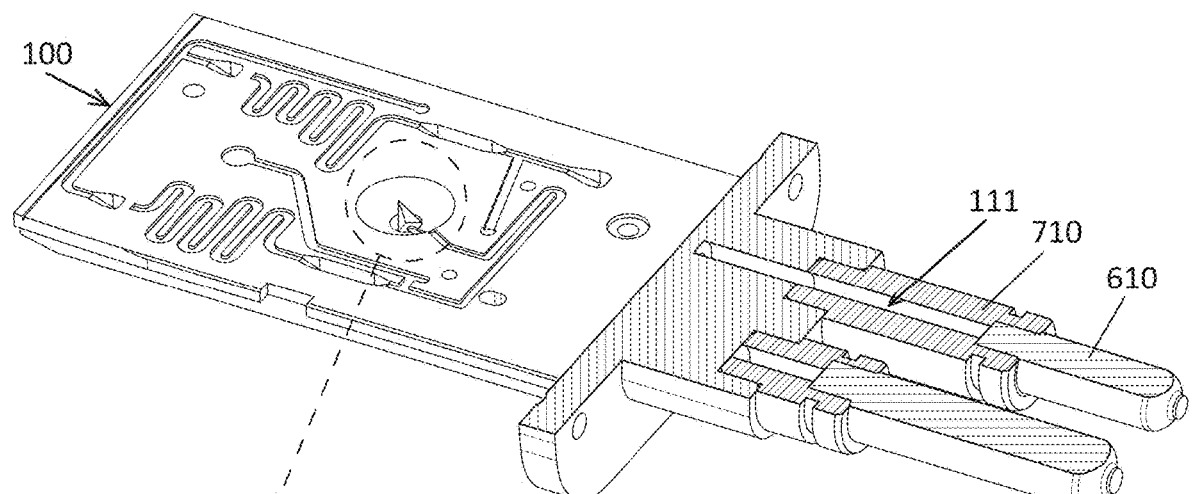
FIG. 4B illustrates a perspective view of the bottom part of the cartridge attached to a cross-sectional view of the saliva collection device.
Figure 4C:
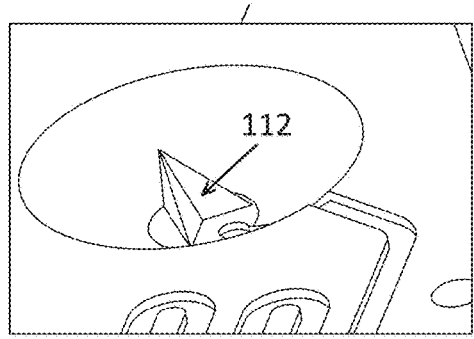
FIG. 4C illustrates a close up view of a piercing element using to puncture a blister pack.

The blister pack 300 can be installed within the disposable device 1000 such that it is very close to, proximate to, or adjacent to a piercing mechanism 112, which may be an integral part of the disposable device 1000. As shown in FIGS. 2, 4A, and 4B, in one preferred embodiment the piercing mechanism 112 is a sharp pointed feature within the moulded cartridge bottom 100. Alternatively, the piercing mechanism 112 may be a sharp needle that is glued onto the cartridge bottom 100. The needle may be made from metal or plastic. Alternatively, the piecing mechanism 112 may be press fit or insert moulded into the cartridge bottom 100. The piercing mechanism 112 can be positioned in a depression within the moulded cartridge bottom 100 such that the blister pack 300 is positioned above the piercing mechanism 112. The cartridge top 200 may have an opening 113 that provides access to the blister pack 300 and allows for an actuator of the reader to push the blister pack 300 into the piercing mechanism and thereby release the contents of the blister pack into the fluid channels.

As shown in FIGS. 1, 2, and 5B, the disposable device 1000 can also include a sensing element 3000 in fluid communication with the fluidic circuit 120. The sensing element 3000 may be a photonic chip which is placed within a cavity 204 in the cartridge top 200. The sensing element 3000 may be held in place by being sandwiched between the cartridge top 200 and cartridge bottom 100 and can be held together by means of an adhesive sealing layer 900, for example.

In one preferred embodiment as shown in FIGS. 1 and 2, the disposable device 1000 has an integrated collection device and cartridge. The cartridge includes primarily the cartridge bottom 100, the cartridge top 200, and the associated components as described herein. The collection device includes primarily a pair of collection swabs 610, 620 and a cap 500 and associated components as further described herein.

Figure 11A:
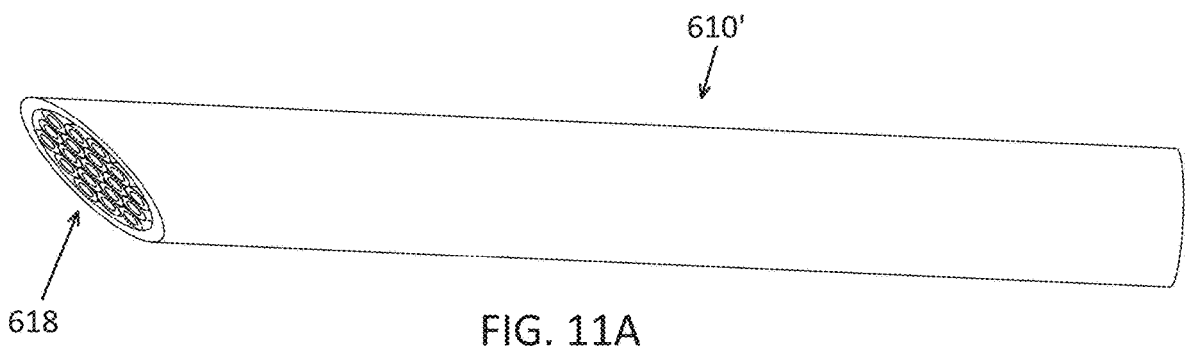
FIGS. 11A, 11B, and 11C illustrate another embodiment of a fluid collection device.
Figure 11B:
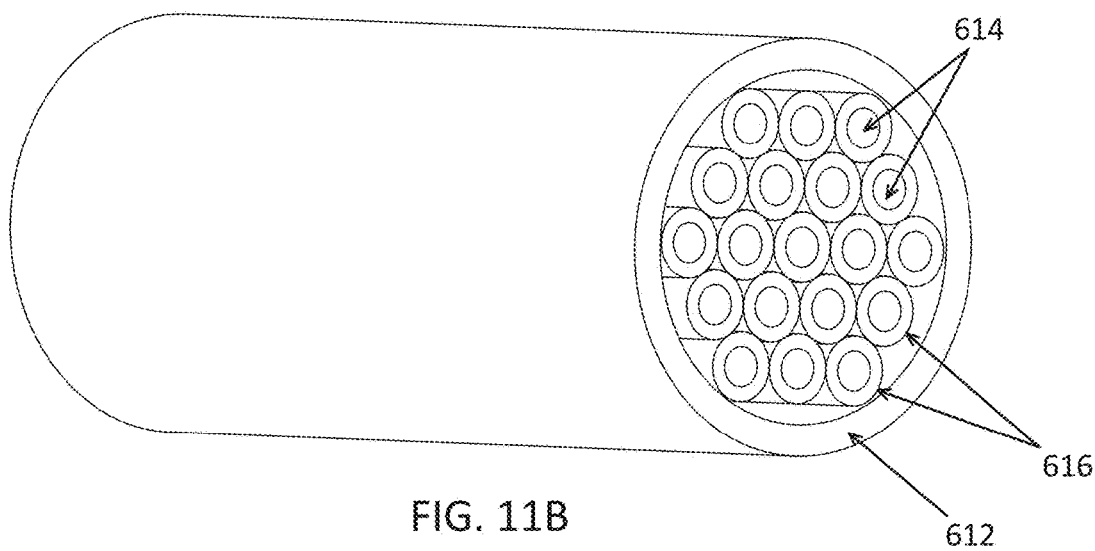
Figure 11C:
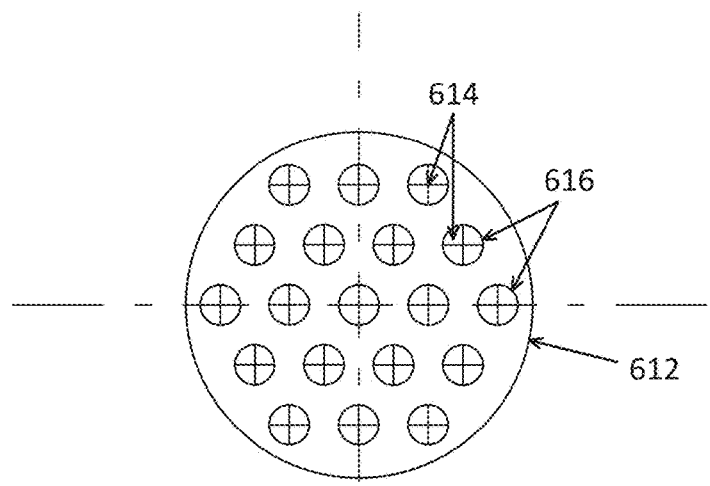

As shown in FIGS. 1, 2, 3A, and 3B, first and second swabs 610, 620 can be held firmly within first and second swab holders (e.g., swab pistons) 710, 720 respectively. The swab holder may alternatively be referred to as swab pistons. The swabs 610, 620 may be held within swab holder 710, 720 by means of press fit. Alternatively, the swabs 610, 620 may also be glued to the swab holders 710, 720. The saliva collection swabs 610, 620 may be made of an absorbent material, such as a sintered porous polymer with an open cell foam structure similar to one used in wicks. Other materials that can be used include polyurethane foam or cellulose fibre. At least one of the saliva collection swabs 610, 620 may have an embedded indicator, such as a colored dye indicator, which changes colour upon contact with oral fluids thus indicating completion of the saliva collection. A saliva stimulant configured to stimulate saliva production from a subject may be included on first and/or second collection swabs 610, 620 or otherwise administered to a subject. Since confirmatory testing by the certified lab typically uses traditional testing systems and protocols, a larger amount of saliva may be collected for the confirmatory sample, such as about 2, 3, or 4 times the amount as compared for the rapid test sample. Therefore, in some embodiments, the indicator is included with the confirmatory saliva collection swab 620. In one embodiment the rapid test saliva collection swab 610 is designed to be a hollow shell. The amount of oral fluid collected can be controlled by the size of the collection swabs 610, 620 and the position of the indicator on and/or within the swabs. FIGS. 11A, 11B, and 11C show another embodiment of a collection swab. First collection swabs 610' may have a structure including a plurality of capillary channels 614. (A second collection swab as used herein may have a generally similar structure as a first collection swab with the most common difference a matter of size or dimensions). Upon placing first capillary collection swab 610' in the mouth of the subject (e.g., under the subject's tongue), capillary channels 614 absorb the oral fluid by capillary action and collect only as much as the channel volume allows them.

Figure 4D:
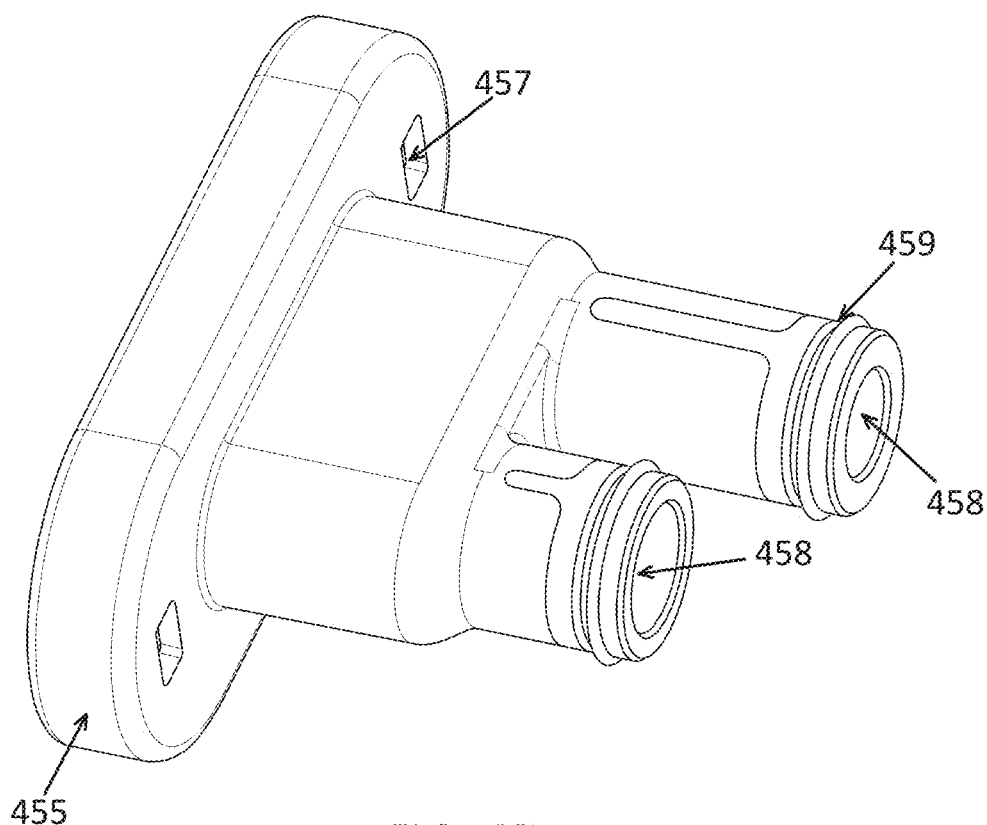
FIGS. 4D and 4E show front perspective and back perspectives, respectively of an example of a distal end of a saliva collection system, showing the collection body and two swab pistons extending distally from the collection.
Figure 4E:
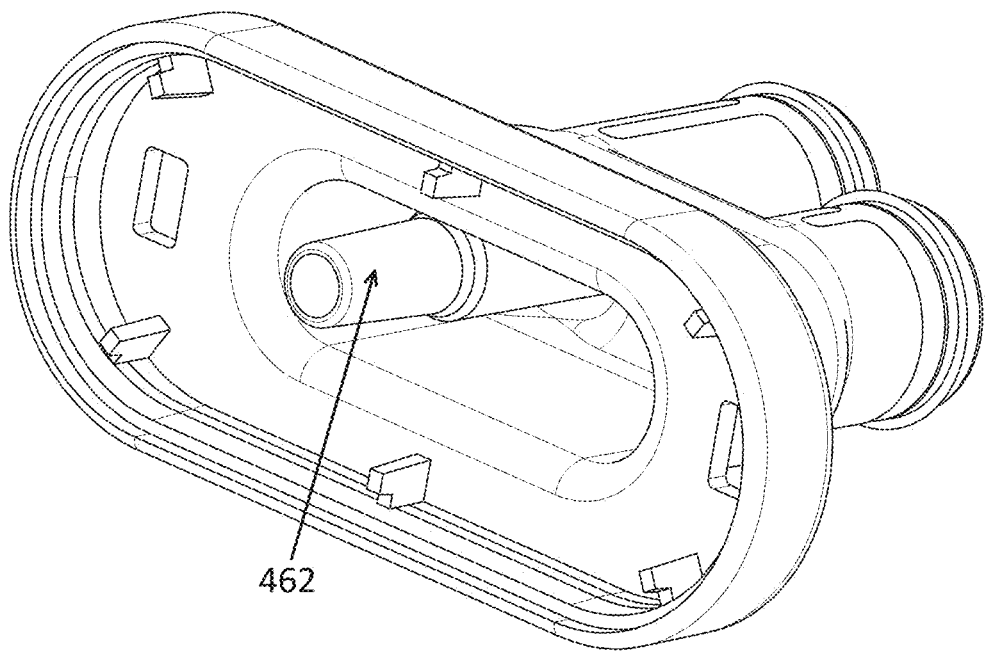

FIGS. 4D and 4E illustrate one example of a collection body 455. The collection body may be flanged outwards and may mate with cartridge (not visible in FIG. 4) body. In some variations the collection body may be the same or integral with the cartridge body. In FIG. 4D the collection body includes a connector 457 (a female portion of a snap fit in this example) for connecting to the cap. A pair of swab pistons 710 extend distally from the collection body. Each swab piston includes an internal channel 458 configured to wick saliva from an open distal end of the first swab piston. For example the channel may hold a porous material and/or capillaries. The swab pistons may each also include a seal (e.g., plunger seal) 459. FIG. 4E shows an internal view of the collection body, showing a connection within the body for fluidic connection to the cartridge portion (e.g., the diluted sample cavity in the cartridge). In this example, the collection body includes a male lure 462 connection for connecting to the cartridge.

The collection body and/or swab pistons may be made of any appropriate material, for example, a clear, transparent, medical grade polycarbonate (PC) and/or (e.g., overmolded with) a medical grade, thermoplastic elastomer (TPE), Shore 40A.

As mentioned, the wicking material within the swab piston, which may be referred to as the swab, may be porous material and/or it may be constructed by putting a number of capillaries 616 together in a bundle with a sheath 612 around them to hold them together or for protection. Such capillaries may be curved or otherwise shaped, but in general will be straight. Alternately a swab may be constructed using a multi-lumen capillary with the requisite number of lumens. The capillaries may be made of glass or plastic material or otherwise manufactured or treated to minimize binding of substances of interest to prevent their loss prior to assay. A swab may be relatively rigid or may be flexible to aid in placement. A swab may have a flat end(s) or may have one or more shaped end 618 as shown in FIG. 11A which may allow easy access to saliva for capillary suction upon placing the swab in the mouth (e.g., under the tongue). An entire swab or swab holder may be shaped to aid in collection and/or handling. Such a shaped end or shaped swab may be flattened, rounded, tapered or so on. Although the capillaries or channel may all be the same length, in some examples, some capillaries or some channels may be shorter than others. For example, capillaries on one side of a taper may be shorter than capillaries on the other side of the taper. Likewise, a swab with a single channel in a hollow shell or a porous material may have different dimensions on different parts, and one longitudinal part of a channel, shell or single material swab may be longer than another part (e.g., 1%-50% longer). FIG. 11C shows a cross section through a swab showing one example of placement of capillaries.

Figure 12A:
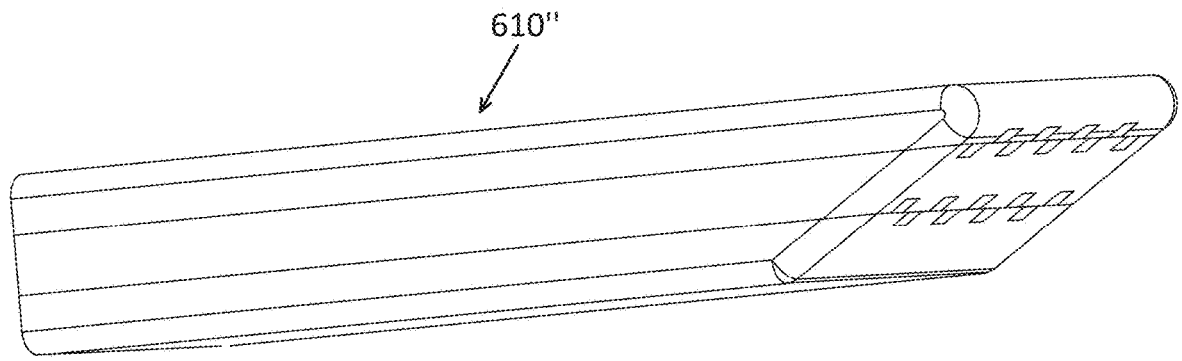
FIGS. 12A illustrates another embodiment of a fluid collection device.
Figure 12B:
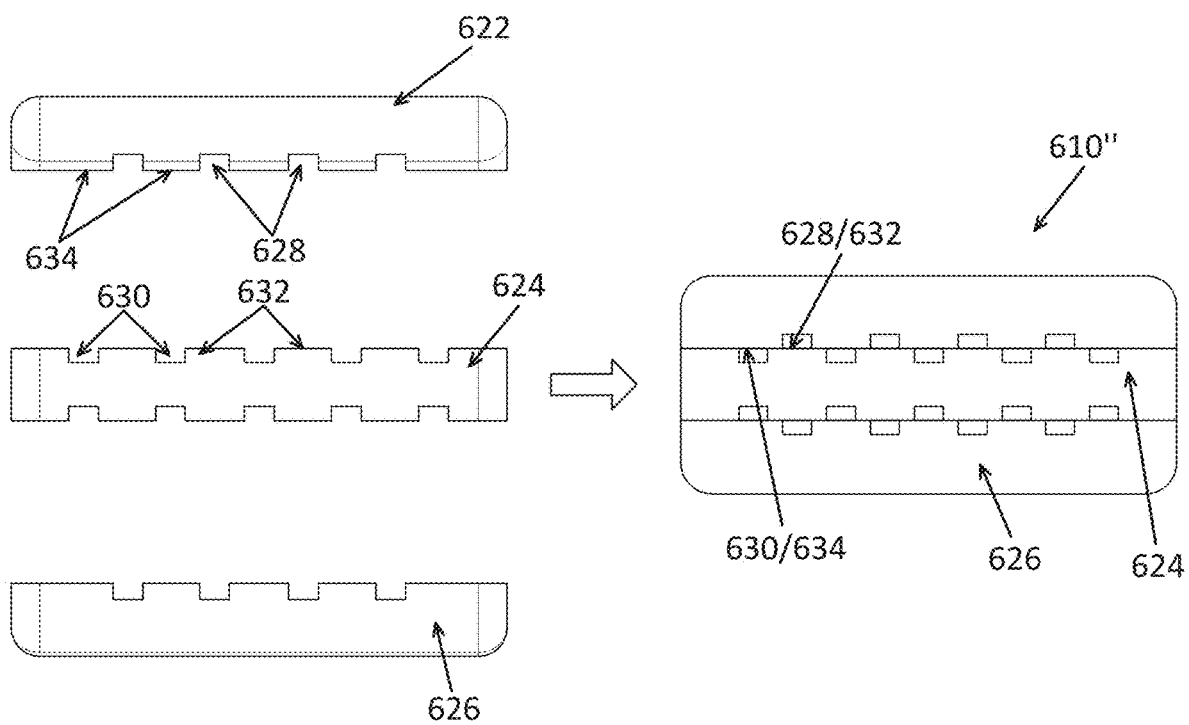
FIG. 12B illustrates an example of how a fluid collection device such as the one shown in FIG. 12A can be manufactured.

FIGS. 12A and 12B illustrate swab 610" with a plurality of channels configured to collect a bodily fluid. FIG. 12A shows a perspective view and FIG. 12B shows a front view of the three sections of a swab before and after joining the sections. A swab may be made in a sandwich construction whereby two or more halves or parts of a swab come together to create capillary channels. Each half or part may be made of a material with channels cut out as shown in FIG. 12B. In some embodiments, an opening (channel) is cut out of one half or part, and the floor or roof of the channel is supplied by another half of part of the swab. In FIG. 12B, top section 622 of swab 610' houses top channels 628 while middle section 624 of swab 610' provides floors 632 for top channels 628 when the top section 622 and middle section 624 of the swab are adjoined. Top 622 of swab 610' also provides roof 634 for middle channels 630 provided by middle section 624. Similarly, middle section 624 and bottom section 626 also form channels. In some embodiments, a cut out channel is half a channel and two half channels come together to create a complete capillary channel(s) (as could be seen if top section 622 and middle section 624 were offset from one another. Channels may be any shape that collects or transports the body fluid, such as circular, rectangular, rounded rectangles and so on. Halves or parts may be plastic and the plastic parts may be manufactured by machining or injection moulding or vacuum forming or any other appropriate plastic manufacturing techniques. The plastic parts may be joined together by pressure sensitive adhesive or liquid adhesive or by ultrasonic welding or any other plastic joining techniques known in the art.

A swab may have at least 2, at least 3, at least 4, at least 5, at least 10, at least 15, at least 20, or at least 30 channels. In some preferred embodiments, a swab may have between 14 and 22 channels, such as about 18 capillary channels. Capillary channel(s) of a swab may have a length between 1 mm and 10 cm and in general will have length between 5 mm and 50 mm (5 cm). In some embodiments, a capillary, a capillary channel, a hollow shell or a porous material has a length of from 5 mm to 40 mm, such as approximately 25 mm (from 10 mm to 25 mm). Each capillary channel or lumen may have a diameter between 0.05 mm and 5 mm, such as between 0.1 mm and 1.5 mm (e.g., between 0.3 mm and 0.8 mm.) In general, a length of capillary selected is less than the capillary head for the selected diameter. That is, for a selected capillary channel diameter, the length of oral fluid pulled into the channel due to capillary action against gravity is greater than the selected length of the capillary channel to ensure consistent collection volume.

Saliva Collection:

In some examples, a pair of saliva samples are collected simultaneously by placing the saliva collection swabs 610, 620 in the mouth of the test subject. The saliva collection swabs 610, 620 may be sized, shaped, and designed ergonomically to be placed under the tongue on either side of the tongue. This may enhance the salivation of the test subject and allow for improved collection efficiency. In some examples, a saliva collection swab may be configured for increasing saliva production, such as allowing or encouraging biting or chewing or may contain a component configured to increase saliva production such as a chemical or odorant. In some examples, components for increasing saliva production may be separate from a collection device, such as a separate vial containing an odorant, etc. In some examples, a single saliva sample may be collected such as a single sample in which part of the sample is used for rapid test analysis and another part used for confirmatory testing. In some examples, two or more saliva samples may be separately collected (e.g., using two or more separate collection devices).

One of the saliva collection swabs 610 is used for the rapid test performed within the cartridge portion of the disposable device 1000, while the saliva sample collected by the other swab 620 may be used for testing by a certified forensic lab for confirmatory testing and/or can also be used for storage as forensic evidence.

Once the saliva/oral fluid is successfully collected by the saliva collection swabs 610, 620, the user applies the collection device cap 500 over the oral fluid collection end, i.e., the saliva collection swabs 610, 620, of the disposable device 1000.

Figure 6A:
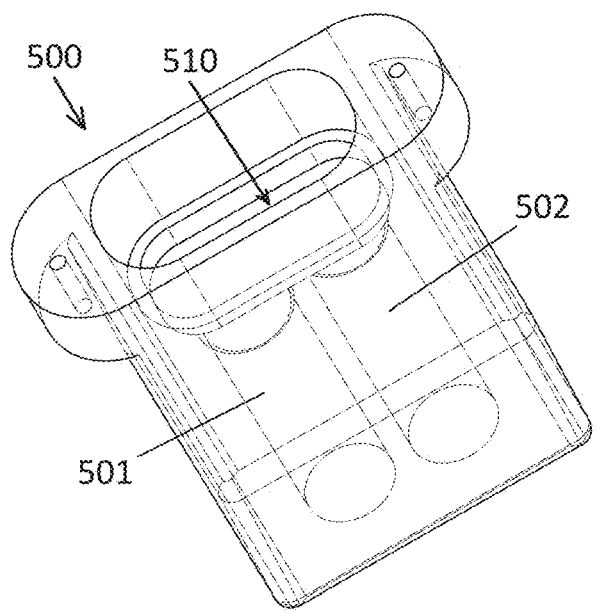
FIGS. 6A and 6B illustrate a perspective view and a cross-sectional view, respectively, of a cap for the saliva collection device.
Figure 6B:
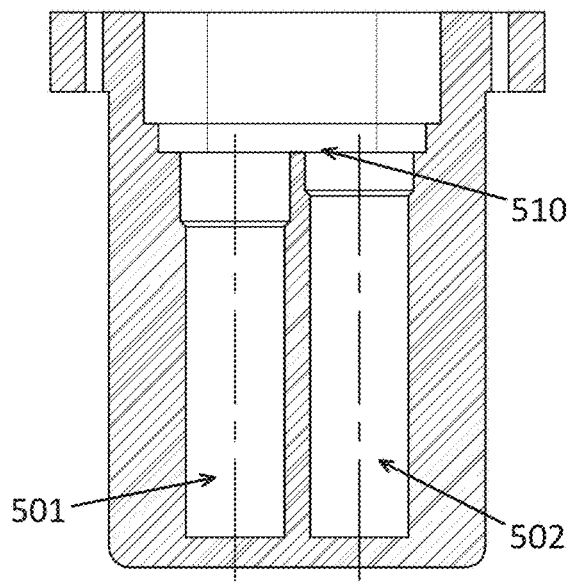

As shown in FIGS. 6A and 6B, the collection device cap 500 has two cavities 501, 502 to receive the saliva collection swabs 610, 620. In some embodiments, the disposable device can have more than 2 collection swabs, such as 3, 4, or 5 swabs, and the device cap 500 can have a matching number of cavities. The rapid test cavity 501 is filled with a known amount of dilution buffer solution used for dilution of the rapid test saliva sample collected by swab 610. The dilution buffer solution may be constituted of 5% bovine serum albumin (BSA) in phosphate buffered saline (PBS), for example. Other concentrations of BSA or other protein can be used, such as between 2-10%. In addition, other proteins may be used in the dilution buffer solution, such as non-fat dry milk, and other buffers can be used, such as tris-buffered saline (TBS). The confirmatory test cavity 502 is filled with a preservation solution used to preserve the confirmatory sample collected by swab 620 so that the confirmatory sample can be sent to a certified lab for confirmatory testing. The preservation solution may include a buffer.

The two cavities 501, 502 filled with dilution and preservation fluids respectively may be sealed by means of a foil cover 510 or other removable or pierceable sealing mechanism, such as a lid or cap. The primary purpose of the foil cover 510 is to contain the dilution and preservation fluids within the collection device cap 500. The foil cover 510 is designed to have very low vapour permeability to prevent or greatly reduce any ingress of water vapour and any evaporation of the fluids within the cavities 501, 502. The foil cover may be a heat sealable foil with a typical multi-laminate construction of a layer of aluminium foil for reduced vapour permeability, and a polymer layer (for example polypropylene) for heat seal ability.

Upon connecting the collection device cap 500 with the cartridge of the disposable device 1000, the collection swabs 610, 620 pierce through the foil seal 510 within the cap 500 and move into the cavities 501, 502. The action of closing the collection device cap 500 generally x initiates the sequence for dilution of the saliva sample for rapid testing.

Figure 6C:
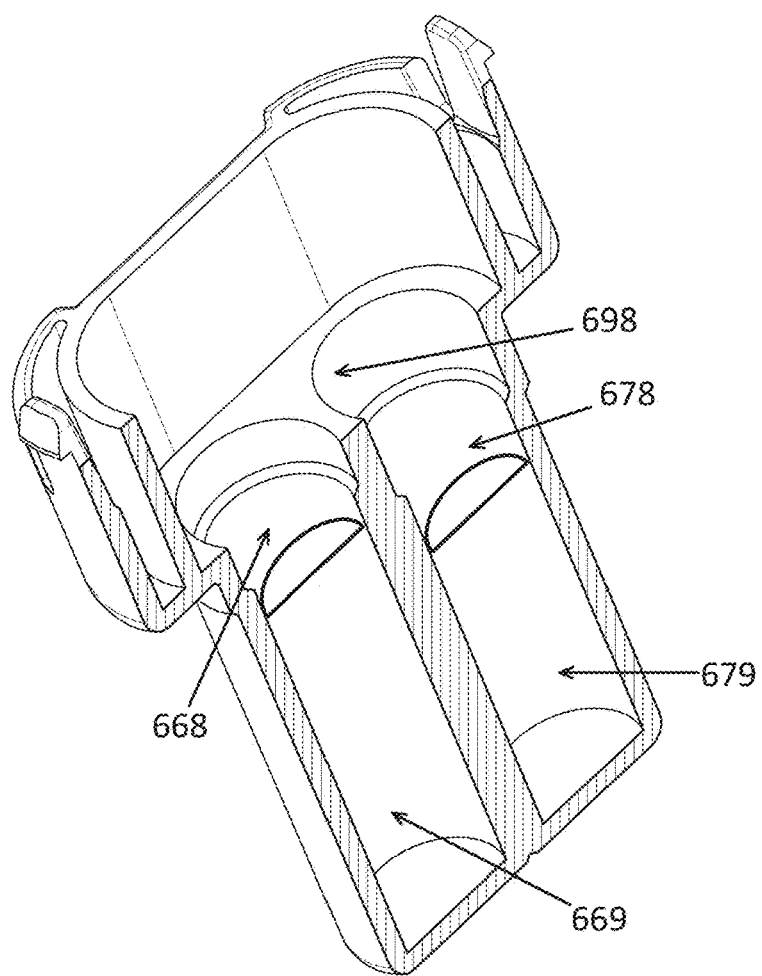
FIG. 6C shows a section through a top of an example of a saliva collection system (with the front side removed).
Figure 6D:
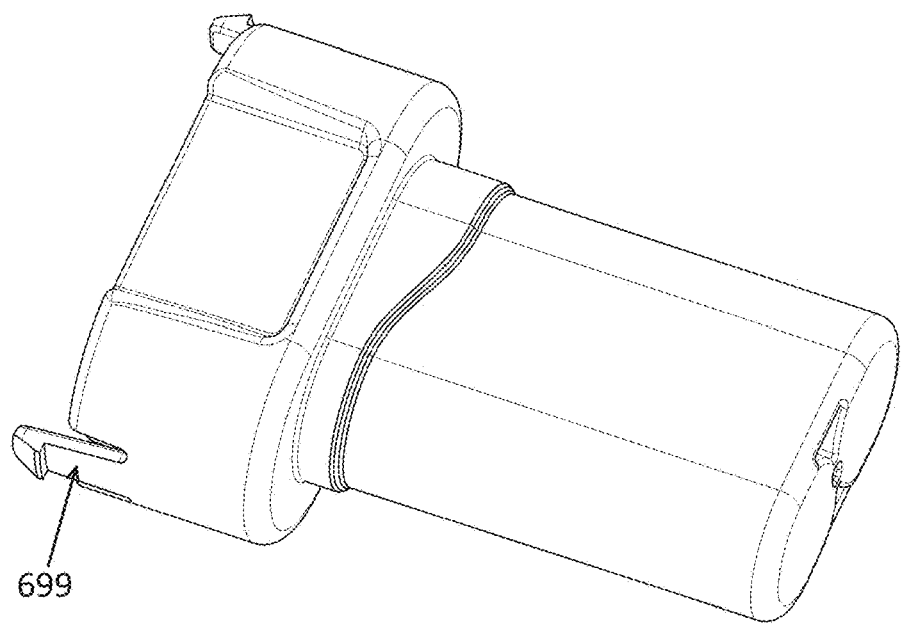
FIG. 6D shows a perspective view of the exemplary saliva collection system top of FIG. 6C.

FIG. 6C-6D show additional examples of a cap. FIG. 6C shows a section view (bisecting the cap in the long axis) shown in the inside of the cap. In this example, the frangible cover (shown as a foil seal 698) enclosed the fluid held within the tubes of the cap. For example, the first tube 678 includes a dilution buffer (rapid test buffer) 679, while the second tube 668 includes a preservation solution (lab test buffer) 669. FIG. 6D shows an external view of this variation of a cap, showing connector (e.g., a male snap-fit connector 699) that may click and lock onto the collection body, as described. In some variations the connector is configured to snap on with a force sufficient to drive fluid from the tubes in the top, through the swab piston, mixing, and dispensing into the diluted sample cavity.

As shown in FIGS. 1 and 2, the swab holder 710 is sized, shaped, and designed to act as a plunger within the cavity 501 of the collection device cap 500. The O-ring 730 fitted onto the swab holder 710 provides a fluid seal between the swab holder 710 and cavity 501 during the plunging action, which ensures that the displaced dilution buffer solution is forced through the collection swab 610 to mix with the collected saliva sample.

In an alternative embodiment, the O-ring may be an over-moulded elastomeric lip type feature to provide the sealing function. The elastomer can be silicone, thermoplastic elastomer (TPE) or any other elastomeric material that does not cause any contamination of saliva/oral fluid sample by means of chemical reaction or leaching chemicals or absorption of analyte.

As shown in FIGS. 1, 2, 4B, 5A, and 5B, the swab holder 710 has a fluid pathway 111 connecting the back end of the porous saliva collection swab 610 to a diluted sample cavity 201 within the cartridge. The diluted sample cavity 201 holds the diluted sample within the cartridge for further use in the rapid test.

As the cap 500 is closed, the swab holder 710 performs a plunging action. The plunging action pushes upon the dilution buffer fluid within the cavity 501. As the cavity is sealed by the O-ring 730, the dilution buffer within the cavity 501 is forced through the porous saliva collection swab 610 and into the diluted sample cavity 201 within the cartridge through the fluid pathway 111. As the dilution buffer moves through the saliva collection swab 610, it mixes with the saliva sample contained within the porous swab 610.

A dilution factor can be defined as:

$$\text{Dilution Factor (DF)} = \text{(Plunged Volume)}/\text{(Volume of Saliva)}$$

The volume of saliva collected depends on the porosity or open space of the saliva swab material and the solid volume of the saliva swab 610, and if used, the location of the fluid indicator on the swab. In general, for a given shape, size and material the maximum or desired volume of saliva collected by the swab 610 is generally fixed. For example, the volume of saliva collected depends on the overall dimensions. For example, the capillary volume within saliva swab 610 is: Capillary Volume=No. of Capillaries×Length of Capillary× Cross-section Area of Capillary. The volume of saliva obtained by a swab may be between $3.0 \times 10^{-5}$ mls to 3 mls. In some particular examples, the volume of saliva obtained by a swab is between 0.01 mls and 1.0 ml (e.g., between 0.1 mls and 1.0 mls).

The amount of fluid pushed through the swab is equal to the volume plunged by the swab holder 710. The dilution factor therefore is dependent only on geometry and material selected. Thus the device disclosed can achieve a very consistent dilution factor. Any variability in the dilution factor is directly controlled by the manufacturing tolerances of the swab 610, and the swab holder 710. The dilution factor may also be measured and calculated by including a known quantity or concentration of a substance in the dilution buffer which is then combined with the saliva sample and tested along with the analyte of interest. The dilution factor can be equal to the known concentration of the substance in the dilution buffer divided by tested concentration of the substance after combination with the saliva sample.

The diluted sample pushed through the swab 610 is collected in the diluted sample cavity 201 within the cartridge. The cavity 201 can be provided with a capillary stop valve 101 to prevent the sample from moving into the fluidic circuit by capillary action.

The collection device cap 500 is then connected to the cartridge by mechanical means. The mechanical connecting means may be a snap fit mechanism to hold the cap in place. Additionally, the mechanical connection can be a single use snap fit that can be designed in a manner such that it cannot be opened without permanently damaging the snap fit mechanism thus preventing any possibility of tampering.

Figure 10:
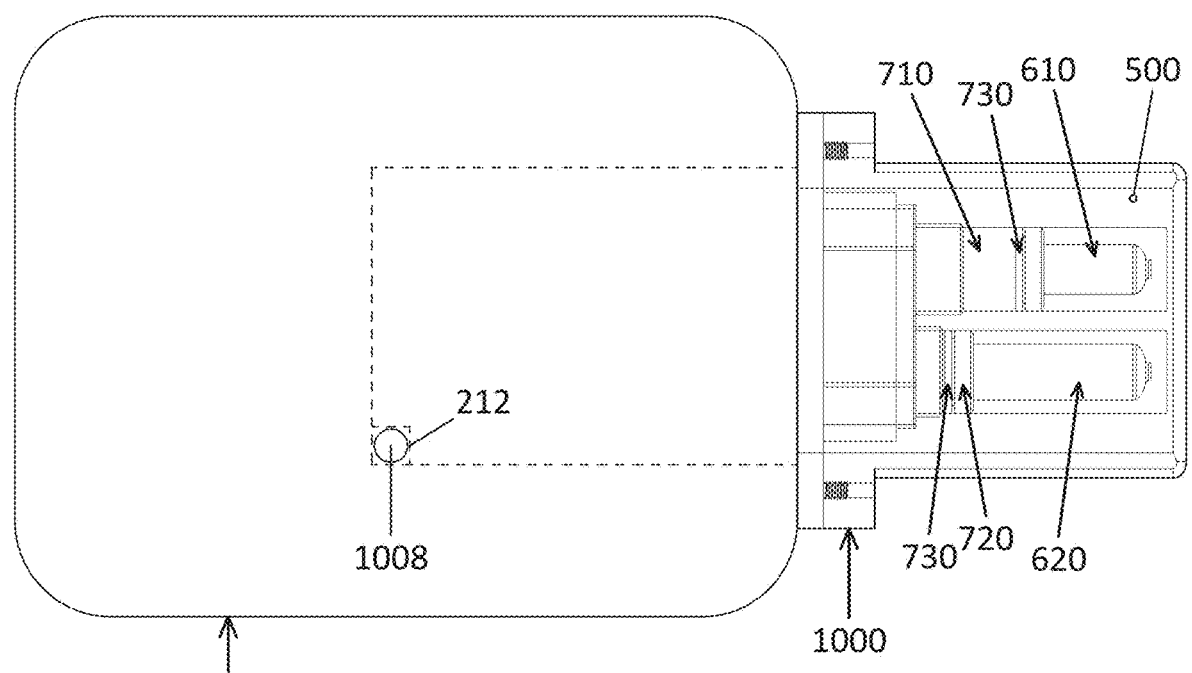
FIG. 10 illustrates the insertion of the cartridge into a reader for testing.

Once the cap 500 is placed firmly, the disposable device 1000 is inserted into a reader 1002 for automated testing as shown in FIG. 10.

The reader module 1002 receives the disposable device 1000 and clamps it in place. As the detection system is an optical sensing system, the disposable device 1000 needs to be accurately located within the cartridge and/or accurately aligned with the optical sensing mechanism in the reader 1002. For this purpose, the disposable device 1000 has two features that ensure accurate alignment of the device within the reader module.

Any of these apparatuses may include a z-alignment feature. With the disposable device 1000 clamped within the reader module, the front face 3102 of the photonic chip is excited by an optical element within the reader. The optical element within the reader also senses the photonic information emitted from the photonic chip.

A Z-gap 1006 can be defined as the distance between the front face 3102 of the photonic chip 3000 and the sensing element 1004 within the reader module. This Z-gap is critical for accurate excitation and sensing of the photonic chip 3000 as the intensity of light transferred between the chip and the sensing element varies with the square of the Z-gap.

As shown in FIGS. 1, 2, 5A, 5B, and 10, upon insertion of the disposable device 1000 within the reader 1002, the face 212 of the cut out feature 208 butts against a dowel pin 1008 present in the reader module 1002. The face 3102 then becomes a reference face for location of all fluidic features and the chip cavity 204 that holds the photonic chip 3000.

With a pre-designed reference face 212 engagement with a pin 1008 in the reader module 1002, the Z-gap 1006 can be accurately controlled and the cartridge to cartridge variation of the Z-gap 1006 can be kept within a controlled narrow band.

Z-gap variability is dependent on the tolerance stack up of features within the disposable device 1000 and is controlled by the manufacturing process.

Figure 13A:
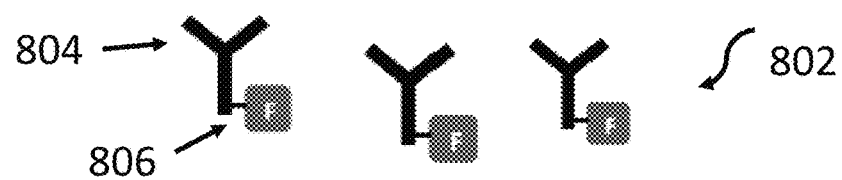
FIGS. 13A, 13B, 13C, 13D, and 13E show an example of an assay useful for detecting an analyte, such as an analyte from a bodily fluid.
Figure 13B:
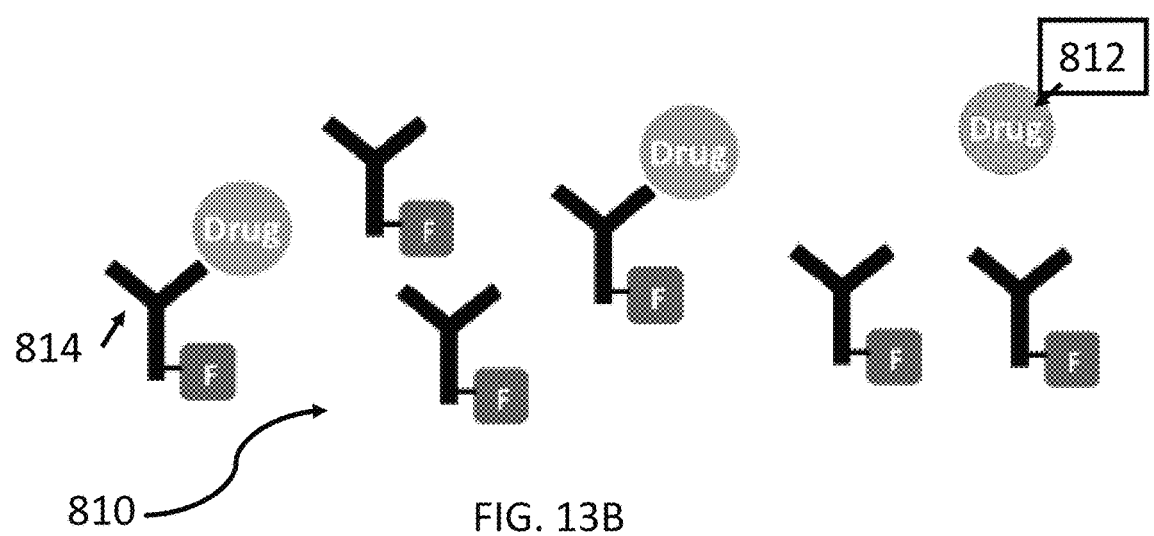
Figure 13C:
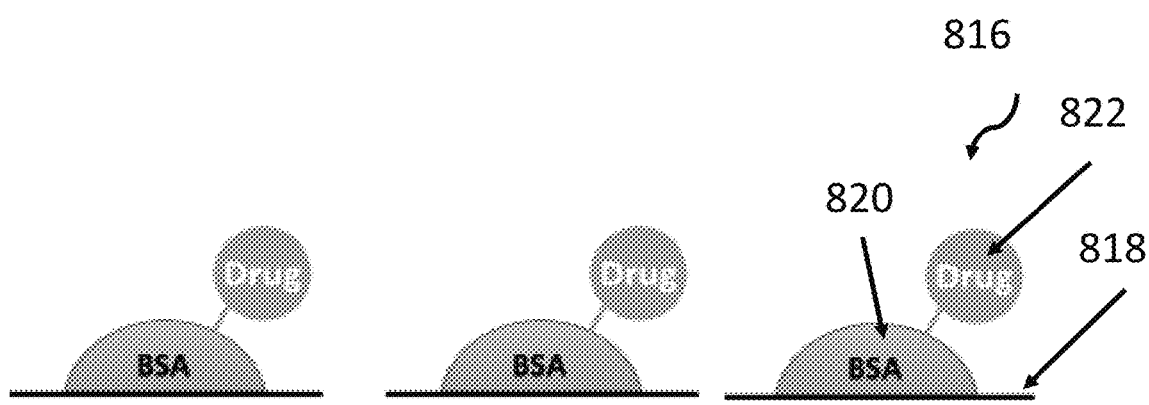
Figure 13D:
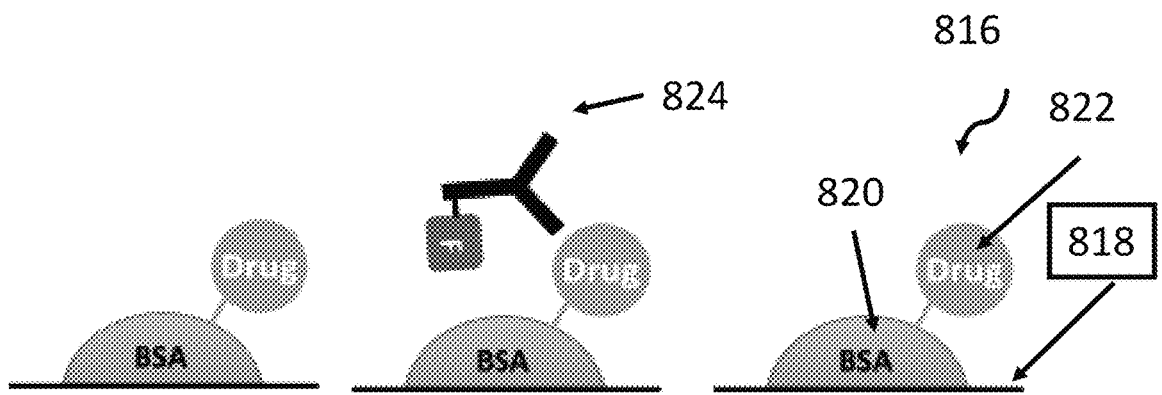
Figure 13E:
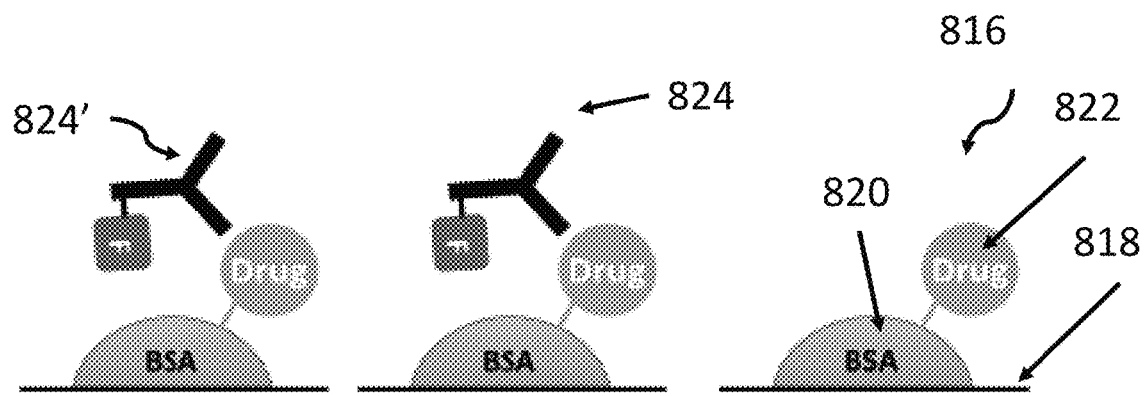
Figure 14A:
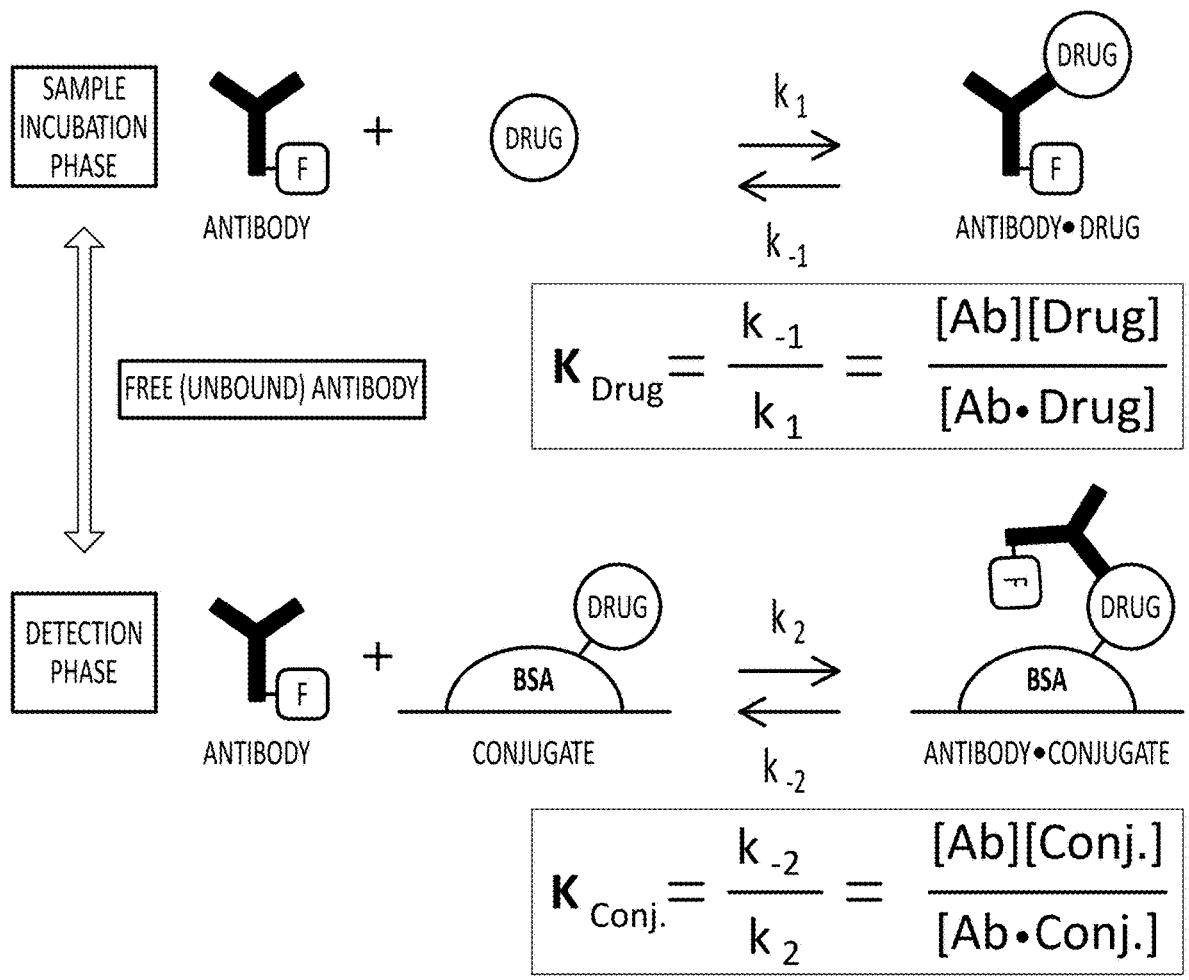
FIG. 14A illustrates kinetics of analyte and antibody binding over time.
Figure 14B:
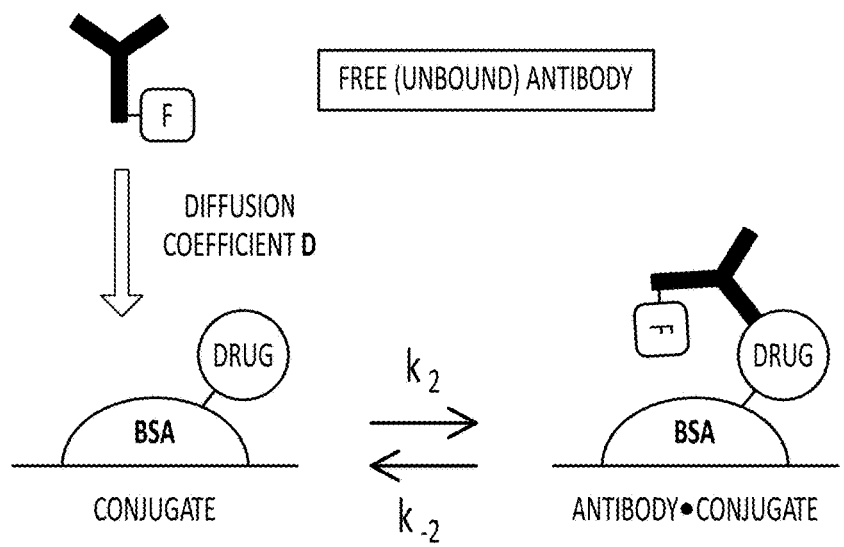
FIG. 14B shows the kinetics over time of free, unbound antibody binding to antigen, such as antigen attached to a sensing well.

Any of the apparatuses described herein may include an optical sealing feature. As shown in FIGS. 8A, 8B, and 9, the sensing method involves a laser illumination of the photonic chip 3000 by means of an optical scan head 1004 within the reader module. The scan head 1004 shines a laser which is received by an optical waveguide 3103 within the chip 3000. The light irradiates the sensing wells 3101 within the chip 3000. These wells have coated reagents, such as antigens of the analytes being tested, which bind with the binding agents (fluorophore conjugated antibodies) added to the sample. The analyte/sensing wells (also called sensing sites) can be pre-conditioned with antigens. An antigen can be bound to a sensing well using any type of tether, such as BSA, another antibody, etc. In some embodiments, the amount of bound antigen in the sensing well 3101 is much greater, such as on the order of at least 10, 100, or 1000 times (e.g. mole per mole) the amount of fluorophore conjugated antibody that is added to the control sample and optionally also the saliva sample. This ensures that the antibodies from the control sample only uses up a very small fraction of the antigen, which can essentially or approximately considered to be an infinite amount relative to the amount of antibody, which means that there is sufficient amount of free antigen to process the saliva sample without washing the sensing wells 3101 to remove the antibody bound to the antigen. The saliva sample may generate a higher fluorescent intensity due to control antibodies left in the well, but this offset can be accounted for, subtracted out, or ignored by measuring the slope of the fluorescent intensity as a function of time. FIG. 13D shows sensing wells 818 with attached antigen 822, for example a drug attached to a sensing well via tether 820 such as a BSA (bovine serum albumin) attachment molecule. Detectably labeled antibody from the control sample has attached to antigen (see the far right of FIG. 13D). Upon the addition of a reacted sample (e.g., a diluted bodily fluid sample incubated with a detectably labeled antibody), unbound antibody will bind to available antigen (see the far left of FIG. 13E) and increase in signal intensity of the sample can be measured over time. As indicated above, FIG. 14B shows the kinetics over time of free, unbound antibody binding to antigen, such as antigen attached to a sensing well. The slope is determined by the diffusion coefficient of the unbound antibody in contacting and binding to the antigen (drug) bound to the well. The top part of FIG. 14A shows the equilibrium between analyte found in a sample binding to antibody (thus preventing such antibody from binding to antigen in a sensing well). The bottom part of FIG. 14A shows the equilibrium between detectably labeled antibody and antigen in a sensing well.

The sample metering well 102 may include lyophilized beads having antibodies conjugated with fluorophores that absorb the incoming laser light and then re-emit at a known wavelength. The re-emitted light from the fluorophores is recoupled into another set of waveguides 3103 which direct the light from the fluorophores back to the front face 3102 of the chip 3000. The re-emitted light by the fluorophores received within the waveguides 3103 is measured by the optical scan head 1004 and is the true measurand within the system.

This re-emitted light from the fluorophores can also couple optically to the fluid (sample or control) in contact with the photonic chip 3000. Such light can then be dispersed into the medium and reach the front face 3102 of the cartridge and can also be picked up by the scan head 1004 along with the light within the sensing waveguides 3103 of the chip. This light may become a major source of error in measurement if not dealt with.

Two key pathways of this 'optical leakage' were identified: (1) the transmission of light through the material of the cartridge bottom 100, and (2) the transmission of light through the double sided adhesive tape 900. To address the optical leakage, the cartridge bottom 100 is made from an opaque material (preferably black polycarbonate).

Figure 9B:
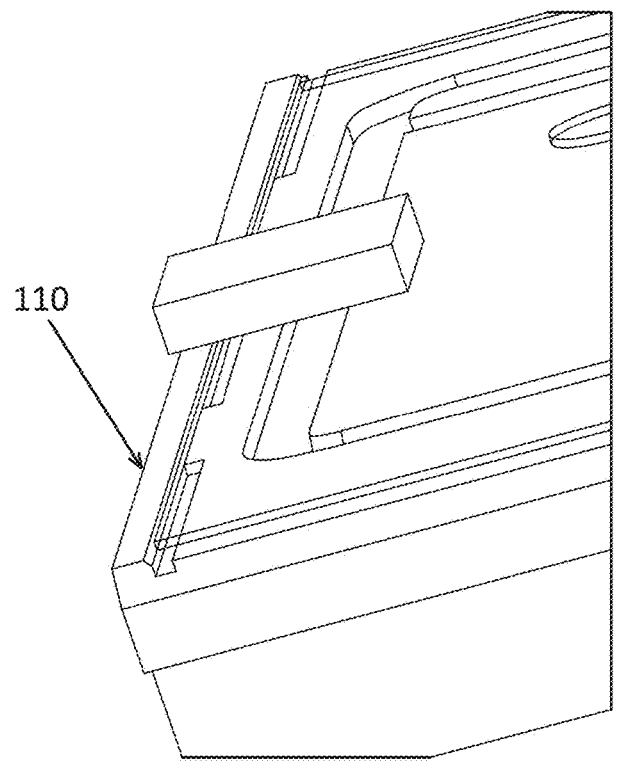
FIG. 9B is another view of an end face of a cartridge showing a ledge or lip region protecting the optical chip.

As shown in FIG. 9A, to block the optical leakage through the double sided adhesive 900, a ledge feature 110 or lip may be provided at the front end of the cartridge bottom 100. The double sided adhesive 900 is placed behind the ledge 110 such that the ledge 110 is between the double sided adhesive 900 and the optical scan head 1004. The height of the ledge 110 is designed such that the double sided adhesive 900 is completely recessed post compression within the sandwich structure of the assembled disposable device 1000. FIG. 9B illustrates another view of a distal end region of a cartridge portion that may integrated with a saliva collection system, the end including a ledge or lip region 110.

Thus the front edge of the cartridge bottom 1000 becomes entirely opaque and provides proper optical sealing and eliminates a major source of error in measurements.

Figure 7:
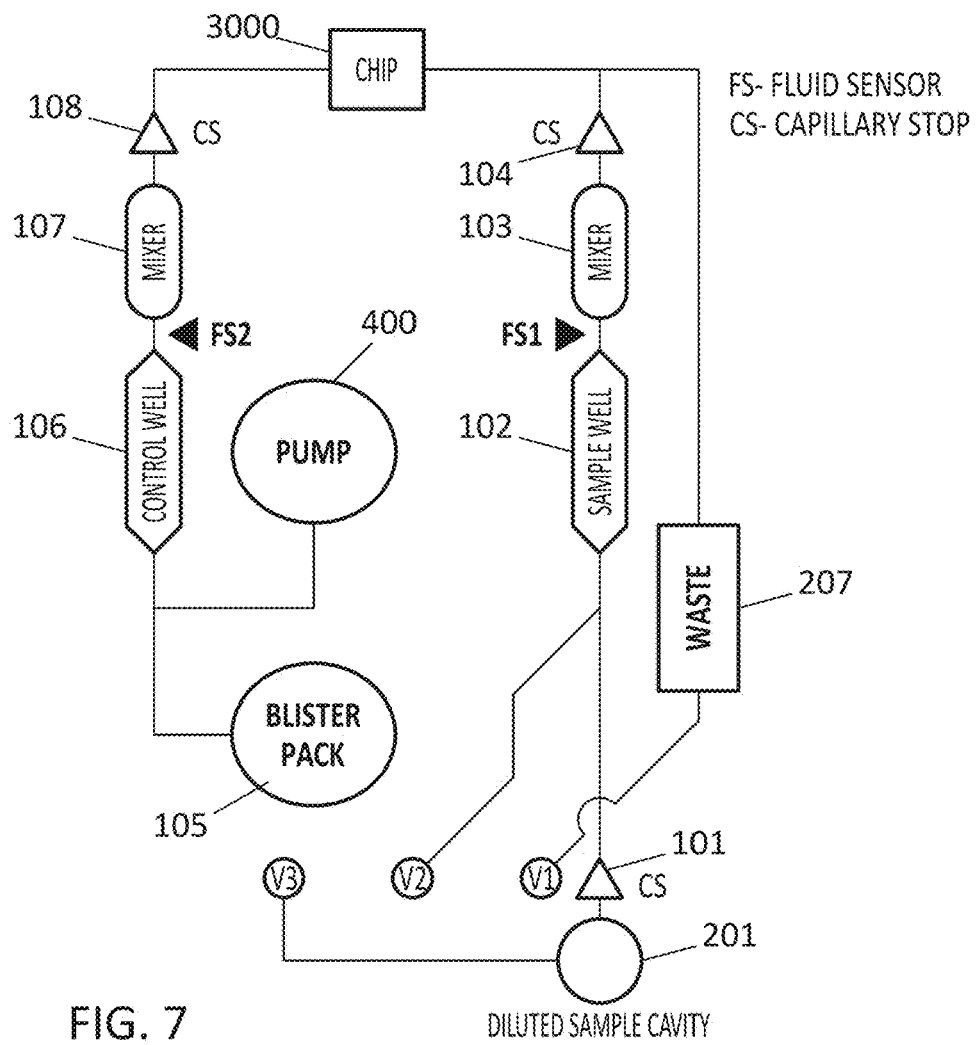
FIG. 7 illustrates a schematic of the parts of the fluidic circuit in the assembled cartridge.

FIG. 7 is a schematic that illustrates how fluid is transported through the fluid channels in the cartridge using a pump 400 and a series of strategically placed vents V1, V2, and V3 and capillary stops 101, 104, and 108. Vent V1 is positioned downstream of the waste well 207. Vent V2 is positioned upstream the sample metering well 102 and downstream the diluted sample cavity 201, i.e., between the sample well 102 and the diluted sample cavity 201. Vent V3 vents and leads to the diluted sample cavity 201. A first capillary stop 101 is located just downstream the diluted sample cavity 201. A second capillary stop 104 is located downstream of the mixer 103 for the sample metering well 102 and upstream of the chip 3000. A third capillary stop 108 is located downstream the mixer 107 for the control metering well 106 and upstream the chip 3000. The diluted sample is received in a chamber (diluted sample cavity) 201 and is retained within the chamber by means of a capillary stop 101. The capillary stops prevent the fluid from advancing through the fluid channels by capillary action. Advancing past the capillary stops generally requires application of the pump. The disposable device has three vent holes V1, V2, and V3. Upon insertion of the disposable device in the reader, the reader establishes establish fluidic connection with the vent holes. The vent holes are in fluidic connection with valves within the reader. These valves allow the reader to open or close the vents as required.

The valves may be solenoid operated plunger type valves or pinch valves or air operated piston valves, for example.

At the start of the test and/or initialization sequence, the vent valve V1 is open to atmosphere and thus allows venting of the waste channel 114. At the same time, vents V2 and V3 are kept in closed position thus sealing off all other channels.

The pump membrane 400 is pushed down to remove air from the pumping chamber. With vent V1 in open position and V2, V3 in closed position, the air escapes through V1 without affecting the sample contained within the diluted sample cavity 201. This primes the pump 400 for a suction operation. Next, vent V3 is opened and V1, V2 are closed. This allows the pump to move fluid in the diluted sample cavity 201. The pump actuator in the reader gradually releases the pump membrane 400 thereby creating suction in the fluid channels. Due the suction, the diluted sample moves past the capillary stop 101 and into the sample metering well 102. A fluid sensor FS1 positioned at the end of the sample metering well 102 senses the presence of fluid (sample) in its view field and the control unit of the reader stops the movement of the pump actuator and the pump membrane 400 and thus stopping the movement of diluted sample in the sample metering well 102 after it has filled the sampled metering well 102.

Fluid sensors FS1 and FS2 may be non-contact optical reflectance or transmission type sensors as part of the reader.

Next, vent V2 is opened and V1, V3 are closed. The pump actuator then further releases the pump membrane 400 to further pull the diluted sample into the mixing chamber 103. At this time, air is pulled into the cartridge through the vent V2, which 'cleaves' off a slug of the diluted liquid sample present in the sample fluid channel. The air thus isolates a slug of diluted saliva sample of a known volume within the sample metering well 102, thereby providing a controlled and metered volume of sample for testing.

Additionally, the sample metering well 102 may contain solid reagents that modify the diluted saliva sample as a part of the assay for analyte detection within the saliva sample. In one preferred embodiment, these reagents are in the form of a freeze dried/lyophilised bead(s) that may include antibodies conjugated with a fluorophore and sugars or other stabilizers for stability. The bead(s) may be placed within the sample metering well 102 of the cartridge during assembly of the disposable device.

Alternatively, the reagents may be in the form of multiple small pellets or powder form for improved dissolution.

Alternatively, the surface of the sample metering well 102 may be spray coated with the reagents to allow better distribution of the dissolved regent within the slug of diluted saliva sample.

The lyophilised bead or other material containing the reagent dissolves upon contact with the diluted saliva sample. Owing to the low diffusivity of proteins within saliva, the dissolved reagents typically create a high concentration zone within the slug of saliva sample. For accurate testing, the reagents need to be uniformly dissolved within the entire volume of metered sample.

Uniform distribution of reagents within the saliva sample is achieved by passing the saliva sample through a mixing chamber 103.

Mixer Operation

The mixing chamber 103 is a passive microfluidic mixer which improves the concentration distribution of the dissolved reagents within the metered slug of the diluted sample.

In the disposable device disclosed herein, the mixing chamber 103 achieves mixing by manipulating the fluid flow to enhance the chaotic advection.

In one preferred embodiment the mixer 103 is a serpentine channel which utilises the variation of speed of fluid around the bends of the sample fluid channel. This difference in speed of fluid between the inside and outside radius of the bend of the serpentine channel creates advection within the cross section of flow. As the fluid moves along the alternating bends of the serpentine channel, the chaotic advection increases and thus enhances mixing. In some embodiments, the fluidic channels, and in particular one or more serpentine channels have an inner diameter of at least 50 um, at least 100 um, or at least 500 um. Such channels may be readily formed using less expensive moulding techniques and/or may allow better mixing, particularly during the back and forth movement and movement around any curves in the channels.

Figure 18A:
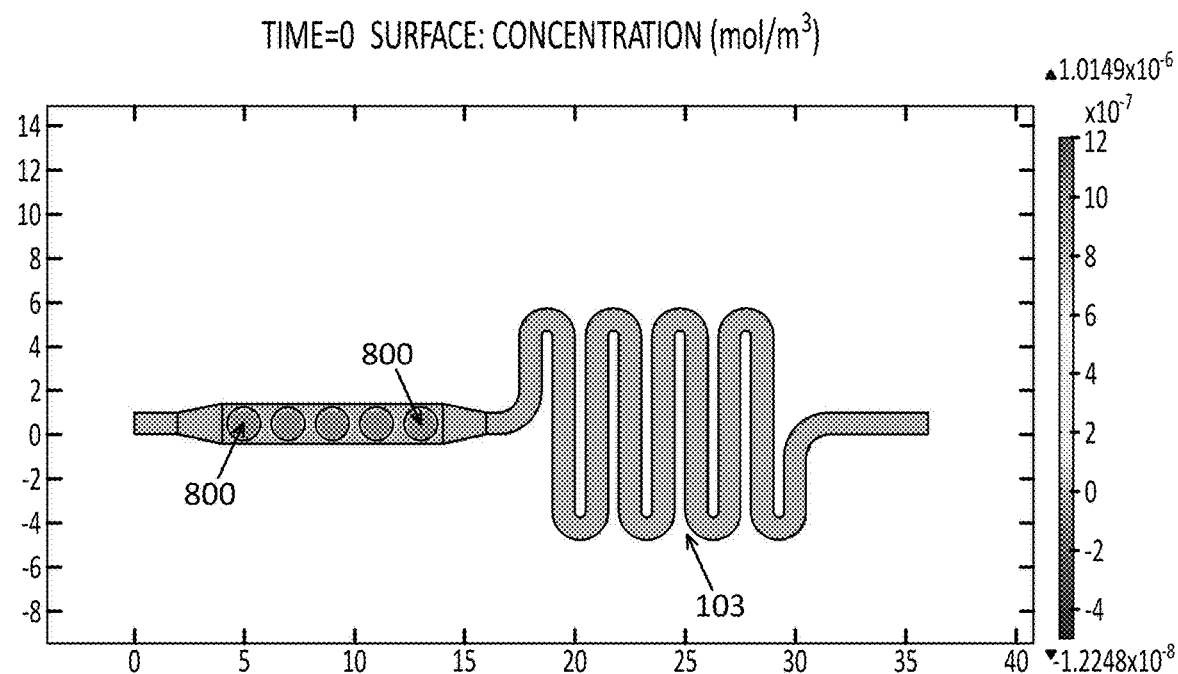
FIG. 18A and 18B show part of a microfluidic circuit with a serpentine mixer useful for mixing a sample and a plurality of dried beads containing a binding agent.
Figure 18B:
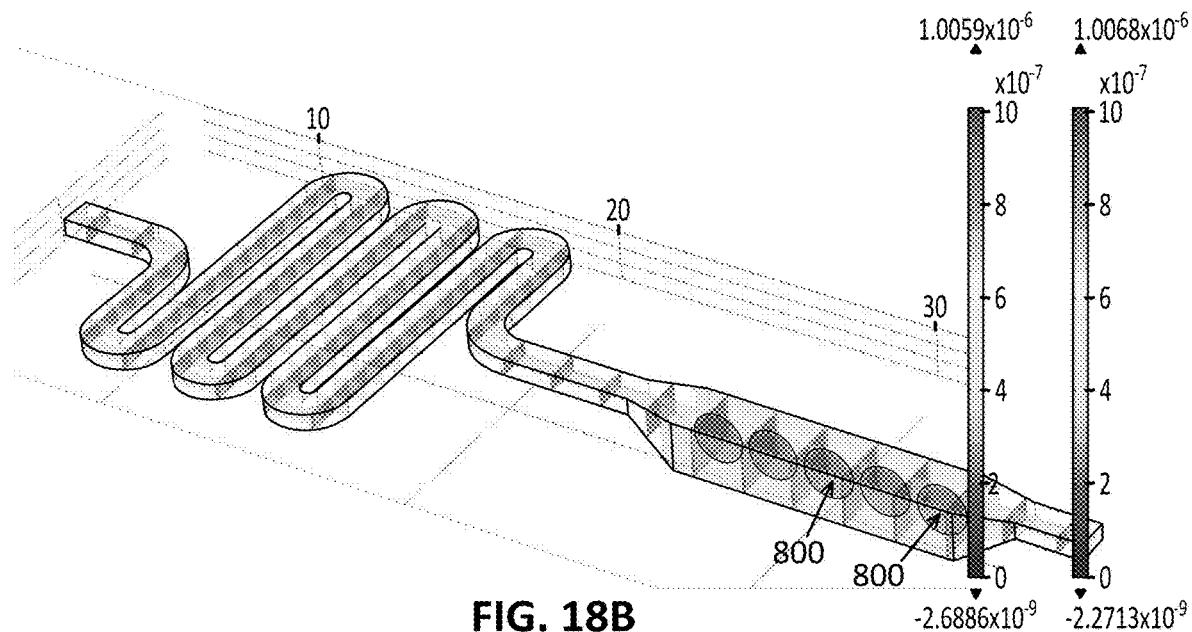

The pump actuation continues to release the pump membrane to pull the metered sample into the mixing chamber 103 and then stops. To reduce the length of channel required for mixing, a multi pass approach may be applied. The pump actuation is reversed and the pump membrane 400 is pushed down to move the metered saliva sample back into the sample metering well 102. The pump actuation is again reversed to pull the sample back into the mixing chamber 103. This process can be repeated multiple times to increase the mixing. FIGS. 18A and 18B shows concentration maps for a fluidic circuit with a serpentine channel and a sample well. FIG. 18A shows a simplified view and FIG. 18B shows an expanded view of a fluidic circuit 120 with a serpentine channel and sample well 102 for mixing a sample. Sample well 102 contains beads 800 with reagent, e.g. detectably labeled antibody. Diluted bodily fluid enters sample well 102 from diluted sample cavity 201, diluting and dissolving beads 800, forming metered sample. The scales on the right indicates reagent concentration (e.g., detectably labeled antibody) in different shades. The highest concentration is in the beads as shown by the dark color. As fluid moves along the alternating bends of the serpentine channel and back and forth between the serpentine channels and even into the sample well, reagent concentration becomes more consistent.

In one preferred embodiment, a relatively uniform distribution was achieved within 3-7 passes of the sample through the mixing chamber 103.

Alternative embodiments of mixer—In a Split and Recombine (SAR) configuration, the fluid channel splits into two or more separate channels and then recombine into a single channel, or a 3-Dimensional Serpentine configuration with cross ridges.

For microfluidic flow, the Reynolds number is typically <1 and hence, diffusion is the dominant mode for mixing of fluids. Typically, assay reagents are small proteins and have low diffusivity in saliva. In addition, diffusion is a very slow process which makes it difficult to mix fluids at microfluidic scales.

Microfluidic mixing schemes can be either "active", where an external energy or force is applied to perturb the sample species, or "passive", where the contact area and contact time of the species samples are increased through specially-designed microchannel configurations.

For a disposable device, active mixing introduces many problems including complicated fabrication, increased cost etc. Passive micromixers contain no moving parts and require no energy input other than the pressure head used to drive the fluid flows at a constant rate. Due to the laminar characteristics of micro-scaled flows (Reynolds <1), mixing in passive micromixers relies predominantly on chaotic advection.

After the mixing step the sample is held within the mixing chamber 103. The capillary stop 104 at the exit of the mixing chamber prevents any movement of sample past the capillary stop 104 due to capillary action.

The vent V1 is then opened and V2, V3 are closed. At this point the blister actuator within the reader pushes down on the blister pack 300. The actuator pushes down on the blister pack 300 in controlled steps till the blister bursts and releases the control fluid out of the blister pack 300 and into the control fluid channel.

The blister actuator pushes further on to the blister pack 300 to push the control fluid into the control metering well 106. A fluid sensor FS2 positioned at the end of the control metering well 106 senses the presence of the control fluid in its view field when the control metering well 106 has been filled and the control unit of the reader stops the movement of the blister actuator and thus stopping the movement of control fluid in the control metering well 106.

The pump actuator then pushes down on the pump membrane 400. Since the pump is located upstream the control metering well 106, this pushes air into the control fluid channel which 'cleaves' off a slug of the control fluid present in the control fluid channel and control metering well 106. The air thus isolates a slug of control fluid of a known volume within the control metering 106, thereby providing a controlled and metered volume of control fluid for measurements.

Additionally, the control metering well 106 may contain solid reagents that modify the control fluid as a part of the assay measurements/testing. In the preferred embodiment, these reagents are in the form of a freeze dried/lyophilised bead(s). The bead(s) may be placed within the control metering well 106 of the cartridge during assembly of the disposable device.

Alternatively, the reagents may be in the form of multiple small pellets or powder form such as for improved dissolution. Additionally, a control reagent may include one or a plurality of types of control reagents. Such reagents may be in a single bead, pellet, powder or other form, or may be in a plurality of beads, pellets, powders or other forms or a combination (e.g., one control reagent in a bead, another control reagent in a powder, etc.). A control reagent may be an antibody or other molecule configured to bind to a substance of interest (e.g., a drug, a legal substance, an illegal substance, a metabolite of such substances and so on). Two or more control reagents may be used to assay a single substance such as by using a first control reagent to detect a substance of interest and using a second control reagent to detect a metabolite (or different epitope or part) of a substance of interest.

Alternatively, the surface of the control metering well 106 may be spray coated with the reagents to allow better distribution of the dissolved regent within the slug of control fluid.

The lyophilised bead containing the reagent dissolves upon contact with the control fluid. For accurate testing, the reagents need to be uniformly dissolved within the entire volume of the metered control fluid.

Uniform distribution of reagents within the control fluid is achieved by passing the control fluid through a mixing chamber 107. The mixing method is the same as described for the diluted saliva sample.

After the mixing step in some examples the control fluid may be held within the mixing chamber 107. The capillary stop 108 at the exit of the mixing chamber 107 prevents any movement of the control fluid past the capillary stop 108 due to capillary action. In other examples, the control fluid may be moved out of mixing chamber 107 immediately after mixing and into chip channel 109 for assay.

At this point, at least the sample fluid or both the sample and control fluids are held stationary within the respective mixing chambers for a fixed duration (typically 5-10 minutes). This allows for antibodies to bind with the analyte in the sample. FIG. 14A illustrates the kinetics of antibody binding with analyte in the sample during the sample incubation phase.

After incubation of the sample and control fluids, the pump actuator pushes down on the pump membrane 400 to move the control fluid out of the mixing chamber 107 and into the chip channel 109. The pump actuator pushes down on the membrane 400 a known amount which in turn moves the control fluid a known distance within the chip channel 109. The control fluid is stopped at a point in the chip channel 109 such that the control fluid covers the entire sensing area of the chip 3000. At this point optical measurements are made to sense the analyte reaction within the control fluid.

Post-measurement, the entire metered volume of control fluid is pushed further into the waste well 207. The selected chip channel and pump volume ensures that the entire chip channel 109 is empty after pushing the control fluid into the waste well 207.

Next, vent V2 is opened and V1, V3 are closed. The pump actuator then moves in reverse direction to release the pump membrane 400 and create suction within the sample fluid channel. This moves the incubated sample out of the mixing chamber 103 and into the chip channel 109. The fluid is moved a known amount such that the metered volume of the incubated sample covers the entire sensing area of the chip 3000. Optical measurements are made to sense the analyte reaction within the saliva sample.

Upon completion of measurements, the pump is released completely. This moves the saliva sample out of the chip channel 109 and into the control fluid channel which now functions as a secondary waste well. Since many tests only require the detection of a threshold amount of the analyte such as a drug, a single control sample having the analyte at the threshold concentration is sufficient to establish whether the saliva sample has a concentration of analyte that is greater than, less than, or equal to the threshold concentration. A readout to a user in such a case may indicate "Pass" or "Not detected" or "Fail" or "Detected or "Error" or the like. If an absolute concentration of the analyte is desired instead, multiple blister packs having varying concentrations of the analyte of interest can be added to the cartridge and tested to construct a calibration curve.

As indicated above, included herein is a method for analyzing a bodily fluid from a subject. A bodily fluid may be analyzed for detecting for one or more than one substances of interest (analytes), such as 2, 3, 4, 5, or more than 5 substances of interest. The method may include the steps obtaining or having obtained a bodily fluid sample from a subject, the sample suspected of containing a first analyte. Although any bodily fluid (or biofluid) such as blood, breast milk, plasma, sweat, tears, urine, etc., may be used, in general the method uses an oral fluid such as a saliva sample that may readily be obtained non-invasively and without requiring any special facilities such as a lab or bathroom. Such a fluid may be readily obtained from a subject by a person having no medical training and no or very little special training. FIGS. 13A-13E show how a method for analyzing a body fluid from a subject for a substance of interest.

A method as described herein may include the steps of mixing the bodily fluid sample with a first detection reagent comprising a first aliquot of a first binding agent. In general a first binding agent will include or contain or will bind to a detectable label. A first detection reagent may include a plurality of binding agents (second, third, fourth, etc.). A detectable label associated with a binding agent may include a label detectable by a reader using a laser and evanescent sensing. One or more than one types of detectable labels may be used. For example, detection of each of a plurality of analytes may use different detectable labels such that each analyte may be analyzed. In some examples, two or more analytes may use the same label. For example, a binding agent for two different opioids may use the same label such that a bodily sample can be determined to have more than an acceptable amount of "opoid". In some examples, a first (second, third, etc.) binding agent is a detectably labeled antibody configured to bind a substance of interest (first analyte, second analyte, third analyte, etc.) in the bodily sample to generate a sample mixture. A label may be a fluorophore attached to or configured to be attached to an antibody. A method as described herein may include a step of incubating the sample mixture under conditions configured to bind first analyte (second analyte, third analyte, etc.) to the first binding agent (detectably labeled antibody; second binding agent, third binding agent, etc.) to generate a reacted sample from the subject wherein first (second, third, etc.) detectably labeled antibody that is not bound to first analyte (second, third) has an available epitope. The amount of antibody may be in excess of analyte. In other words, only some of the available antibody may be bound to analyte. A method as described herein may include providing a first control sample comprising a first control aliquot of first (second, third, etc.) binding agent. A binding agent may be one or more detectably labeled antibodies wherein the antibodies are not bound to an antigen or analytes and have an available epitope. Such a first control aliquot may include a plurality of antibodies, which may be initially be found in a test device as non-aqueous or lyophilized or dried as beads, pellets, sprays, etc. and may be located in control metering well 106 as described elsewhere herein and may be reconstituted using solution from blister pack 105. A non-aqueous or lyophilized or dried beads, coating, pellets, sprays, etc. may contain a single binding agent or may contain a plurality of binding agents. For example, a single dried bead, coating, pellet, spray may contain just 1 binding agent or may contain 2, 3, 4, 5, or more binding agents. Alternatively, a system as described herein may include a plurality of dried beads, coatings, pellets, or sprays and such each one may include only a single binding agent or only a subset of binding agents. A particular delivery form for binding agent(s) may be chosen for cost or ease of manufacturability, ease or speed of reconstitution or so on. A first control sample may include a one or more than one detectably labeled binding agents. A method for analyzing a bodily fluid as described herein may include the step of providing at least one analyte sensing site having a supply of first antigen (second antigen, third antigen, etc.) attached thereto. At least one analyte sensing site may include 1 or more (2, 3, 4, 5, 10, 20 or more or anything between these numbers) of analyte sensing sites such as analyte sensing sites 3103 shown in FIG. 8B. A method for analyzing a bodily fluid as described herein may include the steps of passing the first control sample over the at least one sensing site to thereby conjugate first binding agent (detectably labeled control antibody) to the first (second, third, etc.) antigen in the at least one sensing site and thereby activate a first (second, third, etc.) detectable control signal.

A method for analyzing a bodily fluid from a subject may also include the step of after the passing the first control sample step, measuring over time detectable signal from the at least one sensing site to generate a first set of measurements. Such measurements may be taken over time from the same at least one sensing site. As shown in FIG. 8B and described in detail elsewhere herein, detectable signals from a plurality of such sites may be collected in a single waveguide 3101 (a sensing waveguide). In a particular example, detectable signals (optical radiation) from between 6 and 10 analyte sensing sites are collected into a single sensing waveguide and assayed. Detectable signals (optical radiation) for each detectable signal (fluorophore) may be collected over time, measured and plotted on an X-Y graph to obtain a slope based on signal intensity vs time. As discussed in more detail below, the slope of the control graph may be compared with the slope of signal intensity vs time for a bodily sample such as handled as described herein to calculate an amount of analyte present in the bodily sample. Although only one binding agent may be present, in other cases a plurality of different binding agents (antibodies) may be present in an aliquot of a single reagent or in a single control metering well each with a different detectable label. In general, a separate control graph is generated for each detectable signal (for each antibody).

A method for analyzing a bodily fluid from a subject may also include the step of passing the reacted sample from the subject over the at least one analyte sensing site and conjugating reacted sample antibody having the available epitope to first antigen in the at least one sensing site and thereby activating a first detectable sample signal from the at least one sensing site; after the passing the reacted sample step, measuring over time detectable signal from the at least one sensing site to generate a second set of measurements; and comparing the second set of measurements to the first set of measurements to thereby determine a level of first analyte in the bodily fluid; wherein first reacted sample does not substantially bind to the first antigen in the at least one analyte sensing site if first analyte is bound thereto. In some examples, a sample of bodily fluid is diluted prior to the mixing or incubating with a binding agent. A bodily fluid, especially an oral fluid such as saliva, may be relatively viscous and diluting the sample prior to analysis may make it easier to handle and assay.

This may conclude the rapid test and the cartridge can be removed from the reader module. The disposable device 1000 may then be packaged in a sealed container to be sent out to a forensic or other lab for confirmatory testing. The sealed container may be a sealable bag such as a Ziplock bag or a standard evidence bag used by the law enforcement agencies, for example. In addition to using a standard evidence bag, chain of custody can be maintained and documented by use of barcodes or other identifiers which can be attached to the swabs and/or other parts of the system.

Assays as described herein may be especially useful for detecting a substance of interest and especially for detecting a substance that may alter cognition and affect a subject's actions or behavior (e.g., a drug, a drug of abuse, a legal substance, an illegal substance, a metabolite of such substances and so on). Substances of interest may be detected directly or a form of a substance, such as a metabolite, may be detected. In some examples, a single substance of interest may be detected using the systems described herein and in other examples, a plurality of different substances may be detected using a multiplex assay. In some examples, a single substance of interest may be detected using two assays in a system, For example, or more control reagents may be used to assay a single substance such as by using a first control reagent to detect a first substance and using a second control reagent to detect a metabolite (or different epitope or different part) of the same substance.

Substances that may be analyzed using the systems described herein include cannabinoids, depressants, hallucinogens, muscle relaxants, narcotics, sleep aids, and stimulants. Substances that may be analyzed using the systems described herein include 11-Hydroxy-$\Delta$9-tetrahydrocannabinol (11-OH-THC, 11-hydroxy-THC, or 11-nor-delta-9-THC-COOH), 11-nor-9-carboxy-THC (THC-COOH), amphetamine, another cannabinoid, a barbiturate, benzodiazepine, benzoylecgonine, buprenorphine, cocaine, d-Amphetamine (AMP), ecstasy (MDMA), ethyl alcohol, fentanyl, heroin, heroin metabolite, hydrocodone, lysergic acid diethylamide (LDS), mescaline, methadone, methadone metabolite, methaqualone, morphine, an opiate, oxazepam, oxycodone, phencyclidine, synthetic cannabinoid, tetrahydrocannabinol (THC cannabinoid), and so forth.

In some particular examples, one or more than one or all of the following are sensed using the systems described herein: amphetamine, benzodiazepine, cocaine, marijuana, methamphetamine, and opiates. In a particular example, at least three of benzodiazepine, cocaine, fentanyl, and marijuana (THC) are sensed.

EXAMPLES

Figure 15A:
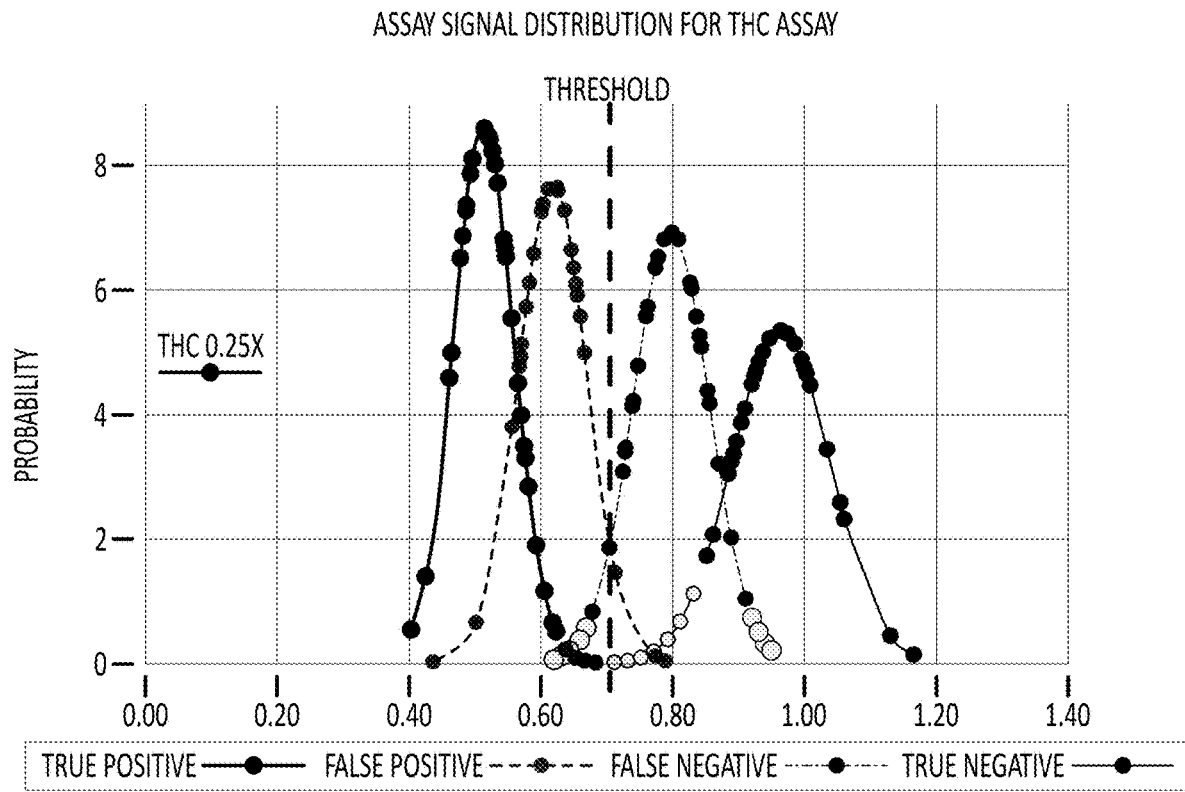
FIG. 15A and 15B shows results of an assay signal distribution as described herein for detecting the presence of marijuana (THC; tetrahydrocannabinol) in a sample.
Figure 15B:
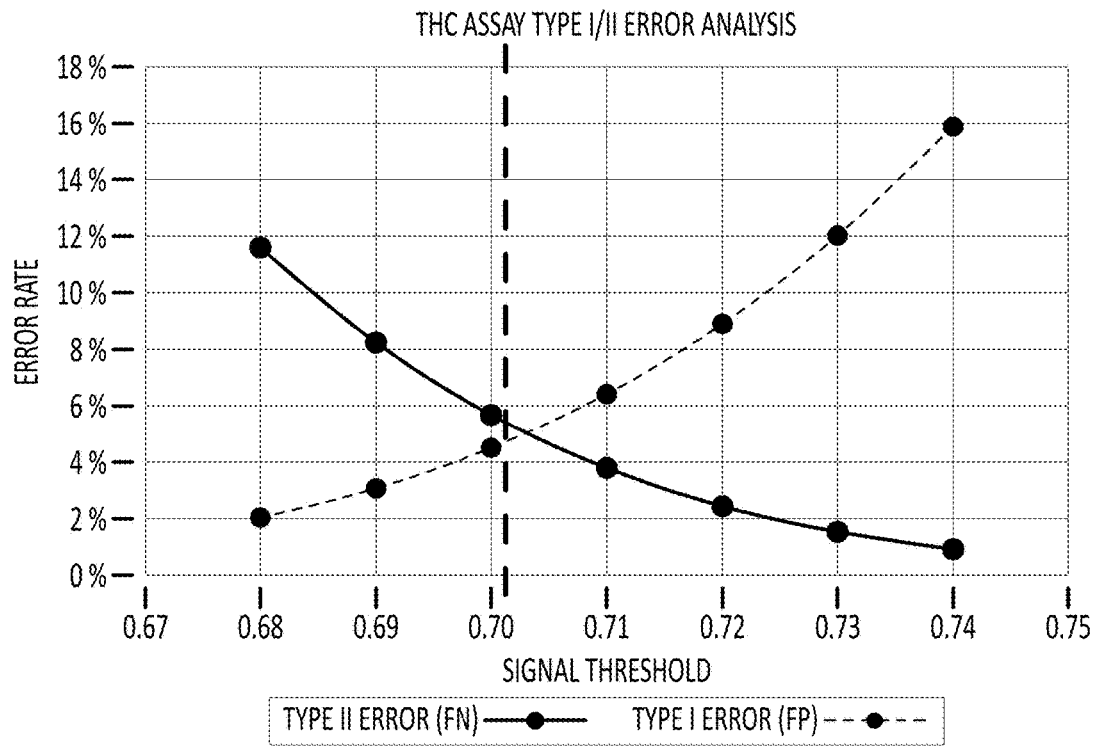

Example 1 FIG. 15A and 15B shows results of an assay signal distribution as described herein for detecting marijuana (THC; tetrahydrocannabinol) in a sample. An assay is a balance between specificity and sensitivity: calling true negatives (TN; calling a result that was actually negative negative), false negatives (FN; calling a result negative when it was actually positive), false positives (FP; calling a result positive when it was actually negative) and true positives (calling a results positive when it was actually positive). FIG. 15A shows a graph of probability for (from L to R) true positives, false positives, false negatives, and true negatives using the systems and assays described herein. A threshold value of about 0.7× provides a balance between minimizing both false negatives and false positives (see the point at which these two curves overlap) and maximizing true negatives and true positives. Other threshold values could also or instead be chosen to increase/improve either specificity or sensitivity. FIG. 15B shows a graph of error rate vs signal threshold. At a threshold around 0.7 (0.72) the error rate from false positives (the curve starting high on the left side of the graft) and the error rate from false negatives (the curve starting low on the left side of the graft) are both less than 6%. This graph assumes that the 30 measurement of the samples are normally distributed.

Figures 16A, 16B:
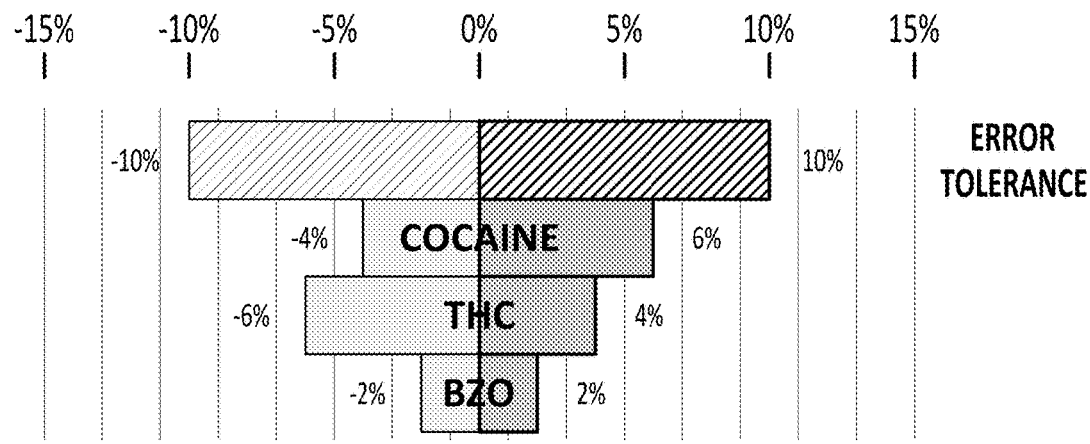
FIGS. 16A and 16B shows results from a multiplex assay as described herein for detecting cocaine (COC), marijuana (THC; tetrahydrocannabinol) and benzodiazepine (BZO) from a bodily fluid sample.

Example 2 is shown in FIGS. 16A and 16B. These figures show an example of error rate results from a multiplex assay as described herein for detecting cocaine (COC), marijuana (THC; tetrahydrocannabinol) and benzodiazepine (BZO).

FIG. 16A shows error rates for false positives (the bars on the left side of the graph; left of 0%)) and false negatives (the bars on the right side of the graph; right of 0%). Error rates are less than 10% for the analytes tested cocaine (COC), marijuana (THC; tetrahydrocannabinol) and benzodiazepine (BZO). False positive and false negative error rates for cocaine are around or less than 4% and 6% respectively for cocaine; around or less than 6% and 4% respectively for THC, and around or less than 2% and 2% respectively for benzodiazepine (BZO) at 0.6×. Other threshold values could be chosen to minimize either false positives or false negatives.

Figure 17A:
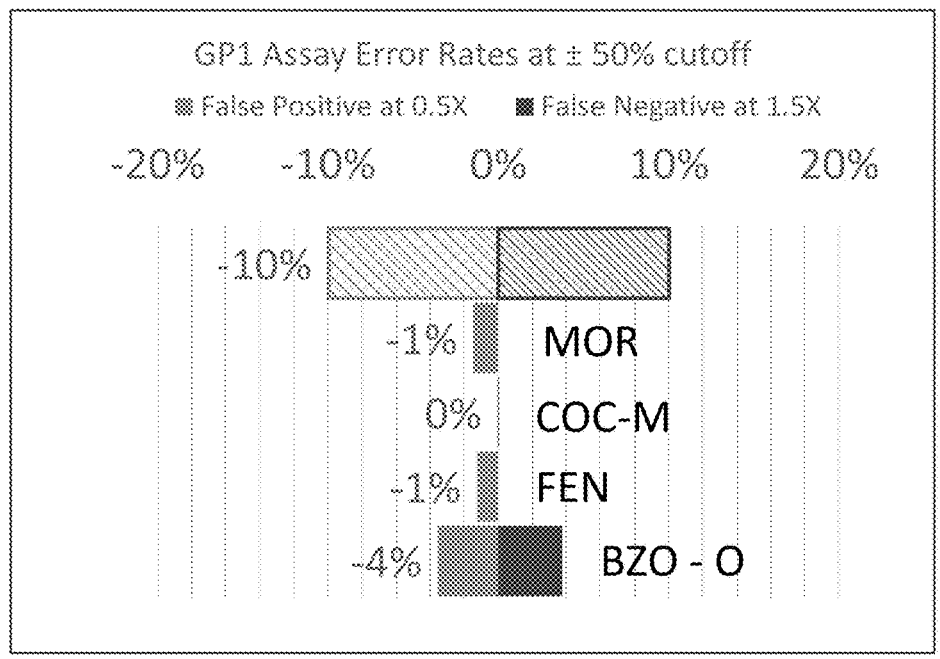
FIGS. 17A-17C show results from a multiplex assay as described herein for detecting cocaine (COC-M), fentanyl (FEN), morphine (MOR) and benzodiazepine (BZO-O) from a bodily fluid sample.
Figure 17B:
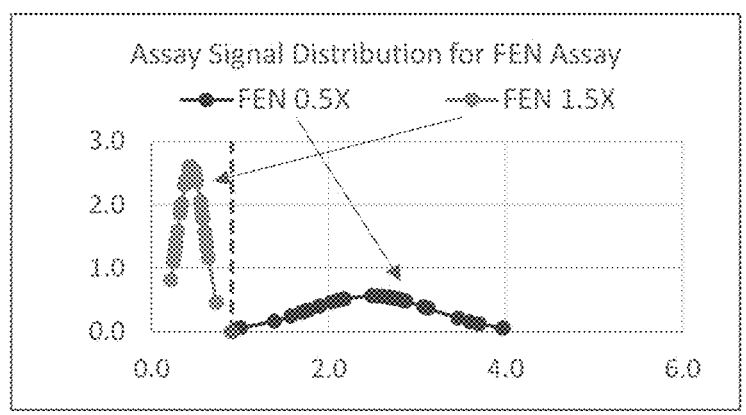
Figure 17C:
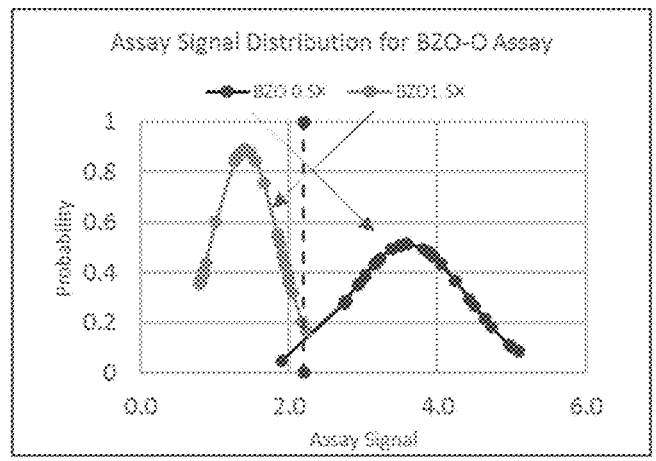

Example 3 is shown in FIGS. 17A-17C. These figures show results from a multiplex assay using the systems and methods described herein including dried beads containing reagents and a serpentine mixer for detecting cocaine (COC-M), fentanyl (FEN), morphine (MOR) and benzodiazepine (BZO-O). Errors are less than 10% and less than 4%. FIG. 17A shows error rates for false positives (the bars on the left side of the graph; left of 0%) and false negatives (the bars on the right side of the graph right of 0%). Error rates are less than 10% for the analytes tested. False positive and false negative error rates for morphine are around or less than 1% and 0%, around or less than 0% and 0% respectively for cocaine, and around or less than 1% and 0% respectively for fentanyl, and around or less than 4% and 4% for benzodiazepine (BZO-O), with false positives at 0.5× and false negatives at 1.5×. Other threshold values could be chosen to minimize either false positives or false negatives. FIG. 17B shows assay signal distribution for the fentanyl (FEN) assay shown in FIG. 17A for fentanyl at 0.5× and 1.5×. FIG. 17C shows a graph of the probability (Y-axis) of an assay signal distribution for the benzodiazepine (BZO-O) for the assay shown in FIG. 17A.

FIGS. 19A-19B show (with individual illustrations) one example of a method of operation of an apparatus as described herein for sampling saliva. In this example, the cartridge, including a saliva collection system (also referred to as a saliva collection sub-systems) is removed from a sterile packaging 1901, and includes the cartridge body (coupled to the collection body) and a cap. The first and second swab pistons extending from the collection body may then be inserted into a subject's mouth to collect saliva 1903; an indicator (colorimetric indicator) on the side of the device may change color to indicate when it is full, and saliva collection is complete 1905. The cap may then be inserted and snapped over the first and second swab pistons (containing the saliva sample); the action of attaching the cap may pierce a frangible cover within the cap and may force the one or more fluids (e.g., a dilution fluid in one side, corresponding to the first swab piston, and a preservation solution in the second side corresponding to the second swab piston) to mix with the saliva samples. The first and second sides may be isolated from each other (fluidically isolated) 1907. The sample to be immediately tested is diluted a predetermined amount and dispensed into the diluted sample cavity within the cartridge. The cartridge may then be inserted into a reader 1909 for processing and reading.

FIG. 19B continues the method shown in FIG. 19A. In FIG. 19B, the cartridge reader may then process the fluid within the cartridge via the fluidic circuit(s), as will be described in greater detail in reference to FIGS. 20A-20N, below, and resulting signals may be read out, as described above 1911. The readout may be qualitative (e.g., above a threshold, within a range indicating "positive", "negative" or "inconclusive", etc. for the presence/absence of a drug of addiction), and/or it may be quantitative (estimating concentration values). The output may be presented and/or stored and/or transmitted.

The entire cartridge may then be stored and/or transmitted for confirmation processing, e.g., at a remote laboratory 1913, 1915. For example, the cartridge may be sealed in a package. The second sample (mixed with the preservation solution within the cartridge, e.g., the collection sub-system portion of the cartridge) may be kept indefinitely until confirmation testing is desired. When retesting of the stored sample is desired, the cartridge may be unsealed, e.g., the tab on the collection device may be broken, and the confirmation test performed 1917.

Any of the processing steps described herein using the microfluidics on the cartridge may include manipulation, e.g., by a reader, of the fluidics circuit within the cartridge. FIGS. 20A-20N illustrate one example of fluidics circuit (similar to that shown in FIG. 7). In FIG. 20A, the circuit is illustrated; FIG. 20B shows a legend or key that may be helpful when reviewing the exemplary operation described and shown schematically in FIGS. 20C-20N.

FIG. 20C illustrates the initialization step, in which the pump (diaphragm) may be set up so that both pushing and pulling of fluid through the device may be allowed. In FIG. 20C, the reader (e.g., a pump piston on the reader) may be pushed at least partway in to deflect (e.g., approximately 50%) the pump diaphragm in the cartridge, as shown. In this case, valves in the reader keep the vents on either side of the diluted sample cavity closed, but leave the waste vent (downstream of the waste reservoir) open, so that only air may pass into the channels. The swab piston (also referred to herein as a swab plunger) in the saliva collection portion has already pushed diluted sample into the Diluted Sample Cavity (DSC) in the cartridge. A cap stop may prevent capillary movement of the sample.

In FIG. 20D, the sample may be metered (e.g., a predetermined volume of diluted sample) by the circuit. Once the reader has closed the waste vent valve and opened the vent downstream of the diluted sample cavity, the reader may then controllably release the pump piston so that the pump (diaphragm) applies negative pressure to pull a sample into the sample metering well (SMW) until a fluid sensor detects a fluid meniscus and stops the pull by holding the pump piston in place. The sample may be 'cleaved' (e.g., so that a bolus of air is added to cut off the metered sample from the diluted sample cavity), by the reader closing the vent downstream from the diluted sample cavity and opening the vent between the diluted sample cavity and the metering well ("sample well"). The pump may be allowed to pull fluid slightly, drawing a bolus of air behind the metered sample in the sample well, as shown in FIG. 20E, accurately separate a slug of metered volume of sample.

In this example, a lyophilised bead (e.g., including a fluorescently labeled antibody to the drug(s) to be identified) may be present in the sample well and may dissolve in the sample. The fluid may then be pulled into the serpentine mixer and moved back and forth within the mixer multiple times to achieve thorough mixing. This is illustrated in FIG. 20F. The reader may achieve this by extending and retracting the pump piston to controllably push and release the pump diaphragm on the cartridge, resulting in pushing and pulling the sample fluid within the mixer; as illustrated above, the mixer may be a serpentine channel. Once mixed, the fluid may be left in the sample channel and allowed to incubate, as shown in FIG. 20G. In some variations, the pump may be released (e.g., allowed to fully relax to a neutral position), by opening the vent downstream from the waste channel, and closing the vents upstream and downstream from the diluted sample cavity.

The control solution within the blister pack may then be dispensed. For example, in FIG. 20H, the blister pack is burst by applying a force (e.g., from a piston) to push the blister pack against the needle within the cartridge, and the control fluid is pushed into the control metering well (CMW) till a fluid sensor detects the meniscus and stops the reader (e.g., a piston for pushing the blister pack) from pushing further. In FIG. 20I, the control fluid may be metered by the reader pushing on the (now air-filled) pump diaphragm. The pump then pushes air into the control channel to accurately separate a slug of metered volume of control fluid. In this example, a lyophilised bead (e.g., fluorescently labeled antibody) in the CMW (control metering well) may dissolve in the control fluid. As shown in FIG. 20J, the control solution (fluid) may then be pulled into the serpentine mixer and moved back and forth within the mixer multiple times to achieve thorough mixing, again by applying pushing force (or relaxing the pushing force) to allow the diaphragm to move in and out, pushing and pulling the control solution through the second serpentine mixing channel. The control fluid is then left in the control channel to allow incubation. After incubation, the control fluid is pushed into the chip channel and data acquisition is done, as shown in FIG. 20K. In this example, the solution may be passed onto the chip and evanescent signals detected as described above. Thereafter, the control fluid may be pushed into the waste well till the chip channel is empty, as shown in FIG. 20L, by the reader pushing (via the pump piston) on the pump diaphragm.

Next, the sample may be pulled into the chip channel and data acquisition done, as shown in FIG. 20M. The vent downstream to the waste channel is closed, and the vent between the sample (metering) well and the diluted sample cavity may be opened, as shown, so that releasing the pump piston by the reader allows the pump diaphragm to apply negative pressure to pull the metered sample solution over the chip, allowing evanescent reading by the chip. Finally, the sample may be pulled into the control channel and pump chamber, as shown in FIG. 20N.

Figure 21:
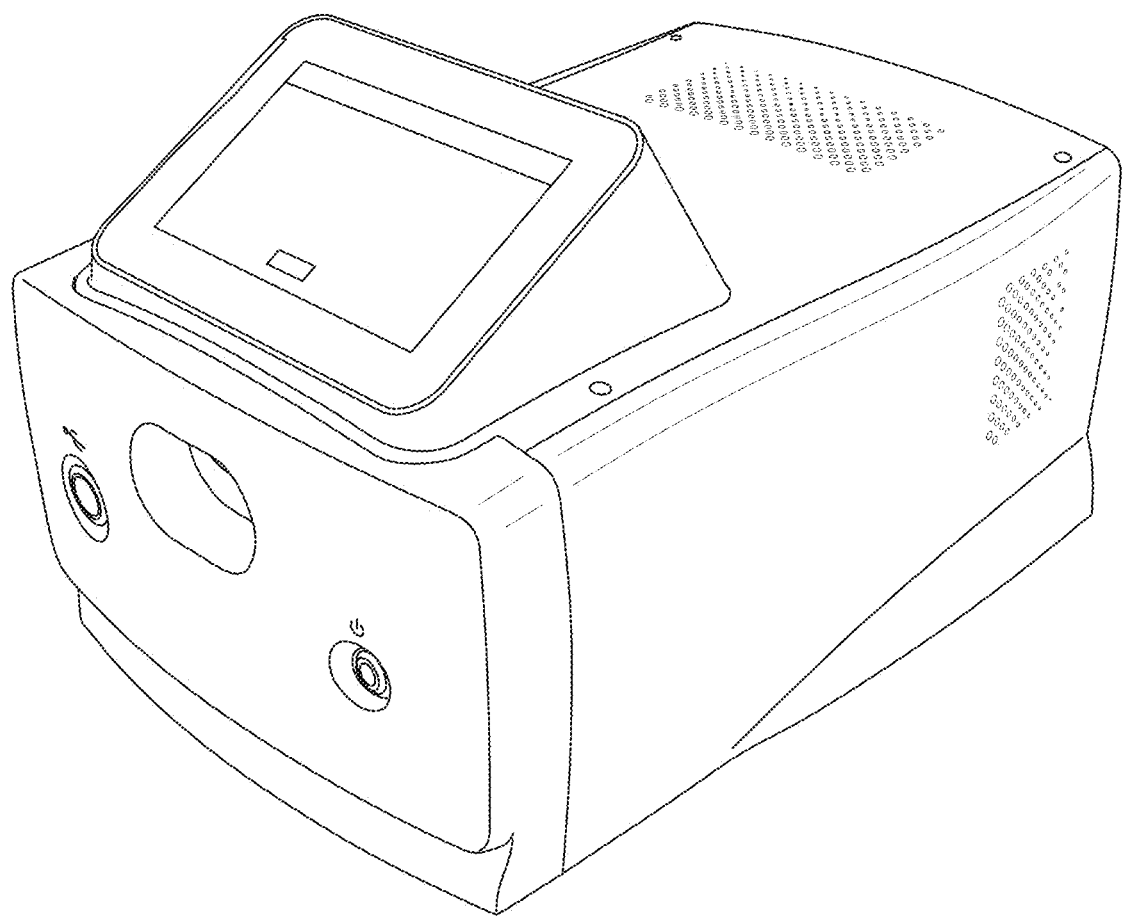
FIG. 21 is an example of a reader for reading a cartridge and automatically performing the method of operating the exemplary cartridge as described herein.

In general, any appropriate reader may be used. A schematic of one example of a desktop reader is shown in FIG. 21. In this example, the reader may include one or more processors (controllers) including a memory, and control circuitry, for controlling the pump piston, the valves, the fluid sensors, and the optical illumination source and optical detector for reading from the photonics chip, as well as hardware, software and/or firmware for processing signals from the photonics chip. The reader may also include one or more outputs (displays, memory, wireless or wired transmitters, printers, removable memory, etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A saliva collection system, the system comprising:
   a collection body;
   a first swab material;
   a second swab material;
   a first swab piston extending distally from the collection body, the first swab piston comprising a first internal channel in fluid communication with the first swab material, wherein the first swab material is configured to wick saliva into an open distal end of the first swab piston;
   a second swab piston extending distally from the collection body, the second swab piston comprising a second internal channel in fluid communication with the second swab material wherein the second swab material is configured to wick saliva;
   a diluted sample cavity in fluid connection with a proximal end of the first internal channel;
   a cap having a first tube configured to receive the first swab piston and a second tube configured to receive the second swab piston;
   a dilution buffer within the first tube and covered by a first frangible cover that is configured to be pierced by the first swab material when the cap is attached to the collection body; and
   a preservation solution within the second tube and covered by a second frangible cover that is configured to be pierced by the second swab material when the cap is attached to the collection body,
   wherein the first swab piston and the first tube are configured so that closing the cap on the collection body plunges the dilution buffer into the first swab piston and the first internal channel to mix and dilute any saliva within the first swab material and to push the mixed and diluted saliva into the diluted sample cavity at a predetermined dilution factor.

2. The system of claim 1 wherein the first swab material in fluid communication with the first internal channel and the second swab material in fluid communication with the second internal channel each comprise a plurality of capillaries.

3. The system of claim 1 wherein the first swab material in fluid communication with the first internal channel and the second swab material in fluid communication with the second internal channel each comprise a porous swab.

4. The system of claim 1, wherein the cap comprises a separable cap.

5. The system of claim 1, wherein the dilution buffer is different from the preservation solution and the preservation solution is configured for long-term storage of a saliva sample.

6. The system of claim 1, wherein the first and second frangible covers comprise a foil cover.

7. The system of claim 1, further comprising a fastener configured to lock the cap to the collection body.

8. The system of claim 1, further comprising a fastener configured to secure the cap to the collection body, wherein the fastener is configured as a snap.

9. The system of claim 1, further comprising a seal around each of the first and second swab pistons configured to prevent passage of fluid out of the first and second tubes of the cap when the first and second swab pistons are engaged with the first and second tubes.

10. The system of claim 1, further comprising a colorimetric indicator on the first or second swab piston configured to indicate a level of saliva within the first or second swab piston.

11. The system of claim 1, further comprising a reader cartridge body extending from the collection body opposite from the first and second swab pistons, wherein the cartridge body is configured for insertion into a reader.

12. The system of claim 11, wherein the cartridge body comprises a photonic chip comprising a plurality of waveguides having an exposed edge on one end of the cartridge body, further comprising a drug bound to a surface in optical communication with one or more of the plurality of waveguides.

13. The system of claim 11, wherein the diluted sample cavity is within the cartridge body.

14. The system of claim 11, wherein the cartridge body comprises a metering well, a serpentine mixing channel, and a pumping diaphragm all in fluid communication with the diluted sample cavity.

15. A saliva collection system, the system comprising:
a collection body;
a first rigid swab material configured to wick saliva;
a second rigid swab material configured to wick saliva;
a first swab piston extending distally from the collection body, the first swab piston comprising a first internal channel in fluid communication with the first rigid swab material through an open distal end of the first swab piston;
a second swab piston extending distally from the collection body, the second swab piston comprising a second internal channel in fluid communication with the second rigid swab material through an open distal end of the second swab piston;
a diluted sample cavity in fluid connection with a proximal end of the first internal channel; and
a cap having a first tube configured to receive the first swab piston and a second tube configured to receive the second swab piston;
a dilution buffer within the first tube;
a preservation solution within the second tube; and
wherein the first swab piston and first tube are configured so that securing the cap to the collection body plunges the first swab piston into the first tube and drives the dilution buffer through the first swab material and into the first internal channel to mix and dilute any saliva and to push the mixed and diluted saliva into the diluted sample cavity at a predetermined dilution factor.

16. A method of collecting saliva from a subject, the method comprising:
placing a first swab piston and a second swab piston of a saliva collection system in the subject's mouth, wherein the first and second swab pistons extend distally from a collection body;
wicking saliva from the subject's mouth into a first swab material in fluid communication with a first internal channel within the first swab piston and into a second swab material in fluid communication with a second internal channel within the second swab piston;
removing the first and second swab pistons from the subject's mouth;
inserting a cap over the first and second swab pistons, so that the first swab piston plunges into a first tube in the cap to drive the first swab material into a dilution buffer and so that the second swab piston plunges into a second tube in the cap to drive the second swab material into a preservation solution; and
wherein plunging the first swab piston into the first tube drives the dilution buffer into the first swab material to mix and dilute saliva within the first swab material and to push the mixed and diluted saliva into a diluted sample cavity at a predetermined dilution factor;
testing the diluted saliva from the diluted sample cavity in a reader device; and
storing the saliva collection system with saliva from the second swab piston for later processing.

17. The method of claim 16, wherein the placing of the first and second swab pistons comprises placing the first and second swab pistons under the subject's tongue.

18. The method of claim 16, wherein the removing of the first and second swab pistons comprises removing the first and second swab pistons after a colorimetric indicator on the first or second swab piston changes color to indicate a level of saliva collected.

19. The method of claim 16, further comprising fastening of the cap comprising snapping the cap onto the collection body.

20. The method of claim 16, wherein the inserting of the cap comprises engaging a seal around the first swab piston within the first tube to prevent leakage of the dilution buffer and engaging a seal around the second swab piston within the second tube to prevent leakage of the preservation solution.

21. The method of claim 16, further comprising fastening of the cap to the collection body by locking the cap to the collection body so that the cap may not be removed without damaging the saliva collection system.

22. The method of claim 16, wherein the testing of the diluted saliva from the diluted sample cavity comprises inserting a cartridge body extending proximally from the collection body into the reader device.

23. The method of claim 22, wherein the inserting of the cartridge body into the reader device comprises inserting the cartridge body so that: an outer edge of a photonic chip in the cartridge body is aligned with an optical sensor in the reader device, a piston in the reader device aligns with a diaphragm on the cartridge, and a plurality of openings in the cartridge body each align with individual valves in the reader device configured to open or close the openings in the cartridge body.

* * * * *